United States Patent [19]

Buschauer et al.

[11] Patent Number: 5,021,431
[45] Date of Patent: *Jun. 4, 1991

[54] IMIDAZOLYL ALKYL GUANIDINE DERIVATIVES, PROCESSES FOR THEIR PREPARATION AND PHARMACEUTICAL PREPARATIONS CONTAINING THESE COMPOUNDS

[75] Inventors: Armin Buschauer, Berlin; Helmut Schickaneder, Eckental; Walter Schunack, Berlin; Sigurd Elz, Mainz; Istvan Szelenyi, Schwaig; Gert Baumann, Munich; Kurt H. Ahrens, Nuremberg, all of Fed. Rep. of Germany

[73] Assignee: Heumann Pharma GmbH & Co., Nuremberg, Fed. Rep. of Germany

[ * ] Notice: The portion of the term of this patent subsequent to Mar. 27, 2007 has been disclaimed.

[21] Appl. No.: 318,467

[22] Filed: Feb. 28, 1989

Related U.S. Application Data

[63] Continuation of Ser. No. 802,976, Nov. 29, 1985, abandoned.

[30] Foreign Application Priority Data

| Apr. 2, 1985 | [DE] | Fed. Rep. of Germany | 3512084 |
| Aug. 6, 1985 | [DE] | Fed. Rep. of Germany | 3528214 |
| Aug. 6, 1985 | [DE] | Fed. Rep. of Germany | 3528215 |

[51] Int. Cl.⁵ .................. A61K 31/44; A61K 31/415; A61K 31/38; C07D 403/13
[52] U.S. Cl. ..................... 514/333; 514/341; 514/397; 514/400; 546/256; 546/278; 548/336; 548/342
[58] Field of Search ............... 548/342, 336; 514/400, 514/341, 333, 397; 546/278, 256

[56] References Cited

U.S. PATENT DOCUMENTS

| Re. 29,761 | 9/1978 | Durant et al. ............ 548/342 X |
| 3,736,331 | 5/1973 | Black et al. ............... 548/342 |
| 4,048,319 | 9/1977 | Black et al. ............. 548/342 X |
| 4,098,898 | 7/1978 | Durant et al. ............ 548/342 X |
| 4,109,003 | 8/1978 | Durant et al. ............ 548/342 X |
| 4,912,119 | 3/1990 | Buschauer et al. ........ 514/341 X |

FOREIGN PATENT DOCUMENTS

| 479910 | 12/1975 | Australia . |
| 41359 | 12/1981 | European Pat. Off. ......... 548/342 |
| 2433625 | 1/1975 | Fed. Rep. of Germany ..... 548/342 |
| 2819874 | 11/1978 | Fed. Rep. of Germany ..... 548/342 |

*Primary Examiner*—Joseph Paul Brust
*Attorney, Agent, or Firm*—Burns, Doane, Swecker & Mathis

[57] ABSTRACT

New imidazolylalkyl-guanidine derivatives are described, which by virtue of their agonistic action on histamine-$H_2$ receptors and in part also due to their additional $H_1$-antagonistic receptor activity can be used in the treatment of cardiac diseases, certain forms of hypertension and diseases of arterial occlusion.

These imidazolylalkyl-guanidine derivatives correspond to the general formula I:

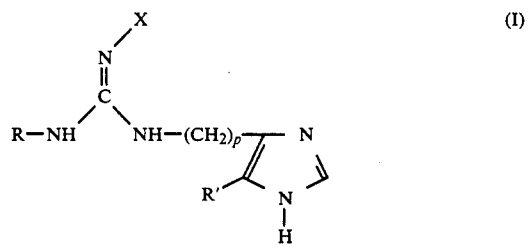

56 Claims, No Drawings

IMIDAZOLYL ALKYL GUANIDINE DERIVATIVES, PROCESSES FOR THEIR PREPARATION AND PHARMACEUTICAL PREPARATIONS CONTAINING THESE COMPOUNDS

This application is a continuation of application Ser. No. 802,976, filed Nov. 29, 1985 now abandoned.

DESCRIPTION

This invention relates to new imidazolyl alkyl guanidine derivatives which may be used in cases of cardiac diseases, certain forms of hypertension and diseases of arterial occlusion by virtue of their agonistic action on histamine-$H_2$ receptors and in part also their additional $H_1$-receptor antagonistic action.

Histamine, which is a specific stimulator of the $H_2$ receptors, releases adverse and in some cases even lethal effects in the form of bronchospasm and anaphylatic shock on account of its $H_1$-agonistic action so that it cannot be used for the treatment of the above mentioned diseases.

It is therefore an object of the present invention to compensate for the adverse effects of histamine and provide improved and selectively more effective $H_2$ agonists in which the harmful side effects due to an $H_1$-agonistic component can be avoided if necessary by means of an additional $H_1$-antagonistic activity profile.

This problem is solved by the present invention.

The invention relates to imidazolyl alkyl guanidine derivatives corresponding to the general, formula I

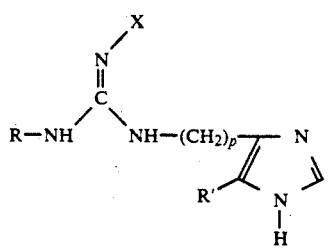

(I)

wherein R represents the group

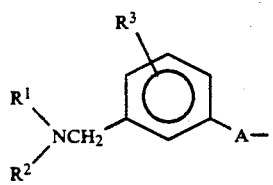

in which $R^1$ and $R^2$, which may be identical or different, denote hydrogen, straight chained $C_1$-$C_{10}$-alkyl or $C_5$-$C_6$-cycloalkyl or $R^1$ and $R^2$ together with the nitrogen atom to which they are attached form a 5- to 10-membered nitrogen-containing alicyclic, heterocyclic ring, $R^3$ denotes a hydrogen atom, a halogen atom or a lower alkoxy group, and A denotes the group $-O-(CH_2)_k-$, $-O-CH_2CH(OH)CH_2-$, $-O-CH_2CH(CH_3)-CH_2-$, $-CH_2-O-CH_2-CH(OH)-CH_2-$ or $-O-CH_2-CH(OH)-CH(OH)-CH_2-$ wherein k has the value 3 or 4, or R represents the group

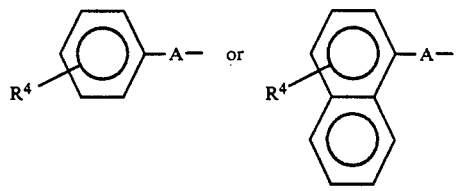

wherein $R^4$ denotes a hydrogen atom, a halogen atom preferably attached in the para-position to A, a lower alkoxy group or a lower alkyl group and A has the meaning indicated above, or R represents the group

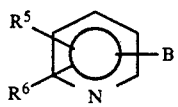

wherein $R^5$ and $R^6$, which may be identical or different, denote a hydrogen atom, a halogen atom or a straight chained lower alkyl or straight chained lower alkoxy group. B, which may be attached in the 2-, 3- or 4-position of the pyridine ring, denotes the group

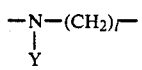

or $-(CH_2)_m$, wherein l has the value 2, 3 or 4 and m the value 3, 4 or 5 and Y denotes a hydrogen atom or a straight chained $C_1$-$C_3$-alkyl group, or R represents the group

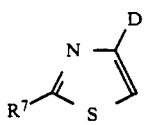

wherein $R^7$ denotes the group $(R^1R^2)N-CH_2-$, $(H_2N)_2C=N-$,

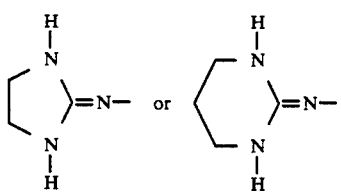

wherein $R^1$ and $R^2$ have the meanings indicated above, and D denotes the group $CH_2-S-(CH_2)_n-$ or $-(CH_2)_o-$ where n has the value 2 or 3 and o the value 2, 3 or 4, or R represents the group

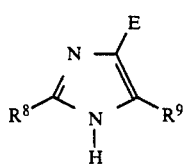

wherein R⁸ denotes a hydrogen atom, a benzyl group optionally substituted by a halogen atom, the group $(R^1R^2)N-CH_2-$ or an amino group, $R^1$ and $R^2$ having the meanings indicated above. $R^9$ denotes a hydrogen atom or a straight chained lower alkyl or lower alkylthio group, and E denotes the group

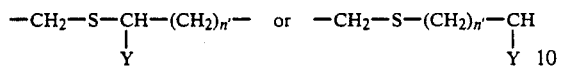

wherein n' has the value 1, 2 or 3
and Y has the meanings indicated above.
or R represents the group N

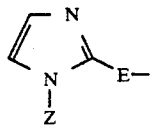

wherein Z denotes a hydrogen atom or a straight chained lower alkyl group and E has the meanings indicated above or R represents the group R'''—A'—B'— wherein R'' denotes substituted or unsubstituted phenyl group or a substituted or unsubstituted naphthyl group, A' denotes a single bond or the group $-CR^{1'}R^{2'}$ or a nitrogen atom substituted by a straight chained $C_1-C_3$-alkyl group or by an aryl, hetaryl or benzyl group, which substituents may in turn be substituted, $R^{1'}$ denoting a hydrogen atom or a methyl group and $R^{2'}$ denoting an optionally substituted phenyl group or optionally substituted heteroaryl group, and B' denotes the group $-CH(Y)-S-(CH_2)_{m'}-$, $-CH_2-S-CH_2-CH(Y)-CH_2-$, $-CH_2-S-CH(Y)-CH_2-$, $-CH_2-S-CH_2-CH(Y)-$, $-(CH_2)_{n''}-$, $-(CH_2)-CH(Y)-$, $-(CH_2)_{n''}-CH(Y)-$, $-O-(CH_2)_2$; $-CH_2-O-(CH_2)_{o'}-$, $-CH_2-O-CH_2-CH(Y)-CH_2$, $-O-CH_2-CH(Y)-$, $-O-CH(Y)-CH_2-$, $-S-(CH_2)_q-$, $-S-CH_2-CH(Y)-$, $-S-CH(Y)-CH_2-$ or $-S-CH-CH(Y)-CH_2$ wherein Y denotes a hydrogen atom or a straight chained $C_1-C_3$-alkyl group, m' and o' have the value 2 or 3 and n'' and q have the value 2, 3, 4 or 5, or R represents the group R''''—A''—B'' wherein R''' denotes a substituted or unsubstituted heteroaryl group to which optionally a condensed phenyl ring may be attached, A'' denotes a single bond or the group $-CR^{1'}R^{2'}$ or it denotes nitrogen atom substituted with a straight chained $C_1-C_3$-alkyl group or with an aryl, hetaryl or benzyl group which may in turn be substituted, $R^{1'}$ denoting a hydrogen atom or a methyl group and $R^{2'}$ an optionally substituted phenyl group or optionally substituted heteroaryl group, and B'' denotes the group $-CH(Y)-S-(CH_2)_{m'}-$, $-CH_2-S-CH_2-CH(Y)-CH_2-$, $-CH_2-S-CH(Y)-CH_2-$, $-(CH_2)_{n''}-CH(Y)-$, $-CH_2-S-CH_2-CH(Y)-$, $-(CH_2)_{n''}-$, $-O(CH_2)_{n'}-$, $-S-CH-CH(Y)-$, $-S-CH(Y)-CH_2-$, $-S-(CH_2)_q-$ or $-S-CH_2-CH(Y)-CH_2-$ wherein Y denotes a hydrogen atom or a straight chained $C_1-C_3$-alkyl group, m' has the value 2 or 3 and n'' and q have the value 2, 3, 4 or 5, X denotes a hydrogen atom or a benzoyl group, p has the value 2 or 3 and R' denotes a hydrogen atom or a methyl group, and the physiologically acceptable salts thereof.

In this context, the terms "lower alkyl group" and "lower alkoxy group" used to describe alkyl and alkoxy groups denote groups containing 1 to 3 carbon atoms in the alkyl moiety.

In a preferred group of compounds according to the invention, R represents the group

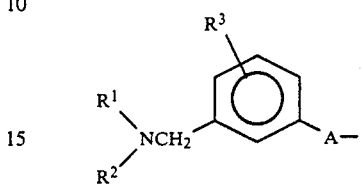

in which the substituents $R^1$ and $R^2$, which may be identical or different, denote a hydrogen atom or a straight chained $C_1-C_{10}$-alkyl group, preferably a straight chained $C_1-C_6$-alkyl group, most preferably a straight chained $C_1-C_3$-alkyl group such as, for example, a methyl, ethyl or n-propyl group, in particular a methyl group. Alternatively, $R^1$ and $R^2$ together with the nitrogen atom to which they are attached may form a 5- to 10-membered, nitrogen-containing alicyclic, heterocyclic ring. Preferred examples of 5- to 10-membered heterocyclic rings thus defined are the pyrrolidine, piperidine and homopiperidine ring. $R^3$ denotes a hydrogen atom or a halogen atom which is attached to the $(R^1R^2)N-CH_2$-group in the ortho-, meta- or or para-position, preferably the ortho-position. $R^3$ may also denote a lower alkoxy group, e.g. methoxy group, which also may be attached in the ortho-, meta- or para-position to the $(R^1R^2)N-CH_2-$ group, preferably in the para-position. A denotes one of the following groups: $-O(CH_2)_k-$, $-O-CH_2CH(OH)CH_2-$, $-O-CH_2-CH(CH_3)-CH_2-$, $-CH_2-O-CH_2-CH(OH)-CH_2-$ or $-O-CH_2-CH(OH)-CH(OH)-CH_2-$. The symbol k in the given formula may have the value 3 or 4, the value 3 being preferred. X denotes a benzoyl group or a hydrogen atom, the hydrogen atom being preferred. R' denotes a hydrogen atom or a methyl group, preferably a hydrogen atom.

In another preferred group of compounds according to the invention, R in the general formula I represents the group

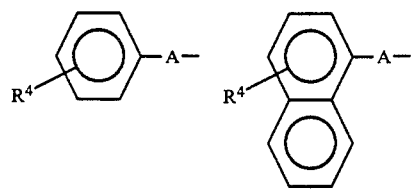

wherein $R^4$ denotes a hydrogen atom, a halogen atom preferably attached in the para-position to A, e.g. a fluorine, bromine or chlorine atom, preferably a chlorine atom, a lower alkoxy group such as a methoxy or ethoxy group, a lower alkyl group such as a methyl or ethyl group, the hydrogen atom being particularly preferred. A conforms to the above definition and preferably denotes the group $-O-(CH_2)_3-$ or $-O-CH_2CH(OH)CH_2-$; X also conforms to the above definition and preferably denotes a hydrogen atom. p conforms to the above definition and preferably has the value 3. R' preferably denotes a hydrogen atom.

In another preferred group of compounds according to the invention, R in the general formula I represents the group

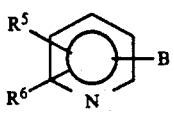

wherein $R^5$ and $R^6$, which may be identical or different, denote a hydrogen atom or a halogen atom, e.g. a fluorine, chlorine or bromine atom, preferably a bromine atom. The halogen atom may be preferably attached in the 3- and/or 5-position of the pyridine ring. When $R^6$ is a hydrogen atom then $R^5$ is preferably a halogen atom, e.g. a fluorine, chlorine or bromine atom, in particular a bromine atom. The halogen atom may be preferably attached in the 3- or 5-position, in particular the 5-position of the pyridine ring. $R^5$ and $R^6$ may also denote a lower alkyl or lower alkoxy group, preferably a methyl or methoxy group attached in the 3- and/or 5-position of the pyridine ring. When $R^5$ is a hydrogen atom then $R^6$ is preferably a methyl or methoxy group attached in the 3- or 5-position of the pyridine ring.

B, which may be attached in the 2-, 3- or 4-position of the pyridine ring, preferably in the 2- or 3-position, denotes the group

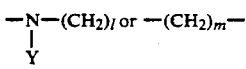

wherein Y denotes a hydrogen atom or a straight chained lower alkyl group, preferably a methyl, ethyl, n-propyl or isopropyl group, in particular a methyl group. The symbol l has the value 2, 3 or 4, preferably 2 or 3, and m has the value 3, 4 or 5, preferably 4. The symbol X preferably denotes a hydrogen atom, p has the value 2 or 3, preferably 3, and R' preferably denotes a hydrogen atom.

In another preferred group of compounds according to the invention, R represents the group

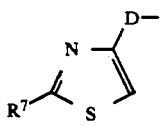

wherein the substituent denoted by $R^7$ may be the group $(R^1R^2)N$—$CH_2$— in which $R^1$ and $R^2$, which may be identical or different, denote a straight chained $C_1$-$C_{10}$-alkyl group, preferably a straight chained $C_1$-$C_3$-alkyl group such as a methyl, ethyl or n-propyl group, the methyl group being preferred. Furthermore, $R^7$ may denote the group $(H_2N)_2C$=$N$—,

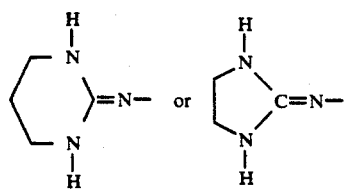

the last two mentioned groups being particularly preferred. D denotes a connecting link —$CH_2$—$S$—$(CH_2)_n$— or —$(CH_2)_o$— wherein n has the value 2 or 3, preferably 2, and o has the value 2, 3 or 4, preferably 3.

In another preferred group of compounds according to the invention, R in the general formula I represents the group

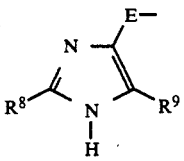

wherein $R^8$ denotes a hydrogen atom or a benzyl group which is optionally substituted in the para-position by a halogen atom, e.g. a bromine or chlorine atom, preferably a chlorine atom. $R^8$ may also represent the group $(1R^2)N$—$CH_2$— wherein $R^1$ and $R^2$ have the meanings indicated above but are preferably each a methyl group. $R^8$ may also be an amino group but is preferably a hydrogen atom. $R^9$ denotes a hydrogen atom, a straight chained lower alkyl group, e.g. a methyl or ethyl group, preferably a methyl group, or a lower alkylthio group, the methylthio group being particularly preferred. When $R^8$ denotes a hydrogen atom and $R^9$ a methylthio group then E preferably denotes the group —$CH_2$—$S$—$(CH_2)_n$— wherein n has the value 2 or 3, preferably 2. Another preferred meaning for E is the group

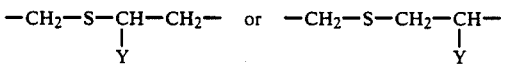

wherein Y denotes a lower alkyl group, for example a methyl or ethyl group, preferably a methyl group.

In another preferred group of compounds according to the invention, R in the general formula I represents the group

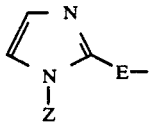

wherein Z denotes a hydrogen atom or a straight chained lower alkyl group, preferably a methyl group, and E has the definition given above but preferably denotes the group —$CH_2$—$S$—$(CH_2)_2$—. X and R' preferably represent each a hydrogen atom, and p conforms to the definition given above but preferably has the value 3.

In another preferred group of compounds according to the invention, R in the general formula I represents the group R''—A'—B'— wherein R'' denotes a substituted or unsubstituted phenyl group or a substituted or unsubstituted naphthyl group. When R'' denotes a substituted phenyl or substituted naphthyl group, it may be represented by the formula

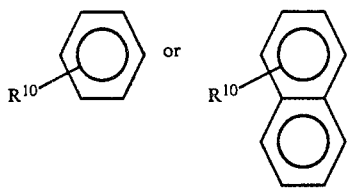
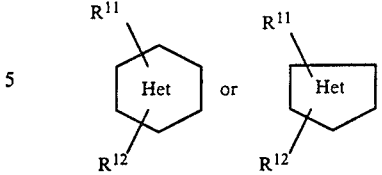

wherein $R^{10}$ may denote a halogen atom preferably attached in the meta- or para-position to R, e.g. a fluorine, bromine, chlorine or iodine atom, preferably a fluorine or chlorine atom, the fluorine atom being particularly preferred: or it may denote a straight chained $C_1$-$C_3$-alkyl group, e.g. a methyl or ethyl group, a straight chained $C_1$-$C_3$-alkoxy group, e.g. a methoxy group, or a trifluoromethyl group. A' denotes a single bond, the group —$CR^{1'}R^{2'}$ or a nitrogen atom which is substituted with an optionally substituted aryl, hetaryl or benzyl group or with a hydrogen atom or with a straight chained $C_1$-$C_3$-alkyl group. The aryl, hetaryl or benzyl group may be substituted, for example, in the meta- or para-position, preferably the para-position, with a halogen atom, e.g. a fluorine, chlorine, bromine or iodine atom, preferably a fluorine atom, or with a straight chained $C_1$-$C_3$-alkyl group, e.g. a methyl, ethyl or propyl group, preferably a methyl group, or with a straight chained $C_1$-$C_3$-alkoxy group, e.g. a methoxy, ethoxy or propoxy group, preferably a methoxy group.

$R^{1'}$ denotes a hydrogen atom or a methyl group while $R^{2'}$ denotes a substituted or unsubstituted phenyl group or a substitute or unsubstituted heteroaryl group. The heteroaryl group may be, for example, a pyridine ring, a thiophene ring or a furan ring. If the phenyl group or the heteroaryl group is substituted, the substituent is preferably a halogen atom, e.g. a fluorine, bromine, chlorine or iodine atom, preferably a fluorine or chlorine atom, or a straight chained $C_1$-$C_3$-alkyl group, e.g. a methyl or ethyl group, or a straight chained $C_1$-$C_3$-alkoxy group, e.g. a methoxy group.

B' denotes one of the groups —CH(Y)—S—(CH$_2$)$_{m'}$—, —CH$_2$—S—CH$_2$—CH(Y)—CH$_2$—, —CH$_2$—S—CH(Y)—CH$_2$—, —(CH$_2$)—CH(Y)—, —CH$_2$—S—CH$_2$—CH(Y)—, —(CH$_2$)$_{n''}$—, —(CH$_2$)$_{n''}$—CH(Y)—, —O—(CH$_2$)$_2$—, CH$_2$—O—(CH$_2$)$_{o'}$—, —CH$_2$O—CH$_2$—CH(Y)—CH$_2$—, —O—CH$_2$—CH(Y)—, —O—CH(Y)—CH$_2$—, —S—(CH$_2$)$_q$—, —S—CH$_2$—CH(Y)—, —S—CH(Y)—CH$_2$— or —S—CH$_2$—CH(Y)—CH$_2$. In these groups, Y denotes a hydrogen atom or a straight chained $C_1$-$C_3$-alkyl group as defined above, preferably a methyl group, m' and o' have the value 2 or 3, and n" and q have the value 2, 3, 4 or 5.

The symbol X denotes a hydrogen atom or a benzoyl group, p has the value 2 or 3 and R' denotes a hydrogen atom or a methyl group. In another preferred group of compounds according to the invention, R in the general formula I represents the group R'''—A"—B"— wherein R''' denotes a substituted or unsubstituted heteroaryl group to which a condensed phenyl ring may be attached. The heteroaryl group may be, for example, pyridine, imidazole, pyrimidine, thiophene, furan, benzimidazole or quinoline ring. The hetero ring denoted by R''' may be substituted or unsubstituted. When the hetero ring is substituted, R''' may represent the group wherein $R^{11}$ and $R^{12}$ denote, independently of one another, a halogen atom, e.g. a fluorine, bromine, chlorine or iodine atom, preferably a fluorine or chlorine atom, or a straight chained $C_1$-$C_3$-alkyl group, e.g. a methyl, ethyl or propyl group, preferably a methyl group, or a straight chained $C_1$-$C_3$-alkoxy group, preferably a methoxy group. A" denotes a single bond or the group —$CR^{1'}R^{2''}$ or a nitrogen atom which is substituted with an optionally substituted aryl, hetaryl or benzyl group or with a hydrogen atom or with a straight chained $C_1$-$C_3$-alkyl group. The aryl, hetaryl or benzyl group may be substituted, for example, in the meta- or para-position, preferably the para-position, with a halogen atom, e.g. a fluorine, chlorine, bromine or iodine atom, preferably a fluorine or chlorine atom, or with a straight chained $C_1$-$C_3$-alkyl group, e.g. a methyl, ethyl or propyl group, preferably a methyl group, or with a straight chained $C_1$-$C_3$-alkoxy group, e.g. a methoxy, ethoxy or propoxy group, preferably a methoxy group.

$R^{1'}$ denotes a hydrogen atom or a methyl group while $R^{2'}$ denotes a substituted or unsubstituted phenyl group or a substituted or unsubstituted heteroaryl group. The heteroaryl group may be, for example, a pyridine ring, a thiophene ring or a furan ring. When the phenyl group or the heteroaryl group is substituted, the substituent is preferably a halogen atom, e.g. a fluorine, bromine, chlorine or iodine atom, in particular a fluorine or a chlorine atom, a straight chained $C_1$-$C_3$-alkyl group, e.g. a methyl or ethyl group, or a straight chained $C_1$-$C_3$-alkoxy group, e.g. a methoxy group. When A denotes a single bond, this bond is situated in the 2-, 3- or 4-position of the heteroaryl group, i.e. it links the group B as defined above with the heteroaryl group in the 2-, 3- or 4-position of the heteroaryl group. When the heteroaryl ring is a benzimidazole ring, the only possible position for the linkage is the 2-position of the benzimidazole ring.

B" denotes one of the groups —CH(Y)—S—(CH$_2$)$_{m'}$—, —CH$_2$—S—CH$_2$—CH(Y)—CH$_2$—, —CH$_2$—S—CH(Y)—CH$_2$—, —(CH$_2$)—CH(Y)—, —CH$_2$—S—CH$_2$—CH(Y)—, —(CH$_2$)$_{n'''}$—, —O(CH$_2$)$_{n''}$—, —(CH$_2$)$_n$—CH(Y)—, —S—CH —CH(Y)—, —S—CH(Y)—CH$_2$—, —S—(CH$_2$)$_q$— or —S—CH$_2$—CH(Y)—CH$_2$—, wherein Y denotes a hydrogen atom or a straight chained $C_1$-$C_3$-alkyl group, m' has the value 2 or 3 and n" and q have the value 2, 3, 4 or 5.

X denotes a hydrogen atom or a benzoyl group, p has the value 2 or 3 and R' denotes a hydrogen atom or a methyl group.

In a preferred group of compounds according to the invention, R''' represents the group

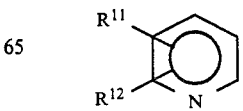

wherein $R^{11}$ and $R^{12}$ have the meanings defined above. A″ in this case preferably denotes the group —$CR^{1'}R^{2'}$ wherein $R^{1'}$ denotes a hydrogen atom or a methyl group, preferably a hydrogen atom. $R^{2'}$ denotes a phenyl group optionally substituted in the 4-position by a halogen atom, e.g. a fluorine, chlorine, bromine or iodine atom. preferably a fluorine or chlorine atom, or by a straight chained $C_1$-$C_3$-alkyl group, preferably a methyl group. In this case, another preferred meaning for A″ is the nitrogen atom substituted with an aryl, hetaryl, benzyl or methyl group or with a hydrogen atom, preferably with an aryl or benzyl group. Furthermore, when in this case A″ denotes the group —$CR^{1'}R^{2'}$, then B″ preferably denotes the group —$(CH_2)_n$—, —O—$(CH_2)_2$— or —S—$CH_2CH_2$—, in particular —$(CH_2)_n$— where n has the value defined above, preferably the value 2 or 3. Furthermore, in this preferred group of compounds, when A″ denotes a nitrogen atom substituted with an aryl, hetaryl, benzyl or methyl group or with a hydrogen atom, then B″ denotes the group —$(CH_2)_n$— where n preferably has the value 2 or 3. Furthermore, X and R′ in this case preferably denote each a hydrogen atom and p preferably has the value 3.

In another preferred group of compounds according to the invention, R′″ in the general formula I represents the group

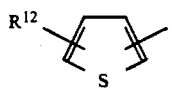

wherein $R^{12}$ denotes a hydrogen atom, a halogen atom, preferably a chlorine atom, a straight chained $C_1$-$C_3$-alkyl group, preferably a methyl group, or the group $(CH_3)_2$—$NCH_2$— or

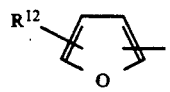

and A″ conforms to the definition given above and preferably denotes a single bond in the 2-position. B″ in this case denotes the group —$CH_2$—S—$CH_2$—$CH_2$—, —$CH_2$—S—$CH_2$—$CH(CH_3)$—$CH_2$—, —$CH_2$—S—$CH(CH_3)$—$CH_2$— or —$CH_2$—S—$CH_2$—$CH(CH_3)$, preferably —$CH_2$—S—$CH_2CH_2$—. X and R′ also conform to the above definition and preferably denote a hydrogen atom, and p preferably has the value 3.

In another preferred group of compounds according to the invention, R′″ in the general formula I represents the group

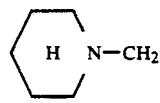

wherein $R^{12}$ has the meanings defined above. A″ in this case is preferably a single bond in the 2-position and B″ denotes one of the groups mentioned above, preferably the group —CH —S—$CH_2CH_2$—, X and R′ preferably denote each a hydrogen atom and p preferably has the value 3.

In another preferred group of compounds according to the invention, R′″ in the general formula I represents the group

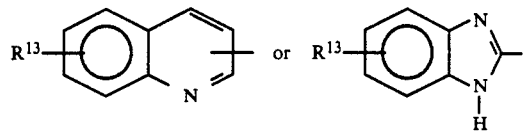

wherein $R^{13}$ has the same meaning as $R^{12}$, A″ preferably denotes a single bond, B″ denotes one of the groups mentioned above, preferably the group —$CH_2$—S—$CH_2CH_2$—, X and R′ preferably denote each a hydrogen atom and p preferably has the value 3.

The invention also covers all stereoisomeric forms and hydrates of the compounds of the general formula I described above.

Compounds according to the invention in which R, p and R′ have the meanings defined above and X denotes benzoyl group may be prepared by two different process variations, namely ($a_1$) by the reaction of a compound corresponding to the general formula (II)

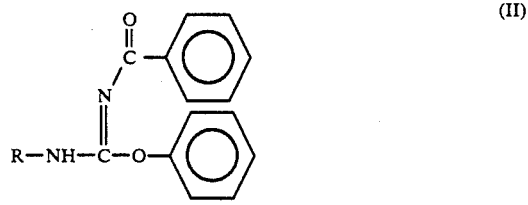

wherein R has the meaning indicated above with a compound corresponding to the general formula III

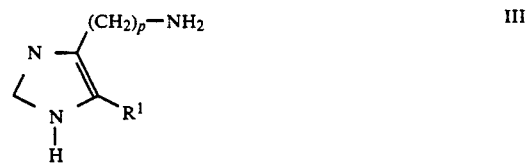

wherein R′ and p have the meanings indicated above to form a compound corresponding to the general formula I.

The reaction between the starting materials is preferably carried out in equimolar quantities in a polar solvent, e.g. an alcohol such as methanol, ethanol or isopropanol, preferably ethanol, or in acetonitrile, dimethylsulphoxide, dimethylformamide or pyridine, preferably acetonitrile or pyridine, at room temperature or at the reflux temperature of the solvent used. ($a_2$) or by the reaction of a compound corresponding to the general formula IV

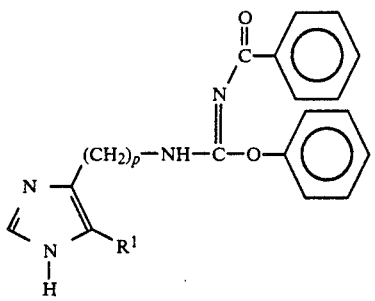

wherein R' and p have the meanings indicated above with a compound corresponding to the general formula V

R—NH₂  (V)

wherein R has the meanings indicated above to form a compound corresponding to the general formula I.

The quantities of solvent used and the reaction conditions are the same as described above for process variation (a₁).

Compounds according to the invention corresponding to the general formula I in which R, p and R' have the meanings defined above and X denotes a hydrogen atom may be prepared by one of the following four process variations:

(b₁) by hydrolysis of a compound corresponding to formula Ia

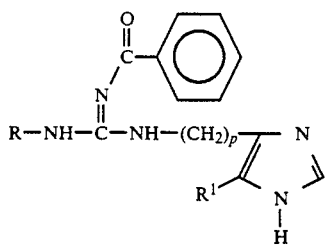

wherein R, p and R' have the meanings indicated above. The hydrolysis may be carried out under acid or alkaline conditions, acid hydrolysis being preferred, for example using dilute sulphuric or dilute hydrochloric acid, in particular hydrochloric acid. The reaction of hydrolysis is carried out at elevated temperature, preferably at the reflux temperature.

(b₂) by hydrolysis of a compound corresponding to formula VI

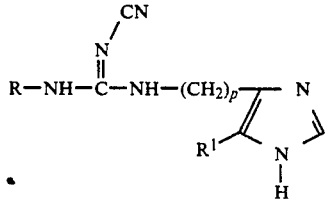

wherein R, p and R' have the meanings indicated above to a compound corresponding to formula I by means of an acid, e.g. dilute sulphuric or dilute hydrochloric acid, preferably hydrochloric acid, as indicated above.

(b₃) by the reaction of a compound corresponding to the general formula VII

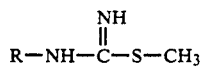

wherein R has the meanings indicated above with a compound corresponding to the general formula III

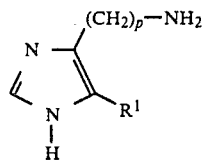

wherein R' and q have the meanings indicated above to form a compound corresponding to the general formula I.

The reaction is carried out in a polar solvent, preferably in pyridine, over a period of 3 to 5 hours and at the reflux temperature of the solvent used (b₄) by the reaction of a compound corresponding to the general formula VIII

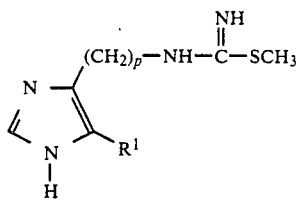

wherein R' and p have the meanings indicated above with a compound corresponding to the general formula V wherein R has the meanings indicated above to form a compound corresponding to the general formula I.

In this variation of the process, the reaction is again carried out in a polar solvent, preferably pyridine, for 3 to 5 hours and at the reflux temperature of the solvent used.

The compounds obtained by the different variations of the process are isolated and purified in the usual manner, for example by chromatographic methods, recrystallisation, etc.

The compounds obtained from the different variations of the process may if desired be converted into their physiologically acceptable salts.

The invention therefore covers not only the stereoisomers and hydrates of the compounds corresponding to the general formula I but also their physiologically acceptable salts. These salts may be formed, for example, with mineral acids such as hydrochloric, hydrobromic or hydriodic acid, phosphoric acid, metaphosphoric acid, nitric acid or sulphuric acid or with organic acids such as formic acid, acetic acid, propionic acid, phenylacetic acid, tartaric acid, citric acid, fumaric acid, methane sulphonic acid, embonic acid, etc.

The compounds according to the invention may be formulated in any desired manner for administration. The invention therefore also covers pharmaceutical preparations containing at least one compound according to the invention for use in human or veterinary medicine. Such pharmaceutical preparations may be prepared by conventional methods using one or more pharmaceutical carriers or diluents.

The compounds according to the invention may therefore be formulated for oral, buccal, topical, parenteral or rectal administration.

For oral administration, the medicament may be prepared in the form of, for example, tablets, capsules, powders, solutions, syrups or suspensions prepared with the aid of acceptable diluents in the usual manner.

For buccal administration, the pharmaceutical preparation may assume the form of tablets or sachets formulated in the usual manner.

The compounds according to the invention may also be formulated for parenteral administration by bolus injection or continuous infusion. Formulations for injection may be prepared in the form of ampoules of unit doses or in multiple dose containers with added preservative.

The pharmaceutical preparations may assume the form of suspensions, solutions or emulsions in oily or aqueous carriers and they may contain formulating auxiliaries such as dispersing or suspending agents and/or stabilizers.

Alternatively, the active ingredient may be prepared in powder form to be reconstituted before use with a suitable carrier such as sterile, pyrogen-free water.

The compounds according to the invention may also be formulated for rectal administration, for example in the form of suppositories or retention enemas which may contain, for example, the usual suppository excipients such as cocoa butter or other glycerides.

For topical application, the compounds according to the invention may be formulated in the usual manner as ointments, creams, gels, lotions, powders or sprays.

For oral administration, a suitable daily dose of compounds according to the invention is one to four doses up to a total of 5 mg to 1 g/day, depending on the patient's condition. In individual cases, it may be necessary to deviate from the quantities indicated above, depending on the individual response to the active ingredient or the nature of its formulation and time or interval of time at which the medicament is administered. Thus in some cases, for example, it may be sufficient to administer less than the minimum quantity indicated above whereas in other cases it may be necessary to exceed the upper limit.

The compounds according to the invention are distinguished by a novel overall pharmacological activity not hitherto known or described.

The new class of structures according to the invention has both an $H_1$-antagonistic and an $H_2$-agonistic active component. This is demonstrated by the following pharmacological results. One recognized method for determining $H_1$-antagonistic activity is the determination of the $pA_2$-values in vitro (O. ARUNLAKSHANA and H. O. SCHILD (1959) Some quantitative uses of drug antagonists—Br. J. Pharmacol. Chemother. 14, 48–58).

For determining the $H_2$-agonistic activity ($pD_2$-values), use is made of the method according to J. M. VAN ROSSUM, (1963), Cumulative dose-response curves, II, Technique for the making of dose-response curves in isolated organs and the evaluation of drug parameters, Arch. Int. Pharmacodyn. Ther. 143, 299–307.

Pharmacological Data (determined on the isolated atrium or ileum of the guinea-pig)

The values listed below represent the $H_2$-agonistic ($pD_2$) and $H_1$-antagonistic ($pA_2$) effect of the dual active compounds

| Pharmacological Data (determined on the isolated atrium or ileum of the guinea pig | | |
|---|---|---|
| Compound | $pD_2$ right atrium | $pA_2$ ileum |
| Example 62 | 5.41 | 4.94 |
| Example 78 | 7.17 | 7.20 |
| Example 96 | 6.9 | 6.9 |
| Example 96 | 6.9 | 6.9 |
| Example 97 | 6.7 | 6.8 |
| Example 101 | 6.15 | 7.41 |
| Example 102 | 6.63 | 7.6 |
| Example 103 | 5.57 | 7.53 |
| Example 104 | 5.16 | 7.24 |
| Example 123 | 6.65 | 7.0 |
| Example 127 | 7.4 | 7.28 |
| Example 129 | 7.2 | 7.5 |
| Example 131 | 7.08 | 6.5 |
| Example 133 | 7.9 | 7.5 |
| Example 136 | 6.95 | 6.6 |
| Example 145 | 5.22 | 6.4 |
| Example 146 | 5.96 | 6.0 |
| Example 134 | 7.03 | 7.3 |
| Example 140 | 5.9 | 8.05 |
| Example 141 | 6.0 | 7.91 |
| Example 142 | 5.8 | 8.08 |
| Example 143 | 5.71 | 8.59 |
| Example 144 | 5.22 | 6.4 |
| Example 147 | 7.0 | 6.9 |
| Example 148 | 6.5 | 7.8 |
| Example 10 | 6.05 | 6.95 |
| Example 12 | 6.70 | 6.25 |
| Example 17 | 5.92 | 8.49 |
| Example 51 | 7.17 | 5.50 |
| Example 60 | 6.54 | 5.64 |
| Example 78 | 7.17 | 7.20 |
| Example 105 | 7.29 | 5.91 |
| Example 121 | 7.29 | 5.70 |
| Example 127 | 7.40 | 7.28 |

EXAMPLE 1

Preparation of the preliminary stages a) N-Benzoyl-diphenylimidocarbonate

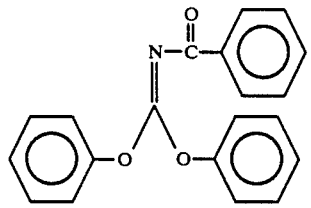

21.0 g (104 mmol) of Benzoylisocyanide dichloride and 20.5 g (218 mmol) of phenol are dissolved in ethyl acetate and 45 ml of pyridine are added dropwise with cooling. After 30 minutes the reaction mixture is concentrated by evaporation under vacuum, the residue is stirred up with benzene and the precipitated pyridinium chloride is filtered off. After removal of the benzene by evaporation under vacuum, a brown oil is left behind which crystallises when kept in the refrigerator. The crude crystal is stirred up several times with ether at room temperature and the insoluble residue is in each case filtered off. The combined ether extracts are concentrated by evaporation under vacuum and kept in the refrigerator for crystallisation. Yield: 23.7 g (72%) of colourless needles which melt at 108° C. after recrystallisation from ether.

IR (KBr): 1710 (C=O), 1645 cm$^{-1}$.

$C_{20}H_{15}NO_3$ (317.3) Calc.: C 75.70 H 4.76 N 4.41. Found: C 75.72 H 4.70 N 4.47.

MS: m/z (rel. Int.[%])=224 ([M-93]$^+$, 24), 105 ([$C_6H_5CO$]$^+$, 100), 94 ([$C_6H_5OH$]$^+$, 9), 77([$C_6H_5$]$^+$, 83).

$^1$H-NMR data (CDCl$_3$, TMS as internal standard): δ=7.2–7.55 (m) 13 H, 7.93 (m) 2 H, ppm.

b) N-Benzoyl-O-phenyl-N'[3-(3-piperidinomethyl-phenoxy) propyl] isourea

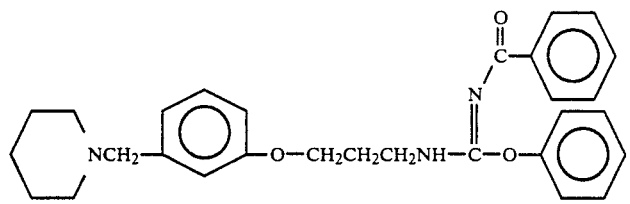

2.48 g (10 mmol) of 3-(3-Piperidinomethyl-phenoxy) propylamine and 3.17 g (10 mmol) of N-benzoyl-diphenylimidocarbonate are stirred in 20 ml of ether at room temperature for one hour. The reaction mixture is concentrated by evaporation under vacuum, the residue is dissolved in methanol, and water is added dropwise until the solution becomes cloudy. When this reaction mixture is kept in a refrigerator, 4.40 g (93%) of N-benzoyl-O-phenyl-N'-[3-(3-piperidinomethyl-phenoxy)propyl] isourea crystallise as colourless needles, melting point 67° C.

$C_{29}H_{33}N_3O_3$(471.6) Calc.: C 73.86 H 7.05 N 8.91. Found: C 73.82 H 7.15 N 8.89.

MS: m/z (rel. Int. [%])=471 (M$^+$, 7), 388 ([M-93]$^+$, 35), 105 ([$C_6H_5CO$]$^+$, 100), 94 ([$C_6H_5OH$]$^+$45), 84 ([$C_5H_{10}N$]$^+$, 40), 77 ([$C_6H_5$]$^+$, 55).

IR (KBr): 1640 (C=O) cm$^{-1}$ $^1$H-NMR data (CDCl$_3$, TMS as internal standard): δ=1.2–1.8 (m) 6 H, 2.20 (m) 2 H, 2.37 (m) 4H, 3.40 (s) 2 H, 3.78 (dt) 2 H, 4.13 (t) 2 H, 6.60–7.55 (m) 12 H, 7.87 (m) 2 H, 10.25 (t, broad) 1 H, replaceable by D$_2$O, ppm.

N-Benzoyl-N'-[2-(imidazol-4-yl)ethyl]-N''-[3-(3-piperidinomethylphenoxy)propyl]guanidine

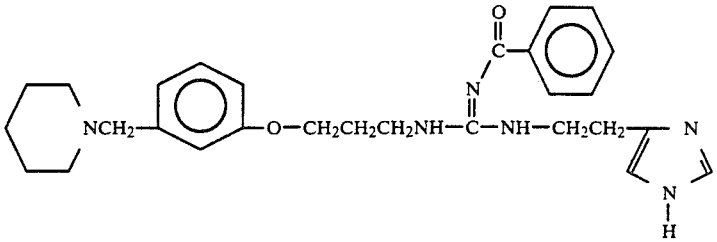

The base is liberated from 0.92 g (5 mmol) of histamine dihydrochloride by means of 10 mmol of sodium ethylate in 100 ml of ethanol, the precipitated sodium chloride is filtered off and the filtrate is concentrated to about 20 ml by evaporation under vacuum. After the addition of 2.36 g (5 mmol) of N-benzoyl-O-phenyl-N'-[3-(3-piperidinomethyl-phenoxy)propyl]-isourea, the reaction mixture is heated under reflux for one hour and concentrated by evaporation under vacuum, and the residue is dissolved in hot acetonitrile. 1.2 g (49%) of N-benzoyl-N'-[2-(imidazol-4-yl)ethyl]-N''-[3-(3-piperidinomethyl-phenoxy) propyl]guanidine crystallize on cooling, melting point 136° C.

Comparable yields are obtained in the same reaction time when pyridine, acetonitrile or tert.-butanol is used instead of ethanol as reaction medium.

$C_{28}H_{36}N_6O_2$ (488.6) Calc.: C 68.83 H 7.43 N 17.20. Found: C 69.07 H 7.61 N 17.29.

MS: m/z (rel. Int. [%])=488 (M$^+$, 11), 105 (100, 95 (33), 84 (57), 77 (75).

$^1$H-NMR data (d$_6$-DMSO, TMS as internal standard): δ=1.15–1.85 (m) 6 H, 2.00 (m) 2 H, 2.28 (m) 4 H, 2.77 (t) 2 H, 3.32 (s) 2 H, 3.0–3.8 (m) 4 H, 4.00 (t) 2 H, 6.55–7.55 (m) 9 H, 8.02 (m) 2 H, ppm.

EXAMPLE 2

N-Benzoyl-N'-[2-(5-methylimidazol-4-yl)ethyl]-N''-[3-(3-piperidinomethyl-phenoxy)propyl]guanidine

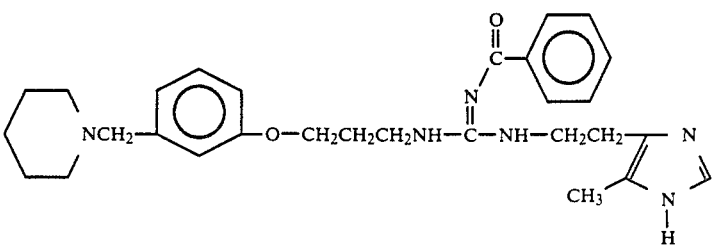

5 mmol of 5-Methylhistamine prepared from 0.99 g of the dihydrochloride with 10 mmol of sodium ethylate in ethanol are heated under reflux with 2.36 g (5 mmol) of N-benzoyl-O-phenyl-N'-[3-(3-piperidinomethyl-phenoxy) propyl] isourea (Example 1b) in 20 ml of acetonitrile for one hour. After concentration of the reaction mixture by evaporation under vacuum, the reaction product is isolated by preparative layer chromatography (silica gel 60 PF$_{254}$ containing gypsum, solvent: ethyl acetate/methanolic ammonia 90+10). The eluate is concentrated by evaporation under vacuum and the residue is dissolved in a small quantity of acetonitrile, and ethyl acetate is added. 0.25 g (10%) of N-benzoyl-N'-[2-(5-methylimidazol-4-yl)ethyl]-N''-[3-(3-piperidinomethyl-phenoxy) propyl]guanidine, melting point 118° to 120° C., crystallises when the solution is kept in a refrigerator (−20° C.).

$C_{29}H_{38}N_6O_2$ (502.7) Calc.: C 69.29 H 7.62 N 16.72. Found: C 69.07 H 7.77 N 16.61.

MS: m/z (rel. Int. [%])=502 (M+, 1), 109 (6), 105 (8), 95 (25), 84 (42), 77 (7), 44 (100).

$^1$H-NMR data (d$_6$-DMSO, TMS as internal standard): δ=1.15–1.7 (m) 6 H, 2.00 (m) 2 H, 2.10 (s) 3 H, 2.27 (m) 4 H. 2.70 (t) 2 H, 3.33 (s) 2 H, 3.0–3.8 (m) 4 H, 4.00 (t) 2 H, 6.55–7.6 (m) 8 H, 8.02 (m) 2 H, ppm.

EXAMPLE 3

N-Benzoyl-N'-[3-(imidazol-4-yl)propyl]-N''-[3-(3-piperidinomethylphenoxy)propyl]guanidine raphy (see Example 2). When the eluate has been concentrated by evaporation under vacuum, it is dissolved in hot acetonitrile and then left to stand to crystallise.

Yield: 1,4 g (56%) of colourless needles, melting point 115° C.

$C_{29}H_{38}N_6O_2$ (502.7) Calc.: C 69.29 H 7.62 N 16.72. Found: C 69.47 H 7.72 N 16.76.

MS: m/z (rel. Int. [%])=502 (M+, 24), 109 (50), 105 (100), 84 (25), 77 (39).

IR (KBr): 1600 (C=O)cm$^1$.

$^1$H-NMR data (d$_6$-DMSO, TMS as internal standard): δ=1.15–2.4 (m) 14 H, 2.58 (t) 2 H, 3.32 (s) 2 H, 2.75–3.8 (m) 4 H, 4.03 (t) 2 H, 6.55–7.55 (m) 9 H, 8.06 (m) 2 H, ppm.

EXAMPLE 4

N-[3-(Imidazol-4-yl)propyl]-N'-[3-(3-piperidinomethyl-phenoxy)propyl]guanidine

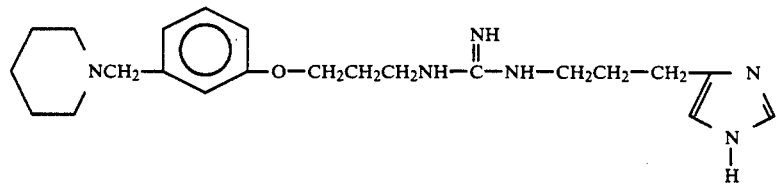

0.90 g (1.79 mmol) of N-benzoyl-N'-3-(imidazol-4-yl)propyl]-N''-[3-(3-piperidinomethyl-phenoxy)propyl]-guanidine (Example 3) are heated under reflux in 45 ml of 20% hydrochloric acid for 7 hours. When the reaction mixture has cooled, the precipitated benzoic acid is filtered off, the filtrate is extracted three times with ether and the aqueous phase is evaporated to dryness under vacuum. 0.8 g (88%) of dry foam is obtained. $C_{22}H_{34}N_6O \times 3$ HCl (507.9)

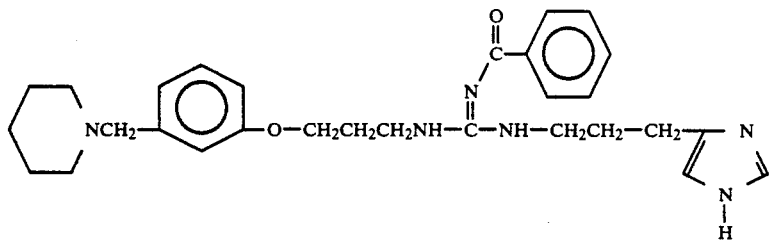

The base is released from 0.99 g (5 mmol) of 3-(imidazol-4-yl)propylamine dihydrochloride by means of 10 mmol of sodium ethylate in ethanol, the precipitated sodium chloride is filtered off and the filtrate is concentrated by evaporation under vacuum and taken up with pyridine. After the addition of 2.36 (5 mmol) of N-benzoyl-O-phenyl-N'-[3-(3-piperidinomethyl-phenoxy) propyl]isourea (Example 1, preparation b) the reaction mixture is heated under reflux for one hour and then concentrated by evaporation under vacuum and the product is isolated by preparative layer chromatog- MS: m/z (rel. Int. [%])=398 (M+, 3), 109 (39), 95 (50), 84 (67)

$^1$H-NMR data (d$_6$-DMSO, TMS as internal standard): δ=1.3–2.3 (m) 8 H, 2.4–3.65 (m) 12 H, 4.08 (t) 2 H, 4.18 (s) 2 H, 6.8–7.5 (m) 5 H, 7.6 (s, broad) 2 H, replaceable by D$_2$O, 7.75–8.25 (m) 2 H, replaceable by D$_2$O, 8.93 (d) 1 H, ppm.

EXAMPLE 5

N-[2-(Imidazol-4-yl)ethyl]-N'-[3-(3-piperidinomethyl-phenoxy)propyl]-guanidine

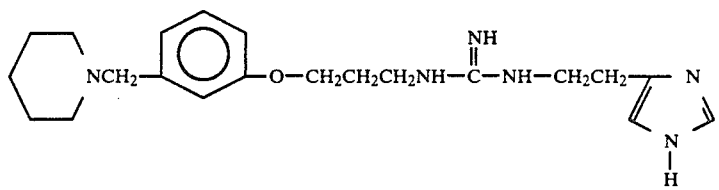

1.4 g (3,4 mmol) of N-cyano-N'-(2-(imidazol-4-yl)ethyl]-N''-[3-(3-piperidinomethyl-phenoxy)propyl]-guanidine are heated under reflux with 50 ml of concentrated hydrochloric acid for 4 hours. The reaction mixture is then evaporated to dryness under vacuum and the residue is extracted three times by stirring with anhydrous acetone. The combined extracts are concentrated by evaporation under vacuum to yield 1.5 g (89%) of the highly hygroscopic trihydrochloride, which sinters at 100° C. The tripicrate sinters at 95° to 100° C.

$C_{21}H_{32}N_6O \times 3 \ C_6H_3N_37$ (1071.8).

Calc.: C 43.70 H 3.86 N 19.60. Found: C 43.65 H 3.71 N 19.43.

$C_{21}H_{32}N_6O \times 3$ HCl (493.9)

MS: m/z (rel. Int. [%]) = 384 (M+, 40), 302 (82), 107 (100), 95 (21), 84 (98).

$^1$H-NMR data (d$_6$-DMSO, H-D exchange with CF$_3$COOD; TMS as internal standard): $\delta = 1.2-2.4$ (m) 8 H, 2.6–3.9 (m) 10 H, 4.13 (t) 2 H, 4.27 (s) 2 H, 6.85–7.7 (m) 5 H, 9.00(d) 1 H, ppm.

EXAMPLE 6

N-Benzoyl-N'-[2-hydroxy-3-(3-piperidinomethyl-phenoxy) propyl]-N''-[3-(imidazol-4-yl)propyl]guanidine uct is then isolated by preparative layer chromatography (silica gel 60 PF$_{254}$ containing gypsum, solvent: chloroform/methanol.ammonia, 94+6). After concentration of the eluate by evaporation, 0.62 g (24%) of colourless crystals, melting point 75° to 77° C., are obtained by crystallisation from ethyl acetate.

$C_{29}H_{38}N_6O_3$ (518.7). Calc: C 67.16 H 7.39 N 16.20. Found: C 66.89 H 7.50 N 15.91.

$^1$H-NMR data (d$_6$-DMSO, TMS as internal standard): $\delta = 1.15-1.7$ (m) 6 H, 1.83 (m) 2 H, 2.27 (m) 4 H, 2.57 (m) 2 H, 3.32 (s) 2 H, 2.9–3.8 (m) 4 H, 3.95 (m) 3 H. 5.5 (m) 1 H, replaceable by D$_2$O, 6.5–7.5 (m) 11 H, 2 H replaceable by D$_2$O, 8.03 (m) 2 H, 10.2 (m, broad) 1 H, replaceable D$_2$O, ppm.

Method B

Preparation of the preliminary stage

2-Benzoylimino-5-[(3-piperidinomethyl-phenoxy)methyl]oxazolidine

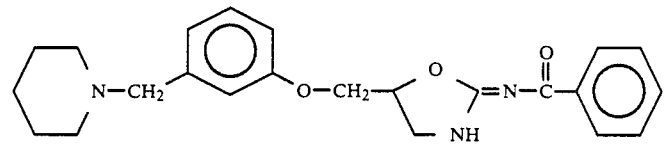

2.64 g (10 mmol) of 2-hydroxy-3-(3-piperidinomethylphenoxy)propylamine in 10 ml of methylene chloride are introduced dropwise at 0°–10° C. into a solution of 2.02 g (10 mmol) of benzoyl isocyanide dichloride in 20 ml of methylene chloride. After dropwise addition of a mixture of 1.5 ml of triethylamine and 10 ml of methylene chloride, the reaction mixture is stirred for 30 minutes and the triethylammonium chloride formed is then removed by washing with water, and the organic phase is dehydrated over sodium sulphate and concentrated by evaporation under vacuum. The residue is recrystal-

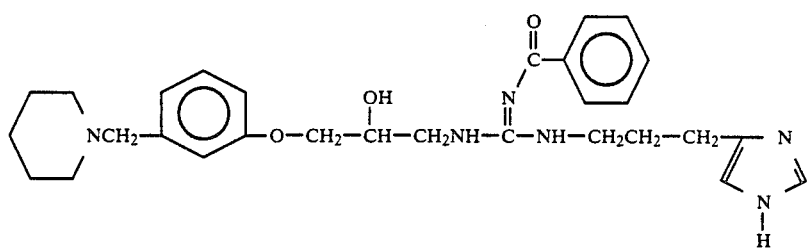

Method A 1.32 g (5 mmol) of 2-hydroxy-3-(3-piperidinomethyl phenoxy)propylamine and 1.59 g (5 mmol) of N-benzoyldiphenylimidocarbonate are stirred together at room temperature in 30 ml of acetonitrile for 40 minutes. After the addition of 0.63 g (5 mmol) of 3-(imidazol-4-yl)propylamine, the reaction mixture is heated under reflux for one hour and the reaction prodlised from methanol.

Yield: 3.5 g (89%) of colourless needles, melting point 126° C.

$C_{23}H_{27}N_3O_3$ (393.5). Calc.: C 70.21 H 6.92 N 10.68. Found: C 70.16 H 6.97 N 10.81.

$^1$H-NMR data (d$_6$-DMSO, TMS as internal standard): $\delta = 1.38$ (m) 2 H, 1.48 (m) 4 H, 2.30 (m) 4 H, 3.38 (s) 2 H, 3.69 (dd) 1 H, 3.95 (dd) 1 H, 4.20 (dd) 1 H, 4.29

(dd) 1 H, 5.13 (m) 1 H, 6.8–7.0 (m) 3 H, 7.24 (m) 1 H, 7.4–7.6 (m) 3 H, 8.09 (m) 2 H, 9.67 (s) 1 H, replaceable by $D_2O$, ppm.

N-Benzoyl-N'-[2-hydroxy-3-(3-piperidinomethyl-phenoxy)propyl]-N''-[3-(imidazol-4-yl)propyl]guanidine 1.97 g (5 mmol) of 2-benzoylimino-5-[(3-piperidinomethylphenoxy)methyl]oxazolidine and 0.69 g (5.5 mmol) of 3-(imidazol-4-yl)propylamine are together heated under reflux in 30 ml of pyridine for 8 hours. The solvent is distilled off under vacuum, and the reaction product is isolated and purified by a method analogous to Method A.

Yield: 1.1 g (42%).

EXAMPLE 7

N-[2-Hydroxy-3-(3-piperidinomethyl-phenoxy)propyl]-N'-[3-(imidazol-4-yl)-propyl]guanidine

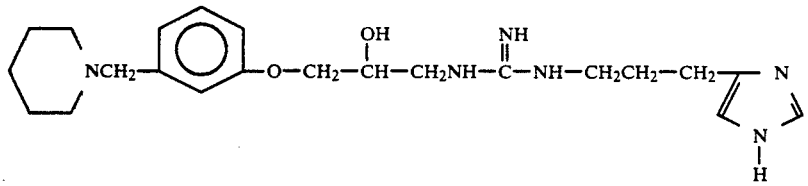

0.4 g (0.77 mmol) of N-benzoyl-N'-2-hydroxy-3-(piperidinomethyl-phenoxy)-propyl]-N''-[3-(imidazol-4-yl)propyl]guanidine (Example 6) are heated under reflux in 45 ml of 15% hydrochloric acid for 6 hours. The reaction mixture, is worked up by a method analogous to that of Example 4. After concentration of the aqueous solution by evaporation, the residue is crystallised from isopropyl alcohol/ether. After drying under vacuum at room temperature, 0.42 g (93%) of the hygroscopic trihydrochloride which contains 1 mol of isopropyl alcohol and sinters at 75° C. is obtained $C_{22}H_{34}N_6O_2 \times 3$ HCl$\times C_3H_8O$ (584.0)

MS (FAB method): m/z (rel. Int. [%])=415 ([M+H]+, 91), 331 (13, 265 (22), 192 (37), 109 (100), 84 (87). $^1$H-NMR data (d$_6$-DMSO, TMS as internal standard): $\delta=1.03$ (d) 6 H, isopropyl alcohol 1.15–2.2 (m) 8 H, 2.3–4.3 (m) 16 H, 5.6 (m, broad) 2 H, replaceable by $D_2O$, 6.7–8.1 (m) 8 H. 3 H replaceable by $D_2O$, 8.96 (d) 1 H ppm.

EXAMPLE 8

$N^1$-[3-[N-(5-methyl-pyrid-2-yl)-methylamino]propyl]-$N^2$-[2-(1H-imidazol-4-yl)ethyl]guanidine trihydrochloride Preparation of the preliminary stages a) O-Phenyl-$N^1$-cyano-$N^2$-[3-[N-(5-methyl-pyrid-2-yl)-methylamino]propyl]-isourea 3.60 g (20 mmol) of N-methyl-N-(5-methyl-pyrid-2-yl)-propane-1,3-diamine and 4.76 g (20 mmol) of diphenylcyanoimidocarbonate are stirred up in 30 ml of i-propanol for 4 hours at room temperature. After removal of the solvent by evaporation under vacuum, the residue is taken up with 200 ml of methylene chloride and extracted twice with 100 ml of 1 N sodium hydroxide solution. After dehydration over sodium sulphate, the organic phase is concentrated by evaporation under vacuum. The oil obtained crystallises after a short time to colourless crystals melting at 185° C. (decomposition).

Yield: 4.19 g (65%)
$C_{18}H_{21}N_5O$ (323.4).
Rf: 0.45 ($CH_2Cl_2CH_3OH$ 98:2).

b) $N^1$-Cyano-$N^2$-[3-[N-(5-methyl-pyrid-2-yl)-methylamino]propyl]-N3-[2-(1H-imidazol-4-yl)ethyl]-guanidine

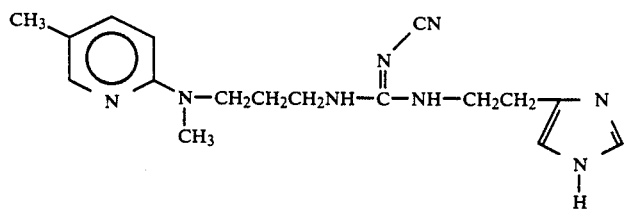

3.00 g (9.3 mmol) of O-phenyl-N'-cyano-N'-[3-[N-(5-methyl-pyrid-2-yl)-methylamino]propyl]-isourea and 1.03 g (9.3 mmol) of histamine are boiled under reflux in 60 ml of i-propanol for 10 hours. After removal of the solvent by evaporation under vacuum, the residue is chromatographed with ethyl acetate/ethanol (60:40) on silica gel. The main fraction yields 1.76 g (56%) of the title compound after evaporation of the solvent. Colourless solid, melting point 152°–153° C. (from chloroform).

$C_{17}H_{24}N_8$ (340.4)
Rf: 0.41 (EtOAc/EtOH 60:40)
$^1$H-NMR data (CD$_3$OD, TMS as internal standard): $\delta=1.73$ (m) 2 H, 2.16 (s) 3 H, 2.84 (t) 2 H, 2.96 (s) 3 H, 3.18 (t) 2 H, 3.36–3.69 (m) 4 H, 5.0 (broad) 3 H, 6.56 (d) 1 H, 6.90 (s) 1 H, 7.37 (dd) 1 H, 7.64 (s) 1 H, 7.99 (d) 1 H ppm.

$N^1$[3-[N-(5-Methyl-pyrid-2-yl)-methylamino]propyl]-$N^2$-[2-(1H-imidazol-4-yl)ethyl]guanidine trihydrochloride

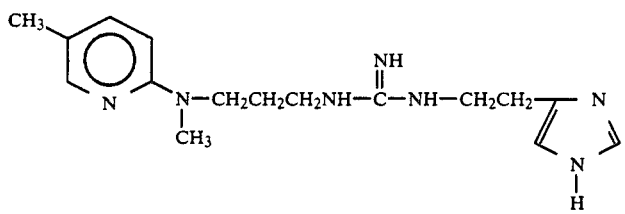

2.0 g (5.9 mmol) of $N^1$-Cyano-$N^2$-[3-[N-(5-methyl-pyrid-2-yl)-methylamino]propyl-$N^3$-[2-(1H-imidazol-4-yl)ethyl]guanidine are boiled in 20 ml of 4 N hydrochloric acid for 9 hours. The solution is concentrated by evaporation under vacuum and the residue is taken up with 10 ml of methanol and stirred up with 3.3 ml of 5.5 N sodium methylate solution for 10 minutes. After removal of the precipitate by suction filtration, the filtrate is again concentrated by evaporation under vacuum. The crude product obtained is purified with ethyl acetate/methanol (1:1) on aluminium oxide (neutral). After concentration by evaporation, the main fraction yields 0.88 g of a colourless oil, which is dissolved in 20 ml of water. After the addition of 6.1 ml of 2 N hydrochloric acid, the solution is concentrated by evaporation under vacuum and the residue is dried in a high vacuum. 1.16 g (47%) of the title compound is obtained as a colourless, hygroscopic solid.

$C_{16}H_{28}Cl_3N_7$ (424.8)

Rf: 0.2 (base, alox, EtOAc/MeOH 1:1)

$^1$H-NMR data (CD$_3$OD, TMS as internal standard): $\delta$=2.01 (m) 2 H, 2.29 (s) 3 H, 3.10 (t) 2 H, 3.34 (s) 3 H, 3.40 (t) 2 H, 3.52-3.94 (m) 4 H, 4.8 (broad) 7 H, 7.38 (d) 1 H, 7.60 (s) 1 H, 7.86 (d) 1 H, 7.99 (dd) 1 H, 9.0 (s) 1 H, ppm.

EXAMPLE 9

$N^1$-Benzoyl-$N^2$-[3-[N-(5-methyl-pyridin-2-yl)-methylamino]propyl]-$N_2$-3-(1H-imidazol-4-yl)propyl]-guanidine

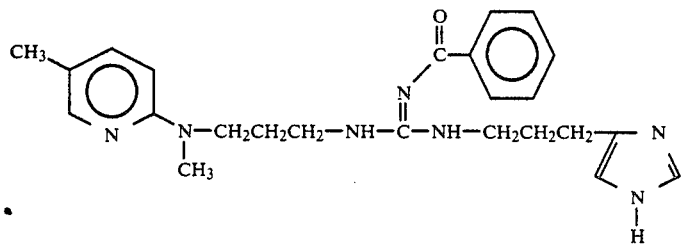

3.48 g (10 mmol) of $N^1$-benzoyl-$N^2$-[3-(4-imidazolyl)propyl]-O-phenyl-isourea and 1.79 g (10 mmol) of N-methyl-N-(5-methyl-pyridin-2-yl)-1,3-propanediamine are boiled under reflux in 50 ml of ethanol for 20 hours. The residue obtained after evaporation of the solvent is chromatographed with ethyl acetate/ethanol (80:20) on silica gel. The main fraction yields 3.76 g (76%) of a pale yellow oil after removal of the solvent by evaporation.

$^1$H-NMR data (CD$_3$OD, TMS as internal standard): $\delta$=1.71-2.20 (m) 4 H, 2.17 (s) 3 H, 2.77 (t) 2 H, 3.07 (s) 3 H, 3.35-3.61 (m) 4 H, 3.71 (t) 2 H, 5.0 (broad) 3 H, 6.80 (d) 1 H, 7.10 (s) 1 H, 7.50-7.82 (m) 4 H, 7.86 (s) 1 H, 8.18 (d) 1 H, 8.39-8.53 (m) 2 H ppm.

EXAMPLE 10

$N^1$-[3-[N-(5-Methyl-pyridin-2-yl)-methylamino]-propyl]-$N^2$-[3-(1H-imidazol-4-yl)propyl]guanidine trihydrochloride

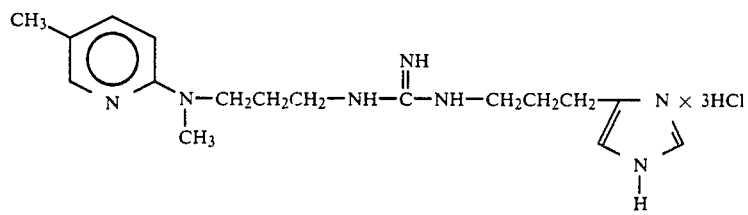

1.41 g of a brown solid are obtained from 1.38 g (3.2 mmol) of $N^1$-benzoyl-$N^2$-[3-[(N-5-methyl-pyridin-2-yl)methylamino]propyl]-$N^2$-[3-(1H-imidazol-4-yl)propyl]guanidine (Example 9) and 20 ml of conc. hydrochloric acid. After conversion of the product into the base, it is purified chromatographically on aluminium oxide, using ethyl acetate/methanol (1:1) as solvent. Conversion of the product back into a trihydrochloride yields 0.64 g (46%) of a colourless, amorphous hygroscopic solid.

$C_{17}H_{30}Cl_3N_7$ (438.83)

$^1$H-NMR data (CD$_3$OD, TMS as internal standard): $\delta$=1.82-2.23 (m) 4 H, 2.29 (s) 3 H, 2.89 (t) 2 H, 3.20-3.55 (m) 4 H, 3.30 (s) 3 H, 3.80 (t) 2 H, 4.8 (broad) 7 H, 7.36 (d) 1 H, 7.48 (s) 1 H, 7.84 (m) 1 H, 7.99 (dd) 1 H, 8.92 (d) 1 H, ppm.

EXAMPLE 11

N$^1$-Benzoyl-N$^2$-[4-(pyridin-3-yl)butyl]-N$^3$-[3-(1H-imidazol-4-yl)propyl]-guanidine

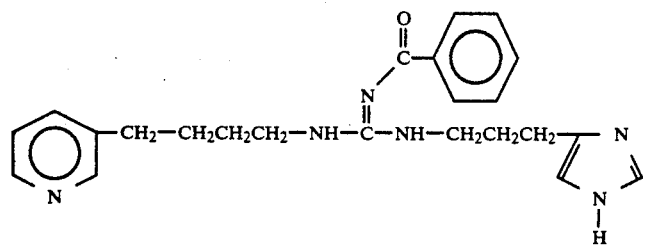

3.48 g (10 mmol) of N$^1$-benzoyl-N$^2$-[3-(4-imidazolyl)propyl]-O-phenyl-isourea and 1.50 g (10 mmol) of 3-(4-amino butyl)-pyridine are reacted together in 50 ml of ethanol by a method analogous to that of Example 9. After purification of the crude product on silica gel with ethyl acetate/ethanol (80:20), the solid obtained is recrystallised from ethyl acetate. 2.54 g (63%) of colourless crystals, melting point 119.0° to 120.1° C.

C$_{23}$H$_{28}$N$_6$O (404.51)

$^1$H-NMR data (CDCl$_3$, TMS as internal standard): δ=1.50–2.10 (m) 6 H, 2.50–2.82 (m) 4 H, 3.29–3.71 (m) 4 H, 6.89 (s) 1 H, 7.22–7.73 (m) 7 H, 1 H replaceable by D$_2$O, 8.29–8.50 (m) 2 H, 8.61 (d) 2 H, 9.5 (broad) 1 H, replaceable by D$_2$O, ppm.

EXAMPLE 12

N$^1$-[4-(Pyridin-3-yl)butyl]-N$^2$-[3-(1H-imidazol-4-yl)propyl]guanidine trihydrochloride

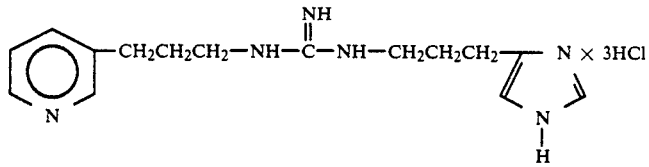

0.89 g (97%) of a colourless, highly hygroscopic foam are obtained by a method analogous to that of Example 10 from 0.90 g (2.2 mmol) of N$^1$-benzoyl-N$^2$-[4-(pyridin-3-yl)butyl]-N$^3$-[3-(1H-imidazol-4-yl)propyl]-guanidine and 15 ml of conc. hydrochloric acid C$_{16}$H$_{27}$Cl$_3$N$_6$ (409.79)

$^1$H-NMR data (CD$_3$OD, TMS as internal standard): δ=1.53–2.19 (m) 6 H, 2.69–3.08 (m) 4 H, 3.13–3.41 (m) 4 H, 4.85 (broad) 7 H, 7.39 (s) 1 H, 7.94–8.16 (m) 1 H, 8.52–8.93 (m) 4 H ppm.

EXAMPLE 13

N$^1$-[3-(Pyridin-3-yl)propyl]-N$^2$-[3-(1H-imidazol-4-yl)propyl]guanidine trihydrochloride

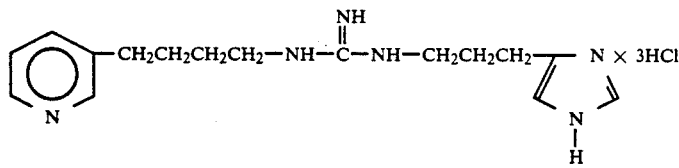

0.80 g (96%) of a colourless, hygroscopic foam are obtained by a method analogous to that of Example 10 from 0.9 g (2.4 mmol) of N$^1$-benzoyl-N$^2$-[3-(pyridin-3-yl)propyl]-N$^3$-[3-(1H-imidazol-4-yl)propyl]-guanidine and 15 ml of conc. hydrochloric acid.

C$_{15}$H$_{25}$Cl$_3$N$_6$ (395.79)

$^1$H-NMR data (CD$_3$OD, TMS as internal standard): δ=1.53–2.20 (m) 4 H, 2.69–3.08 (m) 4 H, 3.1–3.4 (m) 4 H, 4.85 (broad) 7 H, 7.39 (s) 1 H, 7.94–8.16 (m) 1 H, 8.52–8.93 (m) 4 H ppm.

EXAMPLE 14

N$^1$-Benzoyl-N$^2$-[4-(3-methoxy-pyridin-2-yl)butyl]-N$^3$-[3-(1H-imidazol-4-yl)propyl]-guanidine

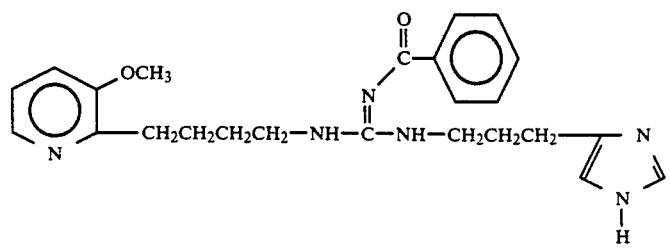

3.48 g (10 mmol) of N$^1$-benzoyl-N$^2$-[3-(4-imidazolyl)propyl]-O-phenyl-isourea and 1.80 g (10 mmol) of 2-(4- aminobutyl)—3-methoxypyridine are boiled under reflux in 50 ml of ethanol for 20 hours. The residue obtained after evaporation of the solvent is chromatographed on silica gel with ethyl acetate/ethanol (80:20).

EXAMPLE 16

$N^1$-Benzoyl-$N^2$-[4-(5-bromo-3-methyl-pyridin-2-yl)butyl]-$N^3$-[3-(1H-imidazol-4-yl)propyl]guanidine

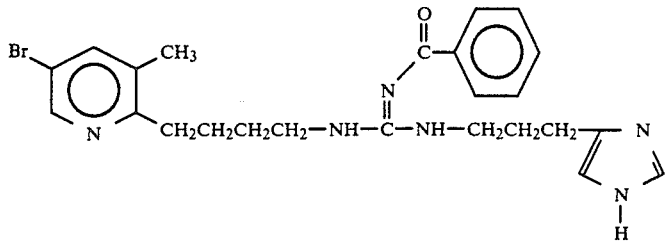

After evaporation of the solvent, the main fraction yields 3.67 g (84%) of the benzoylguanidine as a colourless oil.

$C_{24}H_{30}N_6O_2$ (434.35)

$^1$H-NMR data (CD$_3$OD, TMS as internal standard: δ = 1.55–1.84 (m) 4 H, 1.92 (quin) 2 H. 2.67 (t) 2 H, 2.84 (t) 2 H, 3.23–3.50 (m) 4 H, 3.86 (s) 3 H. 4.85 (broad) 3 H, 6.87 (s) 1 H, 7.12–7.50 (m) 5 H, 7.60 (s) 1 H, 7.96–8.21 (m) 3 H, ppm.

EXAMPLE 15

$N^1$-[4-(3-Methoxy-pyridin-2-yl)butyl]-$N^2$-[3-(1H-imidazol-4-yl)propyl]guanidine trihydrochloride

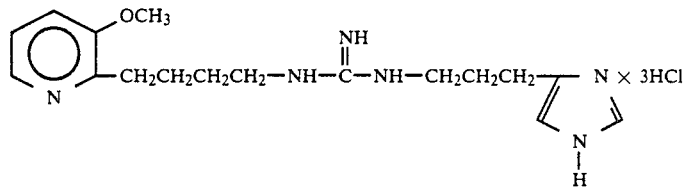

0.75 g (1.7 mmol) of $N^1$-benzoyl-$N^2$-[4-(3-methoxy-pyridin-2-yl)butyl]-$N^3$-[3-(1H-imidazol-4-yl)propyl]-guanidine and 15 ml of conc. hydrochloric acid are boiled under reflux for 18 hours. After cooling, the reaction mixture is diluted to 30 ml with water and extracted with 4×25 ml diethylether. The aqueous phase is then filtered and concentrated by evaporation under vacuum. The residue is taken up twice with 20 ml of absolute ethanol and again concentrated by evaporation. 0.74 g (98%) of a colourless, amorphous, highly hygroscopic solid is obtained.

$C_{17}H_{29}Cl_3N_6O$ (439.81)

$^1$H-NMR data (CD$_3$OD, TMS as internal standard): δ = 1.57–2.25 (m) 6 H, 2.89 (t) 2 H, 3.02–3.48 (m) 6 H, 4.12 (s) 3 H, 4.8 (broad) 7 H, 7.47 (s) 1 H, 7.88–8.45 (m) 3 H, 8.90 (d) 1 H, ppm.

A mixture of 3.48 g (10 mmol) of $N^1$-benzoyl-$N^2$-[3-(4-imidazolyl)propyl]-O-phenyl-isourea and 2.43 g (10 mmol) of 2-(4-aminobutyl)-5-bromo-3-methyl-pyridine in 50 ml of ethanol is boiled for 18 hours. The oil obtained after concentration of the reaction mixture by evaporation is purified on silica gel, using ethyl acetate/ethanol (80:20) as solvent. After evaporation of the solvent, the main fraction yields a colourless solid which is recrystallised from ethyl acetate. 2.48 g (50%) of colourless crystals melting at 126.5°–127.8° C. are obtained.

$C_{24}H_{29}BrN_6O$ (497.44)

$^1$H-NMR data (CD$_3$OD, TMS as internal standard): δ = 1.60–2.19 (m) 6 H, 2.32 (s) 3 H, 2.62–3.00 (m) 4 H, 3.45–3.67 (m) 4 H, 5.0 (broad) 3 H, 7.04 (s) 1 H, 7.47–7.70 (m) 3 H, 7.80 (s) 1 H, 7.95 (d) 1 H, 8.38–8.49 (m) 2 H, 8.61 (d) 1 H, ppm.

EXAMPLE 17

$N^1$-[4-(5-Bromo-3-methyl-pyridin-2-yl)butyl]-$N^2$[3-(1H-imidazol-4-yl)propyl]-guanidine trihydrochloride

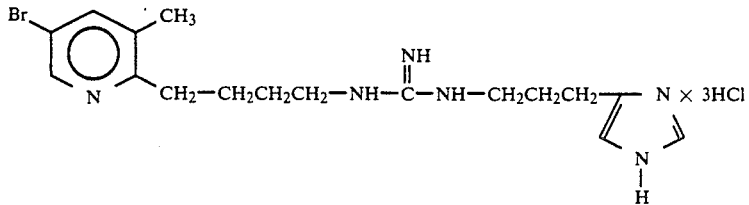

1.00 g (2 mmol) of $N^1$-Benzoyl-$N^2$-[4-(5-bromo-3-methyl-pyridin-2-yl)butyl]-$N^3$-[3-(1H-imidazol-4-yl)propyl]-guanidine is boiled in 20 ml of conc. hydrochloric acid for 18 hours. The aqueous solution diluted to 40 ml after cooling is extracted with 4×20 ml of diethylether, filtered and concentrated by evaporation under vacuum. The residue is taken up twice with 20 ml of absolute ethanol and concentrated by evaporation. The crude product obtained is then converted into the base with sodium methylate and chromatographed on aluminium oxide with ethyl acetate/ methanol (1:1).

After concentration by evaporation, the main fraction is taken up with 5 ml of water, 0.5 ml of conc. hydrochloric acid is added, and the mixture is concentrated by evaporation under vacuum. After the mixture has again been concentrated by evaporation with 20 ml of absolute ethanol, 0.62 g (60%) of the title compound is obtained, in the form of a colourless, hygroscopic solid.

$C_{17}H_{28}BrCl_3N_6$ (502.71)

$^1$H-NMR data (CD$_3$OD, TMS as internal standard:
δ = 1.68–2.22 (m) 6 H, 2.61 (s) 3 H, 2.91 (t) 2 H, 3.05–3.52 (m) 6 H, 4.95 (broad) 7 H, 7.61 (s) 1 H, 8.89 (d) 1 H, 9.10 (d) 2 H, ppm.

EXAMPLE 18

$N^1$-[3-(5-Bromo-3-methyl-pyridin-2-yl)propyl]-$N^2$-[3-(1H-imidazol-4-yl)propyl]-guanidine trihydrochloride

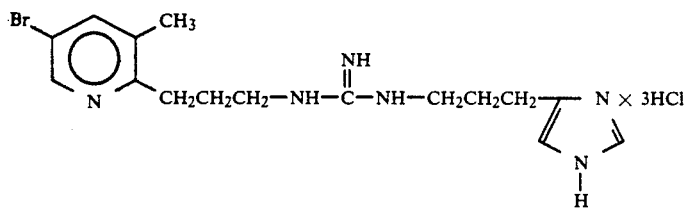

The compound is prepared by a method analogous to that of Example 17 from $N^1$-benzoyl-$N^2$-[3-(5-bromo-3-methyl-pyridin-2-yl)propyl]-$N^3$-[3-(1H-imidazol-4-yl)propyl-guanidine in conc. hydrochloric acid.

Colourless, hygroscopic solid.

$C_{16}H_{26}BrCl_3N_6$ (488.68)

$^1$H-NMR data (CD$_3$OD, TMS as internal standard):
δ = 1.68–2.22 (m) 4 H, 2.61 (s) 3 H, 2.87 (t) 2 H, 3.05–3.52 (m) 6 H, 4.95 (broad) 7 H, 7.48 (s) 1 H, 8.83 (d) 1 H, 8.93 (d) 2 H, ppm.

EXAMPLE 19

$N^1$-Benzoyl-$N^2$-[3-(1H-imidazol-4-yl)propyl]-$N^3$-[2-(pyridin-2-ylamino)ethyl]-guanidine

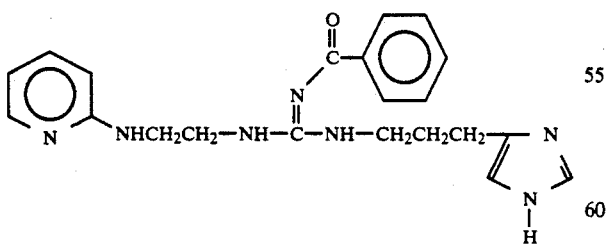

1.50 g (76%) of the benzoyl guanidine are obtained in the form of a colourless oil by a method analogous to that of Example 16 from 0.69 g (5 mmol) of N-(2-pyridin-yl)-ethylenediamine and 1.74 g (5 mmol) of $N^1$-benzoyl-$N^2$-[3-(1H-imidazol-4-yl)propyl]-O-phenyl-isourea after 24 hours' boiling in 30 ml of ethanol and chromatographic purification of the crude product (silica gel, ethyl acetate/ethanol 80:20).

$C_{21}H_{25}N_7O$ (391.47)

$^1$H-NMR data (CD$_3$OD, TMS as internal standard):
δ = 1.77–2.12 (m) 2 H, 2.65 (t) 2 H, 3.29 (t) 2 H, 3.46–3.89 (m) 4 H, 4.85 (broad) 4 H, replaceable by D$_2$O, 6.45–7.62 (m) 8 H, 7.98–8.30 (m) 3 H, ppm.

EXAMPLE 20

$N^1$-[3-(1H-Imidazol-4-yl)propyl]-$N^2$-[2-(pyridin-2-yl-amino)ethyl]-guanidine trihydrochloride

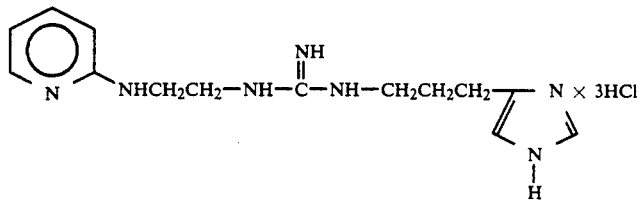

0.93 g (76%) of a colourless, hygroscopic solid is obtained by a method analogous to that of Example 17 from 1.21 g (3.1 mmol) of $N^1$-benzoyl-$N^2$-[3-(1H-imidazol-4-yl)propyl]-$N^3$-[2-(pyridin-2-yl-amino)ethyl]-guanidine and 20 ml of conc. hydrochloric acid.

$C_{14}H_{24}Cl_3N_7$ (396.75)

$^1$H-NMR data (CD$_3$OD, TMS as internal standard):
δ = 1.80–2.21 (m) 2 H, 2.69–3.00 (m) 2 H, 3.37 (t) 2 H, 3.57–3.83 (m) 4 H, 4.8 (broad) 8 H replaceable by D$_2$O, 6.96 (t) 1H, 7.22 (d) 1 H, 7.44 (s) 1 H, 7.83–8.16 (m) 2 H, 8.87 (s) 1 H, ppm.

EXAMPLE 21

$N^1$-[2-(1H-Imidazol-4-yl)ethyl]-$N^2$-[2-[[(5-methylthio-1H-imidazol-4-yl)methyl]thio]ethyl]guanidine trihydrochloride Preparation of the preliminary stages a) O-Phenyl-$N^1$-cyano-$N^2$-[2-[[(5-methylthio-1H-imidazol-4-yl) methyl]thio]ethyl]-isourea

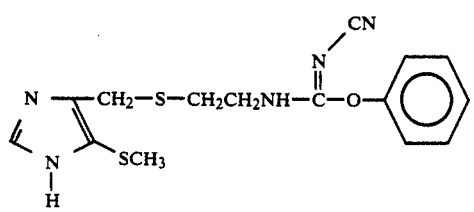

5.50 g (20 mmol) of 2-[5-methylthio-1H-imidazol-4-yl] methylthio]ethylamine dihydrochloride are added to a solution of 0.92 g (40 mmol) of sodium in 60 ml of anhydrous ethanol. The precipitate formed is suction filtered after 30 minutes' stirring.

4.76 g (20 mmol) of diphenylcyano-imidocarbonate in 10 ml of ethanol are added to the filtrate with ice cooling and the mixture is stirred at room temperature for 3 hours. The solution is concentrated by evaporation and the residue is freed from residues of solvent in a high vacuum. The oil obtained crystallises after brief stirring with 150 ml of methylene chloride.

Yield: 5.77 g (83%)

Colourless crystals, melting point 158°–159° C.

$C_{15}H_{17}N_5OS_2$ (347.5)

Rf ($CH_3OH/N (C_2H_5)_3$ 97:3): 0.76

$^1$H-NMR data ($d_6$-DMSO, TMS as internal standard): δ=2.24 (s) 3 H, 2.57–2.89 (m) 2 H, 3.31–3.68 (m) 2 H, 3.75 (s) 2 H, 7.12–7.58 (m) 5 H, 7.63 (s) 1 H, 8.9 (broad) 1 H, replaceable by $D_2O$, ppm.

b) $N^1$-Cyano-$N^2$-[2-(1H-imidazol-4-yl)ethyl]-$N^3$-[2-[[(5methylthio-1H-imidazol-4-yl)methyl]-thio]ethyl]-guanidine

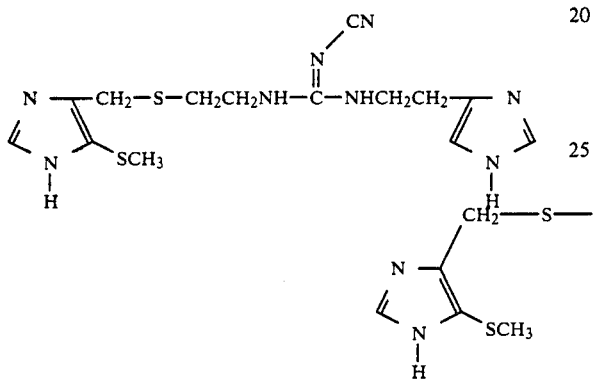

2.68 g (7.7 mmol)(O-phenyl-$N^1$-cyano-$N^2$-2-[[(5-methyl-thio-1H-imidazol-4-yl)methyl]thio]ethyl]-isourea and 0.86 g (7.7 mmol) of histamine are stirred in 40 ml of i-propanol at 70° C. for 8 hours. After concentration of the solution by evaporation under vacuum, the residue is chromatographed on silica gel with ethyl acetate/ethanol (60:40). After concentration by evaporation, the main fraction yields 1.86 g (71%) of the title compound in the form of a colourless, amorphous solid. Melting point 80°82° C.

$C_{14}H_{20}N_8S_2$ (364.5)

Rf (EtOAc/EtOH 60:40): 0.42

$^1$H-NMR data ($CD_3OD$, TMS as internal standard): δ=2.32 (s) 3 H, 2.68 (t) 2 H, 2.88 (t) 2 H, 3.32–3.63 (m) 4 H, 3.84 (s) 2 H, 5.46 (broad) 4 H, 6.95 (s) 1 H, 7.68 (s) 1 H, 7.71 (s) 1 H, ppm.

$N^1$-[2-(1H-Imidazol-4-yl)ethyl]-$N^2$-[2-[[(5-methylthio-1H-imidazol-4-yl)methyl]thio]ethyl]guanidine trihydrochloride

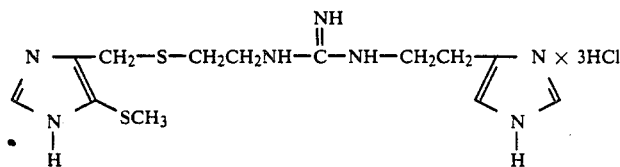

1.82 g (5.0 mmol) of $N^1$-Cyano-$N^2$-[2-(1H-imidazol-4-yl) ethyl]-$N^3$-[2-[[(5-methylthio-1H-imidazol-4-yl)methyl]thio]ethyl]guanidine are boiled for 14 hours in 20 ml of 4N-hydrochloric acid. After concentration of the reaction mixture by evaporation, the residue is dissolved in 12 ml of methanol. 4 ml of 5.5 N sodium methylate solution are then added and the mixture is stirred for 10 minutes. After removal of the precipitate by suction filtration, 3.6 g (15 mmol) of picric acid in 50 ml of methanol are added to the filtrate which is then briefly boiled up. After repeated decanting to remove resinous impurities, 1.07 g of the tripicrate of the title compound crystallise and the crystallisate is taken up with 6 ml of 2N-hydrochloric acid. After extraction of the picric acid with 6×10 ml toluene, the aqueous phase is filtered and concentrated. 0.44 g (20%) of the trihydrochloride of the title compound is obtained in the form of a colourless, hygroscopic solid.

$C_{13}H_{24}Cl_3N_7S_2$ (448.9)

Rf (base, Alox. EtoAc/MeOH 1/1): 0.26

$^1$H-NMR data ($CD_3OD$, TMS as internal standard): δ=2.47 (s) 3 H, 2.61–3.22 (m) 4 H, 3.37–3.78 (m) 4 H, 3.99 (s) 2 H, 4.9(broad) 8 H, 7.50 (s) 1 H, 8.89 (s) 1 H, 8.99 (s) 1 H, ppm.

EXAMPLE 22

$N^1$-[3-(Imidazol-4-yl)propyl]-$N^2$-[2-[[(5-methylthio-1H-imidazol-4-yl)methyl]thio]ethyl]guanidine

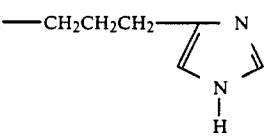

1.02 g (5 mmol) of 2-[(5-methylthioimidazol-4-yl)methylthio]ethylamine prepared from the dihydrochloride with sodium ethylate in ethanol are dissolved in 20 ml of acetonitrile. 1.59 g (5 mmol) of N-benzoyl-diphenylimidocarbonate are added and the reaction mixture is stirred at room temperature for 30 minutes. After the addition of 0.63 g (5 mmol) of 3-(imidazol-4-yl)propylamine, the reaction mixture is heated under reflux for 60 minutes and the benzoyl guanidine is then isolated by preparative layer chromatography (silica gel 60 $PF_{254}$, containing gypsum; solvent: chloroform/methanol.ammonia 94+6). After being concentrated by evaporation, the eluate is heated under reflux in 45 ml of 20% hydrochloric acid for 7 hours and worked up by a method analogous to that of Example 4. The residue obtained after concentration of the aqueous solution by evaporation crystallises when stirred with isopropanol/acetone. 0.25 g (11%) of the trihydrochloride is obtained as a hygroscopic solid.

$C_{14}H_{23}N_7S_2·3HCl$ (462.9)

MS (FAB method): m/z (rel.Int. [%])=354 ([M+H]+, 9), 127 (16), 109 (8), 79 (100).

$^1$H-NMR data ($d_6$-DMSO, TMS as internal standard): δ=1.87 (m) 2 H, 2.48 (s) 3 H, 2.6–2.9 (m) 4 H, 3.22 (m) 2 H, 3.48 (m) 2 H, 3.93 (s) 2 H, 7.50 (m) 1 H, 9.07 (d) 1 H, 9.20 (s) 1 H. ppm.

N-[2-(Imidazol-4-yl)ethyl]-N'-[3-[(5-methylimidazol-4-yl) methylthio]propyl]guanidine

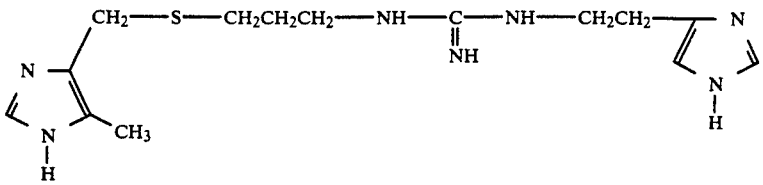

EXAMPLE 23

N-[2-(Imidazol-4-yl)ethyl]-N'-[3-[(5-methylimidazol-4-yl) methylthio]propyl]guanidine Preparation of the preliminary stage N-Cyano-N'-[2-(imidazol-4-yl)ethyl]-N''-[3-[(5-methylimidazol-4-yl)methylthio]propyl]guanidine

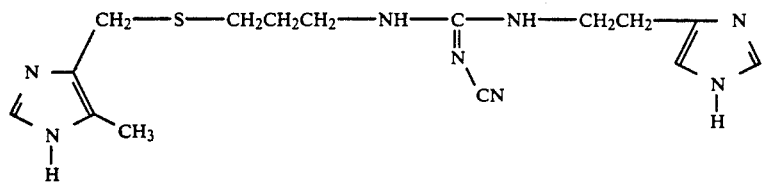

The base is released from 1.74 g (5 mmol) of 3-[(5-methylimidazol-4-yl)methylthio]propylamine dihydrobromide in ethanol by means of 10 mmol of sodium methylate and concentrated to half its volume by evaporation, and the sodium bromide is separated off. 1.18 g (5 mmol) of N-cyanodiphenylimidocarbonate are added to the filtrate and the mixture is stirred at room temperature for one hour. When the reaction mixture has been concentrated by evaporation under vacuum, 0.72 g (6.5 mmol) of histamine base in 30 ml of absolute pyridine is added and the mixture is boiled under reflux for 1.5 hours and concentrated by evaporation under vacuum. The product is isolated by column chromatography (neutral aluminium oxide, eluant: methanol/chloroform 4:96). After concentration by evaporation under vacuum, the eluate solidifies as a dry foam which, when stirred with ether, yields 0.8 g (46%) of N-cyano-N'-[2-(imidazol-4-yl)-ethyl]-N''-[3-[(5-methyl-imidazol-4-yl)methylthio]propyl]guanidine melting at 135°–137° C.

$C_{15}H_{22}N_8S$ (346.5) Calc.: C 52.00 H 6.40 N 32.34. Found: C 52.47 H 6.64 N 31.85.

IR (KBr): 2180 cm$^{-1}$ (C≡N)

$^1$H-NMR data (d$_6$-DMSO, H-D exchange with D$_2$O, TMS as internal standard): δ = 1.70 (m) 2 H, 2.14 (s) 3 H, 2.24 (t) 2 H, 2.73 (t) 2 H, 3.18 (t) 2 H, 3.36 (t) 2 H, 3.64 (s) 2 H, 6.89 (s) 1 H, 7.48 (s) 1 H, 7.62 (s) 1 H, ppm.

0.7 g (2.02 mmol) of N-cyano-N'-2-(imidazol-4-yl)ethyl-N''-[3-[(5-methylimidazol-4-yl)methylthio]-propyl]guanidine are heated under reflux in 30 ml of 18% hydrochloric acid for 6 hours and evaporated to dryness, leaving 0.98 g (100%) of a turbid oil of ammonium chloride and N-[2-(imidazol-4-yl)ethyl]-N'-[3-[(5-methylimidazol-4-yl)methylthio]propyl]guanidine trihydrochloride as residue.

$C_{14}H_{23}N_7S \cdot 3HCl \cdot NH_4Cl$ (484.3)

The base is converted into the tripicrate melting at 171°–174° C. (decomposition).

$C_{14}H_{23}N_7S \cdot 3C_6H_3N_3O_7$ (1008.8) Calc.: C 38.10 H 3.20 N 22.22. Found: C 37.95 H 3.28 N 22.30.

$^1$H-NMR data (d$_6$-DMSO, H-D-exchange with CF$_3$COOD, TMS as internal standard): δ = 1.78 (m) 2 H, 2.30 (s) 3 H, 2.52 (t) 2 H, 2.95 (t) 2 H, 3.24 (t) 2 H, 3.51 (t) 2 H, 3.86 (s) 2 H, 7.50 (s) 1 H, 8.72 (s) 6 H, 8.96 (s) 1 H, 9.05 (s) 1 H, ppm.

EXAMPLE 24

N-Benzoyl-N'-[3-(imidazol-4-yl)propyl]-N''-[2-[(1-methylimidazol-2-yl)—methylthio]ethyl]guanidine

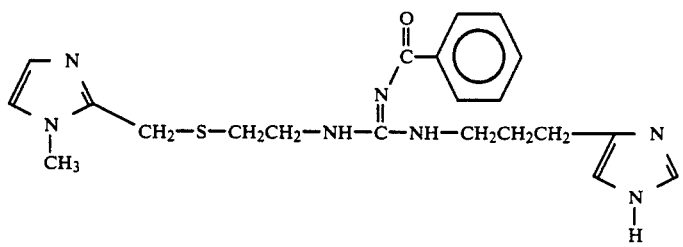

The base is released from 1.67 g (5 mmol) of 2-(1methylimidazol-2-yl)methylthio]ethylamine dihydrobromide by means of sodium ethylate in ethanol. The filtered solution is concentrated by evaporation under vacuum and taken up with 20 ml of tert.-butanol. After the addition of 1.59 g (5 mmol) of N-benzoyl-diphenylimidocarbonate, the reaction mixture is stirred at room temperature for 20 minutes. After the addition of 0.63 g of 3-(imidazol-4-yl)propylamine dissolved in 10 ml of tert.-butanol, the reaction mixture is heated under reflux for one hour and concentrated by evaporation under vacuum, and the product is isolated by preparative layer chromatography (see Example 2) (solvent: ethyl acetate/methanolic ammonia, 80:20). After concentration of the eluate by evaporation, the oily residue crystallises when stirred with ethyl acetate. 1.1 g (52%) of N-benzoyl-N'-[3-(imidazol-4-yl) propyl]-N''-[2-[(1-methylimidazol-2-yl)methylthio]ethyl]guanidine melting at 151°–152° C. are obtained after recrystallisation from acetonitrile.

$C_{21}H_{27}N_7OS$ (425.6) Calc.: C 59.27 H 6.40 N 23.04. Found: C 59.18 H 6.46 N 23.12.

MS: m/z (rel. Int. [%]) = 425 (M+, 2), 109 (55), 105 (100), (87), 77 (63).

IR (KBr): 1600 cm$^{-1}$ (C=O)

$^1$H-NMR data (d$_6$-DMSO, TMS as internal standard): δ = 1.85 (m) 2 H 2.3–3.8 (m) 8 H, 3.60 (s) 3 H. 3.87 (s) 2 H, 6.75 (m) 2 H, 7.03 (d) 1 H, 7.35 (m) 3 H, 7.52 (s) 1 H, 8.03 (m) 2 H,ppm.

EXAMPLE 25

N-[3-(Imidazol-4-yl)propyl]-N'-[2-[(1-methylimidazol-2-yl) methylthio]ethyl]guanidine placeable by D$_2$O, 8.17 (t) 1 H, replaceable by D$_2$O, 9.02 (d) 1 H, ppm.

EXAMPLE 26

N-Benzoyl-N'[2-[2-(4-chlorobenzyl)-5-methylimidazol-4-yl]methylthio]ethyl-N''-[3-(imidazol-4-yl)-propyl]-guanidine

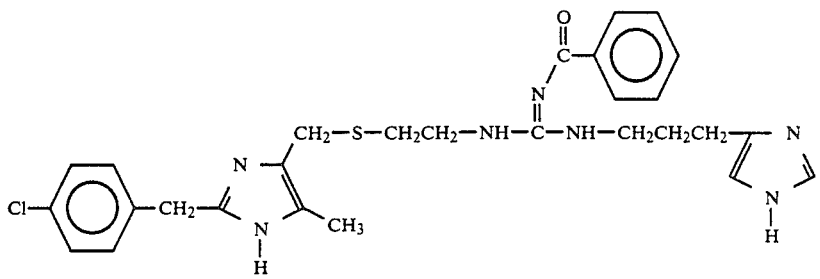

0.74 g (2.5 mmol) of 2-[[2-(4-chlorobenzyl)-5-methylimidazol-4-yl]-methylthio]ethylamine prepared from the dihydrobromide by reaction with sodium ethylate and 0.79 g (2.5 mmol) of N-benzoyl-diphenylimidocarbonate are stirred together at room temperature in 20 ml of tert.-butanol for 20 minutes. After the addition of 0.63 g of 3-(imidazol-4-yl)propylamine dissolved in 10 ml of tert.-butanol, the reaction mixture is heated under reflux for one hour and the product is isolated by preparative layer chromatography (solvent: ethyl acetate/methanol.ammonia 90:10).

When the eluate is stirred up with water after it has been concentrated by evaporation, it yields 0.15 g

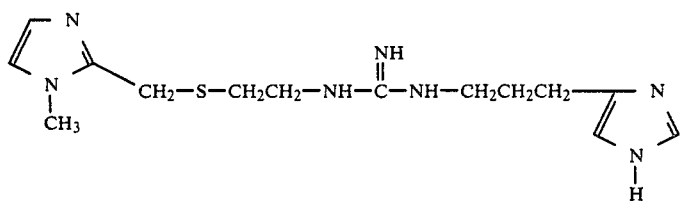

0.6 g (1.41 mmol) of N-benzoyl-N'-3-(imidazol-4-yl) propyl]-N''-[2-[(1-methylimidazol-2-yl)methylthio]ethyl]guanidine (Example 24) are heated under reflux in 45 ml of 20% hydrochloric acid for 3 hours and worked up by a method analogous to that of Example 4. Yield: 0.4 g (66%) of dry foam.

$C_{14}H_{23}N_7S \cdot 3HCl$ (430.8)

MS m/z (rel. Int. [%]) = 321 (M+, 1), 194 (34), 151 (22), (60), 95 (100).

$^1$H-NMR data (d$_6$-DMSO, TMS as internal standard): δ = 1.85 (m) 2 H, 2.72 (m) 4 H, 2.95–3.65 (m) 4 H, 3.85 (s) 3 H, 4.33 (s) 2 H, 7.43 (m) 1 H, 7.58 (d) 1 H, 7.68 (d) 1 H, 7.7 2 H, replaceable by D$_2$O, 7.95 (t) 1 H, re- (11%) of a solid Which sinters at temperatures of 90° C. and upwards.

$C_{28}H_{32}ClN_7OS$ (550.1) Calc.: C 61.13 H 5.86 N 17.82. Found: C 61.12 H 6.02 N 17.57.

MS: m/z (rel. Int. [%]) = 219 (2), 109 (2), 105 (16), 95(5), 77 (10), 43 (100).

$^1$H-NMR data (d$_6$-DMSO, TMS as internal standard): δ = 1.83 (m) 2 H, 2.05 (s) 3 H, 2.3–2.7 (m) 4 H, 3.0–3.8 (m) 4 H, 3.60 (s) 2 H, 3.80 (s) 2 H, 6.72 (m) 1 H, 6.9–7.6 (m) 8 H, 8.00 (m) 2 H, ppm.

EXAMPLE 27

N-Benzoyl-N'-2-[(2-dimethylaminomethyl-5-methylimidazol-4-yl)methylthio]ethyl]-N''-[3-(imidazol-4-yl)propyl]guanidine

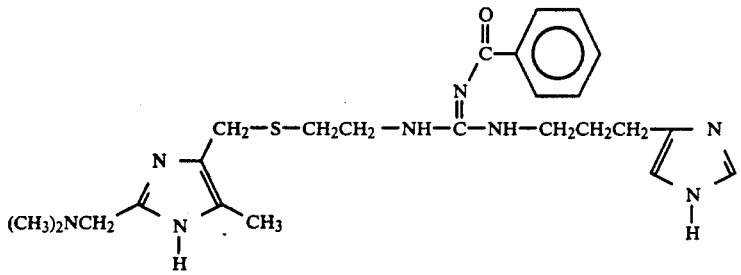

obtained from 1.14 g (5 mmol) of 2-[[(2-dimethylaminomethyl-5-methylimidazol-4-yl)-methylthio]]-ethylamine and equimolar quantities of N-benzoyl-diphenylimidocarbonate and 3-(imidazol-4-yl)propylamine in acetonitrile The product is isolated by preparative layer chromatography (solvent: ethyl acetate/methanol·ammonia, 85:15). Concentration of the eluate by evaporation yields a colourless oil which solidifies when stirred with 10 ml of water and a few drops of ethanol. After dehydration over calcium chloride under vacuum, 0.25 g (10%) of the dihydrate which sinters at 51°–52° C. is left $C_{24}H_{34}N_8OS \cdot 2H_2O$ (518.7) Calc.: C 55.58 H 7.38 N 21.60. Found: C 55.35 H 7.43 N 21.49.

MS: m/z (rel Int. [%])=153 (69), 109 (32), 108 (97), 105(24), 43 (100).

$^1$H-NMR data (d$_6$-DMSO, TMS as internal standard): $\delta$=1.87 (m) 2 H. 2.06 (s) 3 H, 2.13 (s) 6 H, 2.35–2.85 (m) 4 H, 3.28 (s) 2 H, 3.63 (s) 2 H, 3.05–3.7 (m) 4 H, 6.73 (s) 1 H, 7.2–7.6 (m) 4 H. 8.03 (m) 2 H,ppm.

EXAMPLE 28

N-Benzoyl-N'-[2-[(2 dimethylaminomethylthiazol-4-yl)methylthio]ethyl]-N''-[3-(imidazol-4-yl)propyl]guanidine

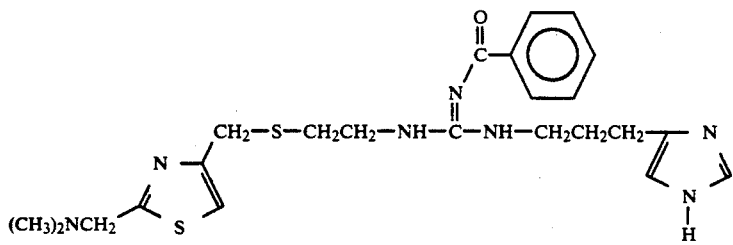

The base is released from 1.7 g (5 mmol) of 2-[(2-dimethylaminomethylthiazol-4-yl)thiomethyl]-ethylamine trihydrobromide by means of 15 mmol of sodium ethylate in 100 ml of ethanol. The sodium chloride which precipitates is filtered off and the filtrate is concentrated by evaporation under vacuum. The oily residue is taken up with 20 ml of acetonitrile and stirred at room temperature for 35 minutes after the addition of 1.59 g (5 mmol) of N-benzoyl-diphenylimidocarbonate. After the addition of 0.69 g (5.5 mmol) of 3-(imidazol-4-yl)propylamine, the reaction mixture is heated under reflux for 40 minutes The reaction product is isolated by preparative layer chromatography (solvent: ethyl acetate/methanol·ammonia 97:3). The eluate is concentrated by evaporation under vacuum, taken up with a small quantity of acetonitrile and then kept in the refrigerator for crystallisation after the addition of ether. Yield: 0.37 g (15%), melting point 99°–101° C.

$C_{23}H_{31}N_7OS_2$ (485.7) Calc.: C 56.88 H 6.43 N 20.19. Found: C 56.84 H 6.51 N 20.24.

MS: m/z (rel. Int. [%])=485 (M$^+$, 10), 105 (100) 77 (83)

$^1$H-NMR data (d$_6$-DMSO, TMS as internal standard): $\delta$=1.85 (m) 2 H, 2.23 (s) 6 H, 2.35–2.95 (m) 4 H, 2.95–3.75 (m) 4 H, 3.67 (s) 2 H, 3.83 (s) 2 H, 6.76 (s) 1 H, 7.15–7.65 (m) 5 H, 8.06 (m) 2 H, ppm.

EXAMPLE 29

N-[2-[(2-Dimethylaminomethylthiazol-4-yl)methylthio]ethyl]-N'-[3-(imidazol-4-yl)propyl]guanidine

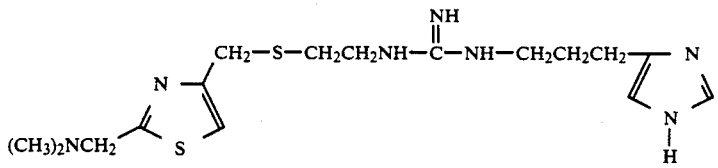

0.32 g (0.66 mmol) of N-benzoyl-N'-2-[(2-dimethylaminomethylthiazol-4-yl)methylthio]ethyl]-N''[[3-(imidazol-4-yl) propyl]guanidine (Example 28) are heated under reflux in 45 ml of 20% hydrochloric acid for 7 hours and worked up by a method analogous to that of Example 4. The foam initially obtained is crushed, stirred up with anhydrous acetone, suction filtered and dried under vacuum. 0.21 g (60%) of a hygroscopic solid is obtained.

$C_{16}H_{27}N_7S_2 \cdot 4HCl$ (527.4)

MS: m/z (rel. Int [%])=381 (M+, 7), 154 (21), 109 (100), 95(47),81 (55),59 (41).

$^1$H-NMR data (d$_6$-DMSO, TMS as internal standard): δ=1.87 (m) 2 H, 2.4–2.9 (m) 4 H. 2.82 (s) 6 H, 2.95–3.75 (m) 4 H, 3.97 (s) 2 H, 4.70 (s) 2 H, 7.50 (m) 1 H, 7.72 (s, broad) 2 H, replaceable by D$_2$O, 7.82 (s) 1 H, 8.05 (m) 1 H, replaceable by D$_2$O, 8.22 (m) 1 H, replaceable by D$_2$O, 9.03 (d) 1 H, ppm.

EXAMPLE 30

N-Benzoyl-N'-[2-[(2-(3,4,5,6-tetrahydropyrimidin-2(1H)-ylidene)aminothiazol-4-yl)methylthio]ethyl]-N''-[3-(imidazol-4-yl)propyl]guanidine Preparation of the preliminary stages a) 2-[[2-(3,4,5,6-tetrahydropyrimidin-2(1H)-ylidene)aminothiazol-4-yl]methylthio]ethylamine

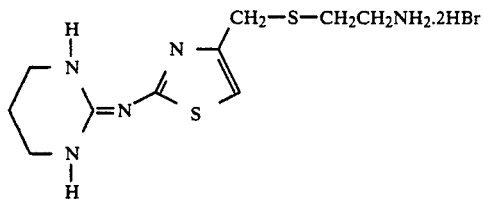

5.34 g (20 mmol) of 4-Chloromethyl-2-(hexahydropyrimidin-2-ylidene)aminothiazole hydrochloride and 2.27 g (20 mmol) of cysteamine hydrochloride are heated under reflux in 50 ml of 48% aqueous hydrobromic acid for 4 hours. After concentration of the reaction mixture by evaporation under vacuum, the residue is boiled up with ethanol. 6.57 g (76%) of 2-[2-(3,4,5,6-tetrahydropyrimidin-2(1H)-ylidene)aminothiazole-4-yl]methylthio]ethylamine crystallise in the process as the dihydrobromide in a chromatographically pure form. Colourless needles melting at 243° C. are obtained after recrystallisation from ethanol/water.

C$_{10}$H$_{17}$N$_5$S$_2$·2HBr (433.2) Calc.: C 27.72 H 4.42 N 16.17. Found: C 27.53 H 4.46 N 16.07.

MS: m/z (rel. Int. [%])=271 (M+, 5), 227 ([M-C$_2$H$_6$N]+, 100), 195 ([M-C$_2$H$_6$NS]+, 88).

$^1$H-NMR data (d$_6$-DMSO, TMS as internal standard): δ=1.92 (m) 2 H, 2.5–3.75 (m) 8 H, 3.80 (s) 2 H, 7.15 (s) 1 H, ppm.

b) N-Benzoyl-N'-[2-[(2-(3,4,5,6-tetrahydropyrimidin-2(1H)-ylidene)aminothiazol-4-yl)methylthio]ethyl]-O-phenyl-isourea

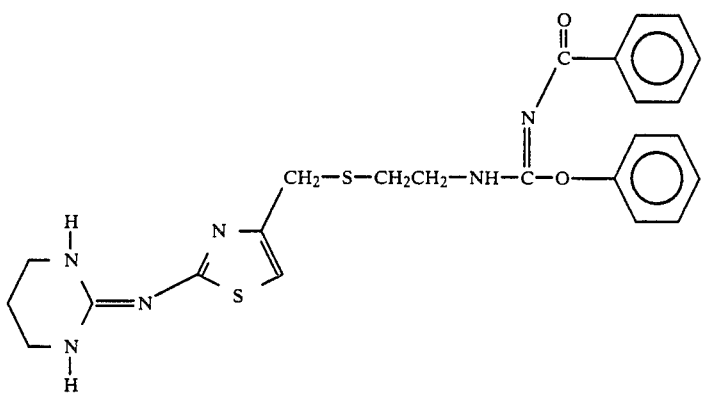

The base is liberated from 2.17 g (5 mmol) of 2-[[2-(3,4,5,6-tetrahydropyrimidin-2(1H)-ylidene)aminothiazol-4-yl]methylthio]ethylamine dihydrobromide by means of 10 mmol of sodium ethylate in 100 ml of ethanol. After removal of the ethanol by evaporation under vacuum, the residue is taken up with acetonitrile. Precipitated sodium bromide is filtered off and the filtrate is stirred at room temperature for 4 hours after the addition of 1.59 g (5 mmol) of N-benzoyl-diphenylimidocarbonate. The chromatographically pure solid which precipitates is suction filtered and washed with acetonitrile. 1.5 g (61%) of N-benzoyl-N'-[2-[(2-(3,4,5,6-tetrahydropyrimidin-2(1H)-ylidene)aminothiazol-4-yl)methylthio]ethyl]-O-phenyl isourea are obtained. This product melts at 138°–139° C. after recrystallisation from hot acetonitrile C$_{24}$H$_{26}$N$_6$O$_2$S$_2$ (494.6) Calc.: C 58.28 H 5.30 N 16.99. Found: C 58.24 H 5.28 N 17.01.

MS: m/z (rel. Int. [%])=494 (M+, 1), 105 (32, 94 (57), 77 (10), 66 (100).

$^1$H-NMR data (d$_6$-DMSO, TMS as internal standard): δ=1.73 (m) 2 H, 2.83 (t) 2 H, 3.05–3.45 (m) 4 H, 3.65 (s) 2 H 3.70 (dt), 2 H, 6.40 (s) 1 H, 7.0–7.6 (m) 8 H, 7.80 (m) 2 H, 8.18 (broad) 2 H, replaceable by D$_2$O, 10.06 (t) 1 H, replaceable by D$_2$O, ppm.

N-Benzoyl-N'-[2-[(2-(3,4,5,6-tetrahydropyrimidin-2-(1H)-ylidene)aminothiazol-4-yl)methylthio]ethyl]-N''-[3-(imidazol-4-yl)propyl]guanidine

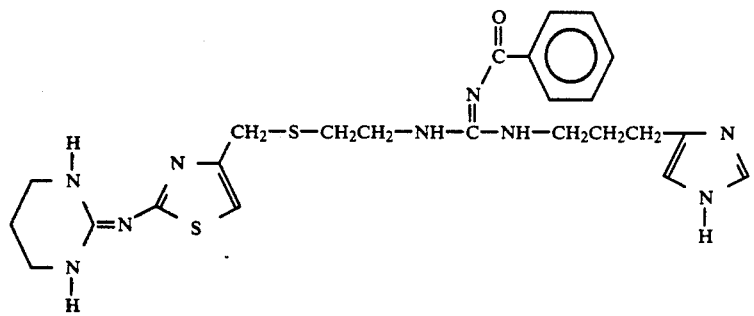

1.3 g (2.63 mmol) of N-benzoyl-N'-2-[(2-(tetrahydropyrimidin-2-ylidene)aminothiazol-4-yl)methylthio]ethyl]-O-phenyl-isourea and 0.38 g (3 mmol) of 3-(imidazol-4-yl) propylamine are heated under reflux in 20 ml of acetonitrile for 30 minutes. When the solution has cooled and after the addition of 20 ml of ether, the oil which initially separates solidifies when stirred. 1.1 g (80%) of a solid which melts at 175°–176° C. when recrystallised from ethanol/water are obtained.

$C_{24}H_{31}N_9OS_2$ (525.7) Calc.: C 54.83 H 5.94 N 23.98. Found: C 54.96 H 6.09 N 24.00.

MS: m/z (rel. Int. [%])=525 (M+, 1), 227 (23), 195 (21), 108 (10), 105 (100), 95 (35), 77 (61).

$^1$H-NMR data (d$_6$-DMSO, TMS as internal standard): δ=1.5–2.2 (m) 4 H, 2.35–2.93 (m) 4 H, 3.63 (s) 2 H, 2.95–3.85 (m) 8 H, 6.35 (s) 1 H, 6.77 (s) 1 H, 7.15–7.65 (m) 4 H, 8.07 (m) 2 H, ppm.

EXAMPLE 31

N-[2-[(2-(3,4,5,6-Tetrahydropyrimidin-2(1H)-ylidene)aminothiazol-4-yl)methylthio]ethyl]-N''-[3-(imidazol-4-yl)propyl]guanidine

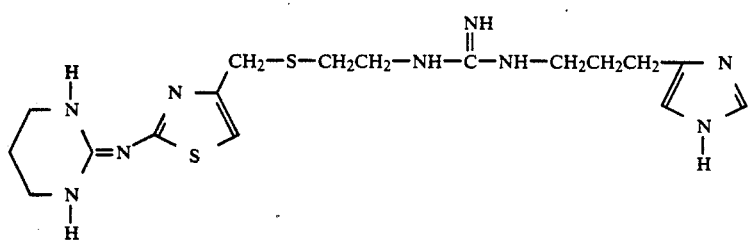

0.6 g (1.1 mmol) of N-benzoyl-N'-2-(2-(3,4,5,6-tetrahydropyrimidin-2 (1H)-ylidene)aminothiazol-4-yl)methylthio]ethyl]-N''-[3-(imidazol-4-yl)propyl]-guanidine are heated under reflux in 45 ml of 20% hydrochloric acid for 7 hours and worked up in a manner analogous to that of Example 4. The residue obtained after concentration of the aqueous solution by evaporation is stirred up with anhydrous acetone, suction filtered and dehydrated under vacuum. 0.59 g (97%) of hygroscopic solid is obtained.

$C_{17}H_{27}N_9S_2 \cdot 3HCl$ (531.0)

MS m/z (rel. Int. [%])=421 (M+, 3), 195 (100), 109 (35), 95 (17), 81 (52), 59 (28).

$^1$H-NMR data (d$_6$-DMSO, H-D exchange with CF$_3$COOD; TMS as internal standard): δ=1.6–2.25 (m) 4 H, 2.4–3.0 (m) 4 H, 3.05–3.8 (m) 8 H, 3.87 (s) 2 H, 7.17 (s) 1 H, 7.48 (m) 1 H, 9.07 (d) 1 H, ppm.

EXAMPLE 32

N-Benzoyl-N'-[3-[2-(3,4,5,6-tetrahydropyrimidin-2(1H)-ylidene)aminothiazol-4-yl]propyl]-N''-[3-(imidazol-4-yl) propyl]guanidine Preparation of the preliminary stages a) N-[3-[2-(3,4,5,6-Tetrahydropyrimidin-2(1H)-ylidene)aminothiazol-4-yl]propyl]phthalimide

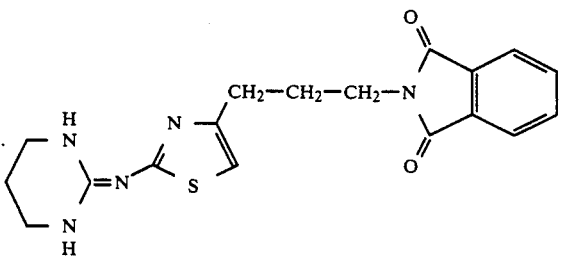

4.75 g (30 mmol) of (3,4,5,6-tetrahydropyrimidin-2(1H)-ylidene)-thiourea and 9.3 g (30 mmol) of N-(5-bromo-4-oxopentyl)phthalimide are stirred at room temperature in 150 ml of acetone for 5 hours. The solid which precipitates is suction filtered, washed with acetone and recrystallised from ethanol/water. 12.3 g (91%) of colourless needles, melting point 244° C., are obtained.

$C_{18}H_{19}N_5O_2S \cdot HBr$ (450.4) Calc.: C 48.00 H 4.48 N 15.55. Found: C 47.73 H 4.44 N 15.73.

MS: m/z (rel. Int. [%])=369 (M+, 36), 209 (30), 1.96 (100), 160 (7), 125 (13).

$^1$H-NMR data (d$_6$-DMSO, TMS as internal standard): δ=1.65–2.25 (m) 4 H, 2.65 (t) 2 H, 3.43 (m) 4 H, 3.63 (t) 2 H, 6.83 (s) 1 H, 7.83 (m) 4 H, 8.85 (broad) 2 H, replaceable by D$_2$O, 11.5 (broad) 1 H, replaceable by D$_2$O, ppm.

b) 3-[2-(3,4,5,6-Tetrahydropyrimidin-2(1H)-ylidene)aminothiazol-4-yl]propylamine

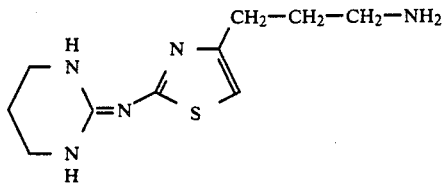

9.0 g (20 mmol) of N-[3-[2-(3,4,5,6-tetrahydro-2(1H)-ylidene)amino]thiazol-4-yl]-propylphthalimide and 2 ml of hydrazine hydrate are heated together under reflux in 150 ml of ethanol for 4 hours. The reaction mixture is then concentrated by evaporation under vacuum and the residue is heated under reflux for a further 2 hours in 150 ml of 20% hydrochloric acid and the phthalic acid hydrazide which precipitates after the reaction mixture has been kept in a refrigerator is filtered off. The filtrate is concentrated by evaporation under vacuum, made alkaline with sodium hydroxide solution and extracted three times with methylene chloride.

1.2 g (5 mmol) of 3-[2-(3,4,5,6-tetrahydropyrimidin-2-(1H)-ylidene)aminothiazol-4-yl]-propylamine are dissolved in 10 ml of methylene chloride and added to a solution of 1.59 g (5 mmol) of N-benzoyl-diphenylimidocarbonate in 20 ml of methylene chloride. The reaction mixture is stirred at room temperature for 15 minutes and then concentrated by evaporation under vacuum and stirred up with acetonitrile for crystallisation. 2.2 g (95%) of colourless solid melting at 165°–167° C. after recrystallisation from acetonitrile are obtained.

$C_{24}H_{26}N_6O_2S$ (462.6) Calc.: C 62.32 H 5.67 N 18.17. Found: C 62.30 H 5.65 N 18.24.

$^1$H-NMR data (CDCl$_3$, TMS as internal standard): δ = 1.65–2.35 (m) 4 H, 2.70 (t) 2 H, 3.15–3.75 (m) 6 H, 6.13 (s) 1 H, 6.95–7.55 (m) 8 H, 7.90 (m) 4 H, 2 H replaceable by D$_2$O, 10.3 (t) 1 H, replaceable by D$_2$O, ppm.

N-Benzoyl-N'[3-[2-(3,4,5,6-tetrahydropyrimidin-2-(1H)-ylidene)aminothiazol-4-yl]propyl]-N''-[3-(imidazol-4-yl)propyl]-guanidine

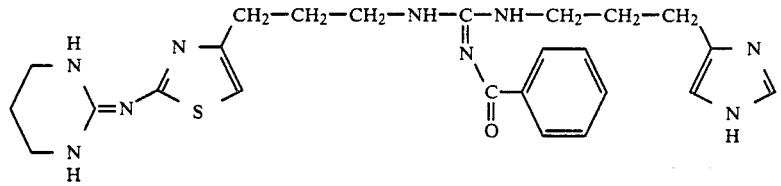

The combined extracts are washed with water, dehydrated over sodium sulphate and concentrated by evaporation under vacuum, and the residue is crystallised from acetone. 4.2 g (88%) of 3-[2-(3,4,5,6-tetrahydropyrimidin-2(1H)-ylidene)aminothiazol-4-yl]-propylamine melting at 116° C. are obtained.

$C_{10}H_{17}N_5S$ (239.3) Calc.: C 50.18 H 7.16 N 29.26. Found: C 49.73 H 7.22 N 29.06.

MS: m/z (rel. Int. [%]) = 239(M+, 24), 209 (66), 196 (100), 125 (26).

$^1$H-NMR data (CDCl$_3$, TMS as internal standard): δ = 1.23 (broad) 2 H, replaceable as by D$_2$O 1.5–2.15 (m) 4 H, 2.35–2.92 (m) 4 H, 3.43 (t) 4 H, 6.03 (s) 1 H, 8.45 (broad) 2 H, replaceable by D$_2$O, ppm.

The dihydrochloride melts at 259°–260° C. after crystallisation from ethanol.

$C_{10}H_{17}N_5S \cdot 2HCl$ (312.3) Calc.: C 38.46 H 6.13 N 22.43. Found: C 38.75 H 6.38 N 22.04.

$^1$H-NMR data (d$_6$-DMSO, H-D exchange with CF$_3$COOD, TMS as internal standard): δ = 1.93 (m) 4 H, 2.45–3.05 (m) 4 H, 3.47 (t) 4 H, 6.88 (s) 1 H, ppm.

c) N-Benzoyl-N'-[3-[2 -(3,4,5,6-tetrahydropyrimidin-2(1H)-ylidene)aminothiazol-4-yl]propyl]-O-phenyl-isourea 2.1 g (4.5 mmol) of N-benzoyl-N'-[3-[2-(3,4,5,6-tetrahydropyrimidin-2(1H)-ylidene)aminothiazol-4-yl]propyl]-O-phenyl-isourea and 0.6 g (4.8 mmol) of 3-(imidazol-4-yl)-propylamine are heated under reflux in 30 ml of acetonitrile for 3 hours. After concentration by evaporation under vacuum, the reaction product is isolated by preparative layer chromatography (silica gel 60 PF$_{254}$ containing gypsum; solvent: ethyl acetate/methanol.ammonia, 94:6). The eluate is concentrated by evaporation under vacuum and the oily residue is taken up with ethanol and crystallised by the addition of water. 1.3 g (59%) of colourless solid melting at 158°–159° C. are obtained $C_{24}H_{31}N_9OS$ (493.6) Calc.: C 58.40 H 6.33 N 25.54. Found: C 58.23 H 6.34 N 25.47.

$^1$H-NMR data (CDCl$_3$, TMS as internal standard): δ = 1.5–2.35 (m) 6 H, 2.68 (m) 4 H, 3.05–3.65 (m) 8 H. 6.13 (s) 1 H, 6.74 (s) 1 H, 7.05–7.55 (m) 4 H, 7.75 (broad) 2 H, replaceable by D$_2$O, 8.18 (m) 2 H, 9.0 (broad) 1 H, replaceable by D$_2$O, ppm.

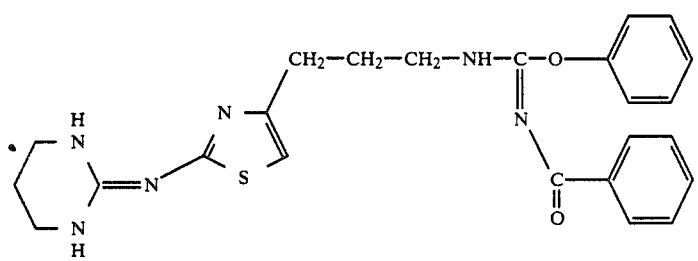

EXAMPLE 33

N-[3-[2-(3,4,5,6-Tetrahydropyrimidin-2(1H)-ylidene)aminothiazol-4-yl]propyl]-N'-[3-(imidazol-4-yl)propyl]-guanidine

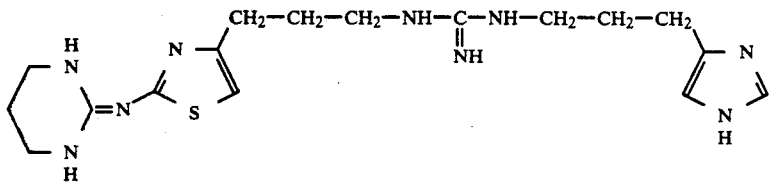

0.9 g (1.8 mmol) of N-benzoyl-N'-[3-[2-(3,4,5,6-tetrahydropyrimidin-2(1H)-ylidene)aminothiazol-4-yl]propyl]-N''-[3-(imidazol-4-yl)propyl]-guanidine are heated under reflux in 30 ml of 20% hydrochloric acid for 5 hours. The reaction mixture is worked up by a method analogous to that of Example 4. 0.65 g (93%) of the trihydrochloride is obtained in the form of a hygroscopic, amorphous solid.

$C_{17}H_{27}N_9S \cdot b$ 3HCl (498.9) Molar mass 389 (FAB-MS).

$^1$NMR data ($d_6$-DMSO, H-D exchange with $CF_3COOD$, TMS as internal standard): $\delta = 1.55-2.3$ (m) 6 H, 2.5–3.0 (m) 4 H, 3.0–3.7 (m) 8 H, 6.87 (s) 1 H, 7.43 (m) 1 H. 9.03 (d) 1 H, ppm.

EXAMPLE 34

N-Benzoyl-N'-[2-[(2-(diaminomethyleneamino)thiazol-4-yl) methylthio]ethyl]-N''-[3-(imidazol-4-yl)propyl]-guanidine Preparation of the preliminary stage N-Benzoyl-N'[2-[(2-(diaminomethyleneamino)thiazol-4-yl) methylthio]ethyl]-0-phenyl-isourea

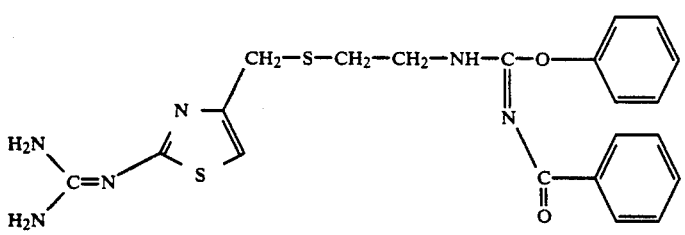

1.15 g (5 mmol) of 2-[(2-(diaminomethyleneamino)thiazol-4-yl)methylthio]ethylamine and 1.59 g (5 mmol) of N-benzoyl-diphenylimidocarbonate are stirred at room temperature in 40 ml of acetonitrile for 3 hours. The precipitated colourless solid is thin layer chromatographically pure and directly suitable for further use.

Yield: 1.9 g (84%). The substance crystallises from ethanol/water in the form of colourless needles melting at 135° C.

$C_{21}H_{22}N_6O_2S_2$ (454.6) Calc.: C 55.49 H 4.88 N 18.49. Found: C 55.24 H 4.97 N 18.47.

$^1$H-NMR data ($d_6$-DMSO, TMS as internal standard): $\delta = 2.80$ (t) 2 H, 3.65 (s) 2 H, 3.67 (m) 2 H, 6.47 (s) 1 H, 6.77 (s, broad) 4 H, replaceable by $D_2O$, 7.0–7.6 (m) 8 H, 7.75 (m) 2 H, 10.0 (t) 1 H (replaceable by $D_2O$, ppm.

N-Benzoyl-N'-[2-[(2-(diaminomethyleneamino)thiazol-4-yl) methylthio]ethyl]-N''-[3-(imidazol-4-yl)propyl]-guanidine

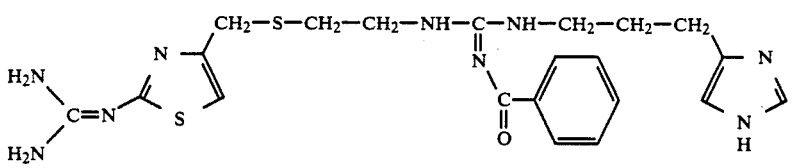

1.0 g (2.2 mmol) of N-benzoyl-N'-[2-[(2-diaminomethyleneamino)thiazol-4-yl)methylthio]ethyl]-O-phenyl-isourea and 0.35 g (2.8 mmol) of 3-(imidazol-4-yl)-propylamine are heated together under reflux in 30 ml of acetonitrile for 3 hours. The reaction product is isolated by preparative layer chromatography (silica gel 60 $PF_{254}$ containing gypsum: solvent: ethyl acetate/methanol.ammonia 95:5). 0.28 g (26%) of colourless needles melting at 133°–134° C. crystallise from ethanol/water.

$C_{21}H_{27}N_9S_2O$ (485.6) Molar mass 485 (FAB-MS).

$^1$H-NMR data ($d_6$-DMSO, H-D exchange with $D_2O$, TMS as internal standard): $\delta = 1.87$ (m) 2 H, 2.3–2.95 (m) 4 H., 3.0–3.95 (m) 4 H, 3.65 (s) 2 H, 6.43 (s) 1 H, 6.77 (s) 1 H, 7.1–7.7 (m) 4 H, 8.05 (m) 2 H, ppm.

EXAMPLE 35

N-Benzoyl-N'-[3-(imidazol-4-yl)propyl]-N''-(3-phenoxypropyl)guanidine

Preparation of the preliminary stage

N-Benzoyl-N'-(3-phenoxypropyl)-O-phenyl-isourea

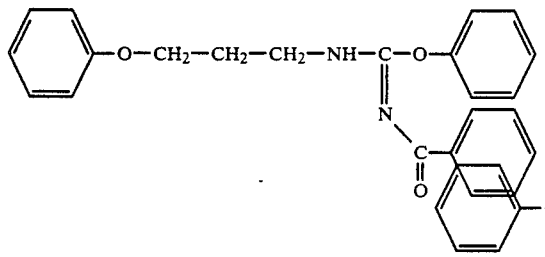

1.0 g (6.6 mmol) of 3-phenoxypropylamine and 2.09 g (6.6 mmol) of N-benzoyl-diphenylimidocarbonate are stirred together in 30 ml of ether for 15 minutes at room temperature. When the reaction product is concentrated by evaporation under vacuum, it partly precipitates. 0.2 g of precipitate are removed for analytical purposes and the remainder of the reaction mixture is subjected to further reaction as described below. N-Benzoyl-N'-(3-phenoxypropyl)-O-phenylisourea crystallises from ether in the form of colourless needles, melting point 75° C.

$C_{23}H_{22}N_2O_3$ (374.4) Calc.: C 73.78 H 5.92 N 7.48. Found: C 73.63 H 5.85 N 7.44.

$^1$H-NMR data (d$_6$-DMSO, TMS as internal standard): δ=2.13 (m) 2 H, 3.70 (dt) 2 H, 4.10 (t) 2 H, 6.7–7.65 (m) 13 H, 7.78 (m) 2 H, 10.07 (t) 1 H, replaceable by D$_2$O, ppm.

N-Benzoyl-N'-[3-(imidazol-4-yl)propyl]-N''-(3-phenoxypropyl)-guanidine

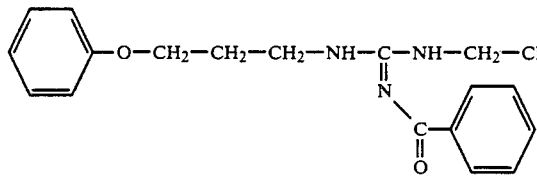

The previously obtained solution of 6.1 mmol of N-benzoyl-N'-(3-phenoxypropyl)-O-phenyl-isourea is concentrated by evaporation under vacuum and the residue is dissolved in acetonitrile and then heated under reflux for 3 hours after the addition of 0.8 g (6.4 mmol) of 3-(imidazol-4-yl)-propylamine. The reaction mixture obtained is then concentrated by evaporation under vacuum, the residue is taken up with dilute hydrochloric acid and the aqueous solution is extracted three times with ether. After alkalisation with sodium hydroxide solution, the reaction product is extracted from the aqueous phase with methylene chloride, the extract obtained is concentrated by evaporation, and the reaction product is crystallised from the concentrated extract by means of ethyl acetate. 0.95 g (38%) of colourless solid melting at 149° C. after recrystallisation from ethanol/water is obtained.

$C_{23}H_{27}N_5O_2$ (405.5) Calc.: C 68.13 H 6.71 N 17.27. Found: C 68.17 H 6.83 N 17.11.

$^1$H-NMR data (d$_6$-DMSO, TMS as internal standard): δ=1.75–2.30 (m) 4 H, 2.35–2.8 (m) 2 H, 3.0–3.75 (m) 4 H, 4.07 (t) 2 H, 6.7–7.6 (m) 10 H, 8.08 (m) 2 H, ppm.

EXAMPLE 36

N-[3-(Imidazol-4-yl)propyl]-N'-(3-phenoxypropyl)-guanidine

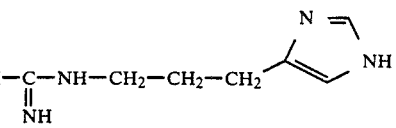

0.42 g (1 mmol) of N-benzoyl-N'-[3-(imidazol-4-yl)propyl]-N''-(3-phenoxypropyl)-guanidine are heated under reflux in 30 ml of 20% hydrochloric acid for 5 hours. The reaction mixture is worked up by a method analogous to that of EXAMPLE 4. 0.35 g (94%) of the dihydrochloride is obtained as a hygroscopic, amorphous solid.

$C_{16}H_{23}N_5O \cdot 2HCl$ (374.3) Molar mass 301 (FAB-MS).

$^1$H-NMR data (d$_6$-DMSO, TMS as internal standard): δ=1.95 (m) 4 H, 2.75 (t) 2 H, 2.95–3.6 (m) 4 H, 4.05 (t) 2 H, 6.7–7.5 (m) 6 H, 7.5–8.2 (m) 4 H, replaceable by D$_2$O, 9.00 (d) 1 H, ppm.

EXAMPLE 37

N-Benzoyl-N'-(2-hydroxy-3-phenoxypropyl)-N''-[3-(imidazol-4-yl)propyl]-guanidine Preparation of the preliminary stage 2-Benzoylimino-5-phenoxy-methyloxazolidine

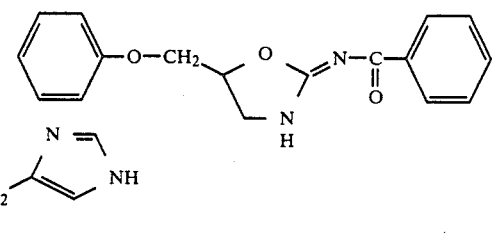

Method A 1.67 g (10 mmol) of 2-hydroxy-3-phenoxypropylamine and 3.17 g (10 mmol) of N-benzoyl-diphenylimidocarbonate are stirred together in 20 ml of methylene chloride for 5 hours at room temperature. The solvent is then distilled off under vacuum and the residue is crystallised with acetonitrile.

Yield: 1.8 g (61%) of colourless crystals, melting point 142° C.

Method B 1.67 g (10 mmol) of 2-hydroxy-3-phenoxypropylamine in 10 ml of methylene chloride are added dropwise to a solution of 2.02 g (10 mmol) of benzoyl isocyanide dichloride in 20 ml of methylene chloride at 0° to −10° C. After the dropwise addition of a mixture of 1.5 ml of triethylamine and 10 ml of methylene chloride, the reaction mixture is stirred for 30 minutes, the triethylammonium chloride formed is removed by washing with water, and the organic phase is dehydrated over sodium sulphate and concentrated by evaporation under vacuum. The residue is recrystallised from methanol.

Yield: 2.5 g (84%) of colourless crystals, melting point 144° C.

$C_{17}H_{16}N_2O_3$ (296.3) Calc.: C 68.91 H 5.44 N 9.45. Found: C 68.62 H 5.40 N 9.59.

MS: m/z (rel. Int. [%])=296 (M+, 17), 105 (23), 85 (93), 83 (100), 58 (75).

$^1$H-NMR data (CDCl$_3$, TMS as internal standard): δ=3.95 (dd) 1 H, 4.07 (dd) 1 H, 4.25 (d) 2 H, 5.11 (m) 1 H, 6.91 (m) 2 H, 7.03 (m) 1 H, 7.2–7.6 (m) 5 H, 8.24 (m) 2 H, 9.55 (broad), replaceable by D$_2$O, ppm.

N-Benzoyl-N'-(2-hydroxy-3-phenoxypropyl)-N'''-[3-(imidazol-4-yl)propyl]-guanidine

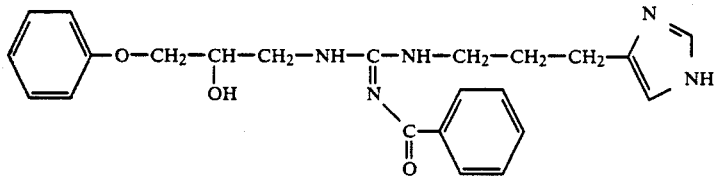

1.48 g (5 mmol) of 2-benzoylimino-5-phenoxymethyloxazolidine and 0.69 g (5.5 mmol) of 3-(imidazole-4-yl)-propylamine are heated together under reflux in a mixture of 40 ml of acetonitrile and 10 ml of ethanol for 8 hours. The reaction mixture is concentrated by evaporation under vacuum and the product is isolated and purified by preparative layer chromatography (silica gel 60 PF$_{254}$ containing gypsum: solvent; chloroform/methanol 98:2, ammoniacal atmosphere). Crystallisation from acetonitrile results in 0.8 g (38%) of colourless crystals, melting point 129° C.

$C_{23}H_{27}N_5O_3$ (421.5) Calc.: C 65.54 H 6.46 N 16.62. Found: C 65.36 H 6.52 N 16.41.

$^1$H-NMR data (DMSO-d$_6$, TMS as internal standard): δ=1.96 (m) 2 H, 2.4–2.8 (m) 2 H, 3.0–3.7 (m) 4 H, 3.7–4.2 (m) 3 H, 7.6–6.7 (m) 10 H, 8.10 (m) 2 H, ppm.

EXAMPLE 38

N-(2-Hydroxy-3-phenoxypropyl)-N'-[3-(imidazol-4-yl)propyl]-guanidine

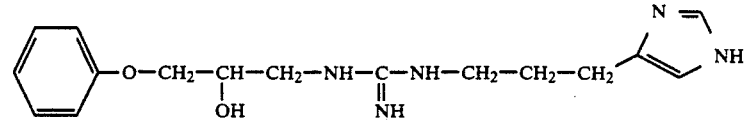

0.5 g (1.2 mmol) of N-benzoyl-N'-(2-hydroxy-3-phenoxypropyl)-N''-[3-(imidazol-4-yl)propyl]-guanidine are heated under reflux in 30 ml of 20% hydrochloric acid for 6 hours. The reaction mixture is worked up by a method analogous to that of Example 4. The dihydrochloride crystallises from isopropyl alcohol/acetone in the form of colourless crystals melting at 165°–166° C.

Yield: 0.45 g (96%). Molar mass 317 (FAB-MS).

$C_{16}H_{23}N_5O_2 \cdot 2HCl$ (390.3) Calc.: C 49.24 H 6.46 N 17.94. Found: C 48.73 H 6.64 N 17.60.

$^1$-NMR data (d$_6$-DMSO, H-D exchange with CF$_3$COOD, TMS as internal standard): δ=1.85 (m) 2 H, 2.73 (t) 2 H, 3.20 (t) 2 H, 3.35 (m) 2 H, 3.95 (m) 3 H, 6.7–7.5 (m) 6 H, 8.93 (d) 1 H, ppm.

EXAMPLE 39

N-[3-(Imidazol-4-yl)propyl]-N'-[2-[(5-methylimidazol-4-yl) methylthio]-1-propyl]-guanidine.

Preparation of the preliminary stage

N-Cyano-N'-[3-(imidazol-4-yl)propyl]-N''-[2-[(5-methylimidazol-4-yl)methylthio]-1-propyl]-guanidine

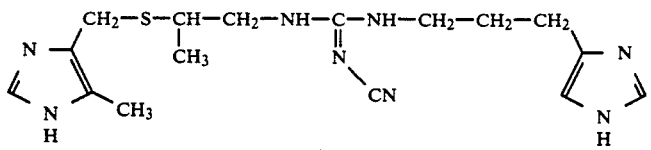

The base is liberated from 1.74 g (5 mmol) of 2-[(5-methylimidazol-4-yl)methylthio]-1-propylamine·2HBr by means of sodium ethanolate in absolute ethanol and separated from the precipitated sodium halide. 1.19 g (5 mmol) of N-cyano-diphenylimidocarbonate are added to the liberated base. After one hour's stirring at room temperature, the reaction mixture is evaporated to dryness under vacuum and the residue is dissolved in 30 ml of absolute pyridine with heating, added to 0.81 g (6.5 mmol) of 3-(imidazol-4-yl)propylamine (prepared from 1.29 g (6.5 mmol) of the dihydrochloride) and heated under reflux for 2 hours and then evaporated to dryness under vacuum. The product is isolated by column chromatography (basic aluminium oxide, eluant: methanol in chloroform, concentration rising continuously from 1.5% (V/V) to 3.75%). When the eluate has been concentrated by evaporation under vacuum, it is solidified by stirring with absolute ether/absolute ethanol and dried in vacuo.

Yield: 0.9 g (46%) of N-cyano-N'-[3-(imidazol-4-yl)propyl]-N''-[2-[(5-methylimidazol-4-yl)methylthio]-1-propyl]guanidine·0.75 ethanol, melting range 65°–100° C.

$C_{16}H_{24}N_8S \cdot 0.75\ C_2H_5OH$ (395.0) Calc.: C 53.21 H 7.27 N 28.37. Found: C 52.75 H 6.81 N 28.35.

$^1$H-NMR data (d$_6$-DMSO, H-D exchange with D$_2$O, TMS as internal standard): δ = 1.17 (d) 3 H, 1.78 (quint) 2 H, 2.14 (s) 3 H, 2.54 (t) 2 H, 2.97 (m) 1 H, 3.20 (t) 2 H, 3.31–3.48 (m) 2 H, 3.73 (quart) 2 H, 6.82 (s) 1 H, 7.48 (s) 1 H, 7.61 (s) 1 H, ppm.

N-[3-(Imidazol-4-yl)propyl]-N'-[2-[(5-methylimidazol-4-yl) methylthio]-1-propyl]-guanidine

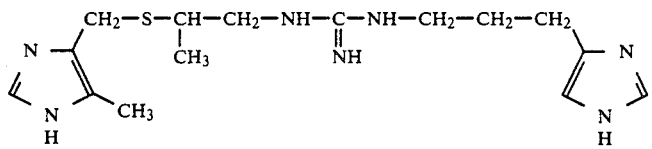

0.76 g (1.92 mmol) of the previously prepared cyanoguanidine is heated under reflux for 2 hours in 30 ml of 18% hydrochloric acid. Concentration of the reaction mixture by evaporation under vacuum leaves 0.96 g of hygroscopic foam composed of equimolar quantities of ammonium chloride and N-[3-(imidazol-4-yl)propyl]-N'-[2-[(5-methylimidazol-4-yl)methylthio]-1-propyl]-guanidine trihydrochloride.

$C_{15}H_{25}N_7S \cdot 3HCl \cdot NH_4Cl$ (498.3)

The base is converted into the tripicrate melting at 174°–175° C. (decomposition).

$C_{15}H_{25}N_7S \cdot 3C_6H_3N_3O_7 \cdot H_2O$ (1040.8).

Calc.: C 38.08 H 3.49 N 21.53. Found: C 38.30 H 3.51 N 21.47

$^1$H-NMR data (d$_6$-DMSO, TMS as internal standard): δ = 1.23 (d) 3 H, 1.88 (m) 2 H, 2.30 (s) 3 H, 2.76 (t) 2 H, 2.85–3.10 (m) 1 H, 3.1–3.5 (m) 4 H, 3.85–4.15 (m) 2 H, 7.18 (s) 1 H, replaceable by D$_2$O, 7.42 (s) 1 H, replaceable by D$_2$O, 7.52 (s) 1 H, 7.60 (s) 1 H, replaceable by D$_2$O, 7.77 (s) 1 H, replaceable by D$_2$O, 8.00 (broad) 1 H, replaceable by D$_2$O, 8.23 (broad) 1 H, replaceable by D$_2$O, 9.00 (s) 1 H, 9.08 (s) 1 H, ppm.

EXAMPLE 40

(S)-(−)-N-[3-(Imidazol-4-yl)propyl]-N'-[2-[(5-methyiimidazol-4-yl)methylthio]-1-propyl]-guanidine Preparation of the preliminary stage (S)-(−)-N-Cyano-N'[3-(imidazol-4-yl)propyl]-N''-[2-[(5-methylimidazol-4-yl)methylthio]-1-propyl]-guanidine

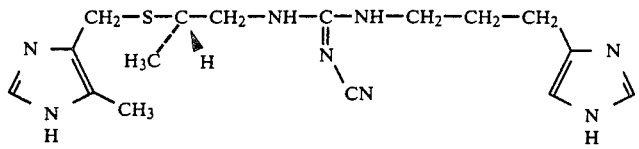

prepared by a method analogous to that of Example 39 (preliminary stage) from 1.74 g (5 mmol) of (S)-(−)-2-[(5-methylimidazol-4-yl)methylthio]-1-propylamine·2HBr, 1.19 g (5 mmol) of N-cyanodiphenylimidocarbonate and 1.29 g (6.5 mmol) of 3-(imidazol-4-yl)propylamine·2HCl.

Yield: 0.96 g (52%) of (S)-(−)-N-cyano-N'-[3-(imidazol-4-yl)propyl]-N''-[2-[(5-methylimidazol-4-yl)methylthio]-1-propyl]-guanidine·0.25 ethanol, melting range 50°–100° C., $[α]_D^{20} = -10.8°\pm0.4°$ (c=0.26; methanol).

$C_{16}H_{24}N_8S \cdot 0.25\ C_2H_5OH$ (372.0).

Calc.: C 53.27 H 6.91 N 30.12. Found: C 53.23 H 6.72 N 30.07.

$^1$H-NMR data (d$_6$-DMSO, H-D exchange with D$_2$O, TMS as internal standard): δ = 1.17 (d) 3 H, 1.78 (quint) 2 H, 2.13 (s) 3 H, 2.53 (t) 2 H, 2.95 (sext) 1 H, 3.18 (t) 2 H, 3.30–3.45 (d) 2 H, 3.70 (quart) 2 H, 6.79 (s) 1 H. 7.44 (s) 1 H, 7.57 (s) 1 H, ppm.

(S)-(−)-N-[3-(imidazol-4-yl)propyl]-N'-[2-[(5-methylimidazol-4-yl)methylthio]-1-propyl]-guanidine

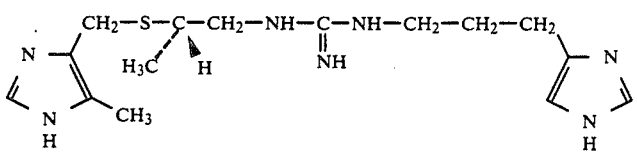

obtained by a method analogous to that of Example 39 from 0.82 g (2.2 mmol) of the previously prepared cyanoguanidine. 1.1 g of a hygroscopic foam composed of equimolar quantities of ammonium chloride and (S)-(−)-N-[3-(imidazol-4-yl)propyl]-N'-[2-[(5-methylimidazol-4-yl) methylthio]-1-propyl]-guanidine trihydrochloride is obtained.

$[α]_D^{20} = -17.7°\pm0.4°$ (c=0.73; 95% (V/V) methanol).

$C_{15}H_{25}N_7S \cdot 3Hcl \cdot NH_4Cl$ (498.3) $^1$H-NMR data (d$_6$-DMSO, TMS as internal standard): δ = 1.23 (d) 3 H, 1.88 (m) 2 H, 2.30 (s) 3 H, 2.76 (t) 2 H, 2.85–3.10 (m) 1 H,. 3.1–3.5 (m) 4 H, 3.85–4.15 (quart) 2 H, 7.21 (s) 1 H, replaceable by D$_2$O, 7.42 (s) 1 H, replaceable by D$_2$O, 7.52 (s) 1 H, 7.62 (s) 1 H, replaceable by D₂O, 7.77 (s) 1 H, replaceable by D₂O, 8.00 (broad) 1 H, replaceable by D₂O. 8.24 (broad) 1 H, replaceable by D₂O, 9.01 (s) 1 H, 9.08 (s) 1 H, ppm.

EXAMPLE 41

(R)-(+)-N-[3-(imidazol-4-yl)propyl]-N'-[2-[(5-methylimidazol-4-yl)methylthio]-1-propyl]-guanidine Preparation of the preliminary stage (R)-(+)-N-Cyano-N'-[3-(imidazol-4-yl)propyl]-N"-[2-[(5-methylimidazol-4-yl)methylthio]-1-propyl]-guanidine

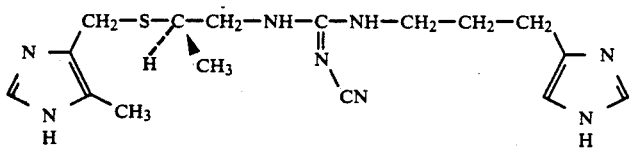

prepared by a method analogous to that of Example 39 (preliminary stage) from 1.74 g (5 mmol) of (R)-(+)-2-[(5-methylimidazol-4-yl)methylthio]-1-propylamine·2HBr, 1.19 g (5 mmol) of N-cyano-diphenylimido-carbonate and 1.29 g (6.5 mmol) of 3-(imidazol-4-yl)·propylamine·2HCl.

Yield: 0.77 g (41%) of (R)-(+)-N-cyano-N'-[3-(imidazol-4-yl) propyl]-N"-[2-[(5-methylimidazol-4-yl)methylthio]1-propyl]guanidine·0.25 ethanol, melting range 50°–100° C.

$[\alpha]_D^{20} = +10.5° \pm 0.7°$ (c=0.17; methanol)
$C_{16}H_{24}N_8S \cdot 0.25\ C_2H_5OH$ (372.0).

Calc.: C 53.27 H 6.91 N 30.12. Found: C 52.91 H 6.56 N 29.78.

¹H-NMR data (d₆-DMSO, H-D exchange with D₂O, TMS as internal standard): δ=1.13 (d) 3 H, 1.76 (quint) 2 H, 2.11 (s) 3 H, 2.4–2.6 (t) 2 H, 2.85–3.30 (m) 3 H, 3.30–3.55 (m) 2 H, 3.67 (quart) 2 H, 6.74 (s) 1 H, 7.41 (s) 1 H, 7.53 (s) 1 H, ppm.

(R)-(+)-N-[3-(imidazol-4-yl)propyl]-N'-[2-[(5-methylimidazol-4-yl)methylthio]-1-propyl]-guanidine

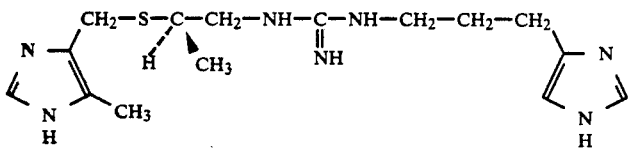

prepared by a method analogous to that of Example 39 from 0.63 g (1.7 mmol) of the previously prepared cyanoguanidine. 0.85 g of a hygroscopic foam composed of equimolar quantities of ammonium chloride and (R)-(+)-N-[3-(imidazol-4-yl)propyl]-N'-[2-[(5-methylimidazol-4-yl) methylthio]-1-propyl]guanidine trihydrochloride is obtained as residue.

$[\alpha]_D^{20} = +17.3° \pm 0.7°$ (c=0.45; 95% (V/V) methanol)
$C_{15}H_{25}N_7S_3 \cdot HCl \cdot NH_4Cl$ (498.3)

¹H-NMR data (d₆-DMSO, TMS as internal standard): δ=1.23 (d) 3 H, 1.88 (m) 2 H, 2.30 (s) 3 H, 2.76 (t) 2 H, 2.85–3.05 (m) 1 H, 3.1–3.5 (m) 4 H, 3.85–4.15 (quart) 2 H, 7.18 (s) 1 H, replaceable by D₂O, 7.39 (s) 1 H, replaceable by D₂O, 7.52 (s) 1 H, 7.59 (s) 1H, replaceable by D₂O, 7.76 (s) 1 H, replaceable by D₂O, 7.98 (broad) 1 H, replaceable by D₂O, 8.22 (broad) 1 H, replaceable by D₂O, 9.00 (s) 1 H, 9.07 (s) 1 H, ppm.

EXAMPLE 42

N-[3-(Imidazol-4-yl)propyl]-N'-[1-[(5-methylimidazol-4-yl) methylthio]-2-propyl]-guanidine Preparation of the preliminary stage N-Cyano-N'[3-(imidazol-4-yl)propyl]-N"-[1-[(5-methyl imidazol-4-yl)methylthio]-2-propyl]-guanidine

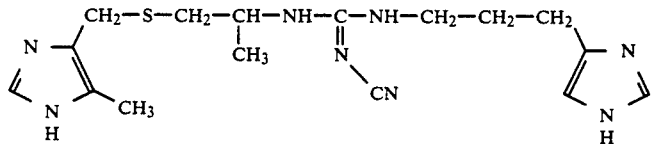

prepared by a method analogous to that of Example 39 (preliminary stage) from 1.74 g (5 mmol) of 1 [(5-methylimidazol-4-yl)methylthio]-2-propylamine·2HBr, 1.19 g (5 mmol) of N-cyano-diphenylimidocarbonate and 1.29 g (6.5 mmol) of 3-(imidazol-4-yl)propylamine·2HCl.

Yield: 0.98 g (50%) of N-cyano-N'-[3-(imidazol-4-yl)propyl]-N"-[1-[(5-methylimidazol-4-yl)methylthio]-2-propyl]guanidine·0.75 ethanol, melting range 60°–100° C.

$C_{16}H_{24}N_8S \cdot 0.75\ C_2H_5OH$ (395.0).

Calc.: C 53.21 H 7.27 N 28.37. Found: C 52.91 H 6.92 N 28.30.

¹H-NMR data (d₆-DMSO, H-D exchange with D₂O, TMS as internal standard): δ=1.17 (d) 3 H, 1.80 (quint) 2 H, 2.12 (s) 3 H, 2.5–2.7 (m) 4 H, 3.20 (t) 2 H, 3.66 (s) 2 H, 3.85–4.05 (m) 1 H, 6.82 (s) 1 H, 7.50 (s) 1 H, 7.62 (s) 1 H, ppm.

N-[3-(Imidazol-4-yl)propyl]-N'-[1-[(5-methylimidazol-4-yl) methylthio]-2-propyl]-guanidine

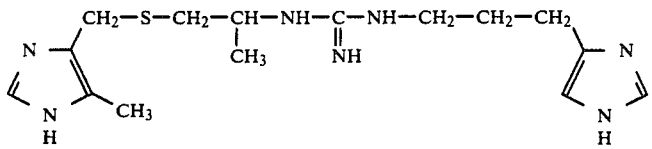

prepared by a method analogous to that of Example 39 from 0.84 g (2.1 mmol) of the previously prepared cyanoguanidine. 1.05 g of a hygroscopic foam composed of equimolar quantities of ammonium chloride and N-[3-(imidazol-4-yl)propyl]-N'[1-[(5-methylimidazol-4-yl)methylthio]-propyl]guanidine trihydrochloride are obtained as residue.

$C_{15}H_{25}N_7S \cdot 3HCl \cdot NH_4Cl$ (498.3)

$^1$H-NMR data (d$_6$-DMSO, TMS as internal standard): δ=1.19 (d) 3 H, 1.88 (m) 2 H, 2.31 (s) 3 H, 2.64 (d) 2 H, 2.76 (t) 2 H, 3.1–3.4 (m) 2 H, 3.96 (s) 2 H, 4.0–4.3 (m) 1 H, 7.21 (s) 1 H, replaceable by D$_2$O, 7.42 (s) 1 H, replaceable by D$_2$O, 7.53 (s) 1 H, 7.63 (s) 1 H, replaceable by D$_2$O, 7.73 (s) 1 H, replaceable by D$_2$O, 7.95 (broad) 1 H, replaceable by D$_2$O, 8.15 (broad) 1 H, replaceable by D$_2$O, 9.00 (s) 1 H, 9.07 (s) 1 H, ppm.

EXAMPLE 43

(R)-(−)-N-[3-(Imidazol-4-yl)propyl]-N'-[1-[(5-methylimidazol-4-yl)methylthio]-2-propyl]-guanidine Preparation of the preliminary stage (R)-(−)-N-Cyano-N'-[3-(imidazol-4-yl)propyl]-N''-[1-[(5-methylimidazol-4-yl)methylthio]-2-propyl]-guanidine

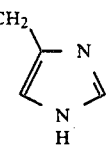

prepared by a method analogous to that of Example 39 (preliminary stage) from 1.74 g (5 mmol) of (R)-(−)-1-[(5-methylimidazol-4-yl)methylthio]-2-propylamine·2HBr, 1.19 g (5 mmol) of N-cyanodiphenylimidocarbonate and 1.29 g (6.5 mmol) of 3-(imidazol-4-yl)-propylamine·2HCl.

Yield: 1.01 g (56%), melting range 50°–95° C.
$[α]_D^{20} = -84.0° \pm 1.5°$ (c=0.13; methanol)

$C_{16}H_{24}N_8S$ (360.5). Calc.: C 53.31 H 6.71 N 31.08. Found: C 53.16 H 6.58 N 31.16.

$^1$H-NMR data (d$_6$-DMSO, H-D exchange with D$_2$O, TMS as internal standard): δ=1.17 (d) 3 H, 1.80 (quint) 2 H, 2.13 (s) 3 H, 2.5–2.7 (m) 4 H, 3.20 (t) 2 H, 3.66 (s) 2 H, 3.85–4.20 (m) 1 H, 6.80 (s) 1 H, 7.47 (s) 1 H, 7.58 (s) 1 H, ppm.

(R)-(−)-N-[3-(Imidazol-4-yl)propyl]N'-[1-[(5-methylimidazol-4-yl)methylthio]-2-propyl]-guanidine

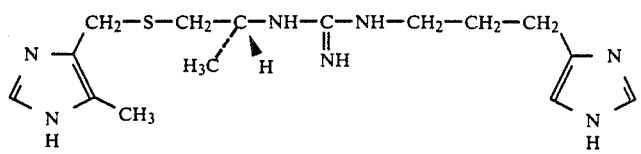

prepared by a method analogous to that of Example 39 from 0.76 g (2.1 mol) of the previously prepared cyanoguanidine. 1.05 g of a hygroscopic foam composed of equimolar quantities of ammonium chloride and (R)-(−)-N-[3-(imidazol-4-yl)propyl]-N'-[1-[(5-methylimidazol-4-yl)methylthio]-2-propyl]guanidine trihydrochloride are obtained as residue.

$[α]_D^{20} = -33.6° \pm 0.7°$ (c=0.67; 95% (V/V) methanol).

$C_5H_{25}N_7S \cdot 3HCl \cdot NH_4Cl$ (498.3)

$^1$H-NMR data (d$_6$-DMSO, TMS as internal standard); δ=1.19 (d) 3 H, 1.89 (m) 2 H, 2.32 (s) 3 H, 2.64 (d) 2 H, 2.77 (t) 2 H, 3.1–3.4 (m) 2 H. 3.97 (s) 2 H, 4.0–4.3 (m) 1 H, 7.22 (s) 1 H, replaceable by D$_2$O, 7.43 (s) 1 H, replaceable by D$_2$O, 7.53 (s) 1 H, 7.64 (s) 1 H, replaceable by D$_2$O, 7.74 (s) 1 H, replaceable by D$_2$O, 7.93 (broad) 1 H, replaceable by D$_2$O, 8.18 (broad) 1H, replaceable by D$_2$O, 9.00 (s) 1 H, 9.08 (s) 1 H, ppm.

EXAMPLE 44

(S)-(+)-N-[3-(Imidazol-4-yl)propyl]-N'-[1-(5-methylimidazol-4-yl)methylthio]-2-propyl]-guanidine Preparation of the preliminary stage (S)-(+)-N-Cyano-N'-[3-(imidazol-4-yl)propyl]-N''-[1-[(5-methylimidazol-4-yl)methylthio]-2-propyl]-guanidine

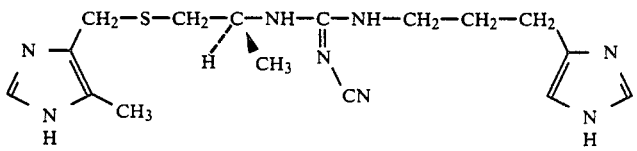

prepared by a method analogous to that of Example 39 (preliminary stage) from 1.74 g (5 mmol) of (S)-(+)-1-[(5-methylimidazol-4-yl)methylthio]-2-propylmaine·2HBr, 1.19 g (5 mmol) of N-cyano-diphenylimidocarbonate and 1.29 g (6.5 mmol) of 3-(imidazol-4-yl)-propylamine·2HCl.

Yield: 0.73 g (40%) of (S)-(+)-N-cyano-N'-[3-(imidazol-4-yl)propyl]-N''-[1-[(5-methylimidazol-4-yl)methylthio]-2-propyl]-guanidine, melting range 50°–100° C.

$[\alpha]_D^{20} = +87.2° \pm 0.9°$ (c=0.22; methanol)

$C_{16}H_{24}N_8S$ (360.5) Calc.: C 53.31 H 6.71 N 31.08. Found: C 53.80 H 7.01 N 31.29.

$^1$H-NMR data (d$_6$-DMSO, H-D exchange with D$_2$O, TMS as internal standard): δ=1.17 (d) 3 H, 1.79 (quint) 2 H, 2.12 (s) 3 H, 2.45–2.7 (m) 4 H, 3.19 (t) 2 H, 3.66 (s) 2 H, 3.85–4.05 (m) 1 H, 6.79 (s) 1 H, 7.46 (s) 1 H, 7.58 (s) 1 H, ppm.

(S)-(+)-N-[3-(imidazol-4-yl)propyl]-N'-[1-[(5-methylimidazol 4-yl)methylthio]-2-propyl]-guanidine

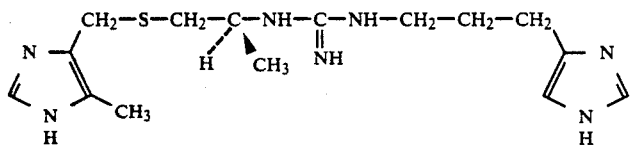

prepared by a method analogous to that of Example 39 from 0.58 9 (1.6 mmol) of the previously prepared cyanoguanidine. 0.8 g of a hygroscopic foam composed of equimolar quantities of ammonium chloride and (S)-(+)-N-[3-(imidazol-4-yl)propyl]-N'-[1-[(5-methylimidazol-4-yl)methylthio]-2-propyl]-guanidine trihydrochloride is obtained as residue.

$[\alpha]_D^{20} = +35.1° \pm 1.0°$ (c=0.45; 95% (V/V) methanol)

$C_{15}H_{25}N_7S·3HCl·NH_4Cl$ (498.3)

$^1$H-NMR data (d$_6$-DMSO, TMS as internal standard): δ=1.19 (d) 3 H, 1.88 (quint) 2 H, 2.30 (s) 3 H, 2.64 (d) 2 H, 2.77 (t) 2 H, 3.1–3.4 (m) 2 H, 3.97 (s) 2 H, 4.0–4.3 (m) 1 H, 7.22 (s) 1 H, replaceable by D$_2$O, 7.43 (s) 1 H, replaceable by D$_2$O, 7.53 (s) 1 H, 7.64 (s) 1 H, replaceable by D$_2$O, 7.74 (s) 1 H, replaceable by D$_2$O, 7.95 (broad) 1 H, replaceable by D$_2$O, 8.20 (broad) 1 H, replaceable by D$_2$O, 9.00(s) 1 H, 9.08 (s) 1 H, ppm.

EXAMPLE 45

N-[3-(Imidazol-4-yl)propyl]-N'-[1-[(5-methylimidazol-4-yl) methylthio]-2-butyl]-guanidine Preparation of the preliminary stage N-Cyano-N'-[3-(imidazol 4-yl)propyl]-N''-[1-[(5-methylimidazol-4-yl)methylthio]-2-butyl]-guanidine

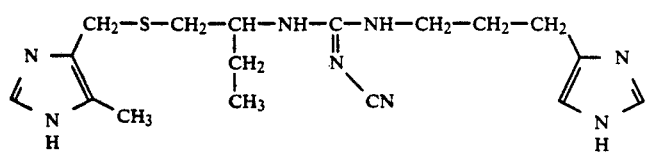

prepared by a method analogous to that of Example 39 (preliminary stage) from 1.81 g (5 mmol) of 1-[(5-methylimidazol-4-yl)methylthio]-2-butylamine·2HBr, 1.19 g (5 mmol) of N-cyano-diphenylimidocarbonate and 1.29 g (6.5 mmol) of 3-(imidazol-4-yl)-propylamine·2HCl.

Yield: 0.95 g (51%), melting range 50°–100° C.

$C_{17}H_{26}N_8S$ (374.5) Calc.: C 54.52 H 7.00 N 29.92. Found: C 54.60 H 6.95 N 29.78.

$^1$H-NMR data (d$_6$-DMSO, H-D exchange with D$_2$O, TMS as internal standard): δ=0.84 (t) 3 H, 1.35–1.70 (m) 2 H, 1.81 (quint) 2 H, 2.12 (s) 3 H, 2.45–2.75 (m) 4 H, 3.22 (t) 2 H, 3.66 (s) 2 H, 3.7–3.9 (m) 1 H, 6.8 (s) 1 H, 7.48 (s) 1 H, 7.58 (s) 1 H, ppm.

N-[3-(Imidazol-4-yl)propyl]-N'-[1-[(5-methylimidazol-4-yl) methylthio]2-butyl]-guanidine

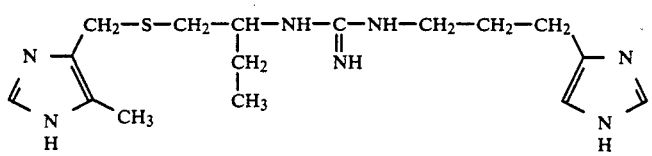

prepared by a method analogous to that of Example 39 from 0.71 g (1.9 mmol) of the previously prepared cyanoguanidine. 0.97 g of a hygroscopic foam composed of equimolar quantities of ammonium chloride and N-[3-(imidazol--yl)propyl]-N'-[1-[(5-methylimidazol-4-yl)methylthio]-2-butyl]-guanidine trihydrochloride is obtained as residue.

$C_{16}H_{27}N_7S·3HCl·NH_4Cl$ (512.4)

$^1$H-NMR data (d$_6$-DMSO, TMS as internal standard): δ=0.88 (t) 3 H, 1.3–1.75(m) 2 H, 1.88 (m) 2 H, 2.30 (s) 3 H, 2.62 (d) 2 H, 2.76 (t) 2 H, 3.25 (m) 2 H, 3.85–4.2 (m) 3 H, 7.22 (s) 1 H, replaceable by D$_2$O, 7.44 (s) 1 H, replaceable by D$_2$O, 7.52 (s) 1 H, 7.62 (s) 1 H, replaceable by D$_2$O, 7.80 (broad) 2 H, replaceable by D$_2$O, 8.20 (broad) 1 H, replaceable by D$_2$O, 9.0 (s) 1 H, 9.08 (s) 1 H, ppm.

EXAMPLE 46

(R)-(−)-N-[3-(Imidazol-4-yl)propyl]-N'-[1-[(5-methylimidazol-4-yl)methylthio]-2-butyl]-guanidine Preparation of the preliminary stage (R)-(−)-N-Cyano-N'-[3-(imidazol-4-yl)propyl]-N''-[1-[(5-methylimidazol-4-yl)methylthio]-2-butyl]guanidine

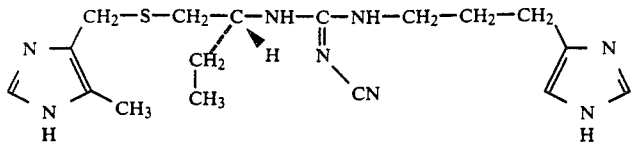

prepared by a method analogous to that of Example 39 (preliminary stage) from 1.81 g (5 mmol) of (R)-(−)-1-[(5-methylimidazol-4-yl)methylthio]-2-butylamine·2HBr, 1.19 g (5 mmol) of N-cyano-diphenylimidocarbonate and 1.29 g (6.5 mmol) of 3-(imidazol-4-yl)propylamine·2HCl.

Yield: 0.98 g (52%), melting range 55°–95° C.
$[\alpha]_D^{20} = -69.5° \pm 0.5°$ (c=0.38; methanol)
$C_{17}H_{26}N_8S$ (374.5) Calc.: C 54.52 H 7.00 N 29.92.

Found: C 55.00 H 6.77 N 29.44.

$^1$H-NMR data (d$_6$-DMSO, H-D exchange with D$_2$O, TMS as internal standard): δ=0.83 (t) 3 H, 1.35–1.7 (m) 2 H, 1.78 (quint) 2 H, 2.11 (s) 3 H, 2.45–2.65 (m) 4 H, 3.21 (t) 2 H, 3.65 (s) 2 H, 3.7–3.9 (m) 1 H, 6.78 (s) 1 H, 7.44 (s) 1 H, 7.56 (s) 1 H, ppm.

(R)-(−)-N-[3-(Imidazol-4-yl)propyl]-N'-[1-[(5-methylimidazol-4-yl)methylthio]-2-butyl]-guanidine

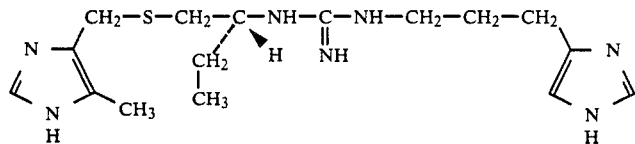

prepared by a method analogous to that of Example 39 from 0.8 g (2.1 mmol) of the previously prepared cyanoguanidine. 1.08 g of a hygroscopic foam composed of equimolar quantities of ammonium chloride and (R)-(−)-N-[3-(imidazol-4-yl)propyl]-N'-[1-[(5-methylimidazol-4-yl) methylthio]-2-butyl]-guanidine trihydrochloride are obtained as residue.
$[\alpha]_D^{20} = -29.7° \pm 0.6°$ (c=0.71; 95% (V/V) methanol)

$C_{16}H_{27}N_7S·3HCl·NH_4Cl$ (512.4)

$^1$H-NMR data (d$_6$-DMSO, TMS as internal standard): δ=0.88(t) 3 H, 1.3–1.75 (m) 2 H, 1.88 (m) 2 H, 2.30 (s) 3 H, 2.62 (d) 2 H, 2.76 (t) 2 H, 3.25 (m) 2 H, 3.85–4.15 (m) 3 H, 7.21 (s) 1 H, replaceable by D$_2$O, 7.42 (s) 1 H, replaceable by D$_2$O, 7.52 (s) 1 H, 7.62 (s) 1 H, replaceable by D$_2$O, 7.83 (broad) 2 H, replaceable by D$_2$O, 8.18 (broad) 1 H, replaceable by D$_2$O, 9.00 (s) 1 H, 9.07 (s) 1 H, ppm.

EXAMPLE 47

(S)-(+)-N-[3-(Imidazol-4-yl)propyl]-N'-[1-[(5-methylimidazol-4-yl)-methylthio]-2-butyl]-guanidine Preparation of the preliminary stage (S)-(+)-N-Cyano-N'-[3-(imidazol-4-yl)propyl]-N''-[1-[(5-methylimidazol-4-yl)methylthio]-2-butyl]-guanidine

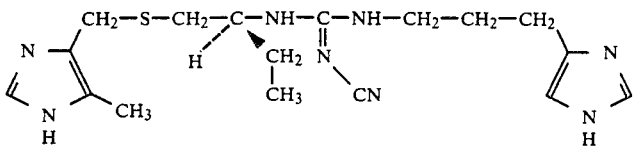

prepared by a method analogous to that of Example 39 (preliminary stage) from 1.81 g (5 mmol) of (S)-(+)-1-[(5-methylimidazol-4-yl)methylthio]-2-butylamine·2HBr, 1.19 g (5 mmol) of N-cyano-diphenylimidocarbonate and 1.29 g (6.5 mmol) of 3-(imidazol-4-yl)propylamine·2HCl.

Yield: 1.08 g (58%), melting range 55°–95° C.
$[\alpha]_D^{20} = +66.5° \pm 0.8°$ (c=0.21; methanol)

$C_{17}H_{26}N_8S$ (374.5) Calc.: C 54.52 H 7.00 N 29.92.
Found: C 54.79 H 6.64 N 29.88.

$^1$H-NMR data (d$_6$-DMSO, H-D exchange with D$_2$O, TMS as internal standard): δ=0.85 (t) 3 H, 1.4–1.7 (m) 2 H, 1.82 (quint) 2 H, 2.14 (s) 3 H, 2.5–2.75 (m) 4 H, 3.23 (t) 2 H, 3.68 (s) 2 H, 3.7–3.85 (m) 1 H, 6.81 (s) 1 H, 7.49 (s) 1 H, 7.60 (s) 1 H, ppm.

(S)-(+)-N-[3-(Imidazol-4-yl)propyl]-N'-[1-[(5-methylimidazol-4-yl)methylthio]-2-butyl]-guanidine

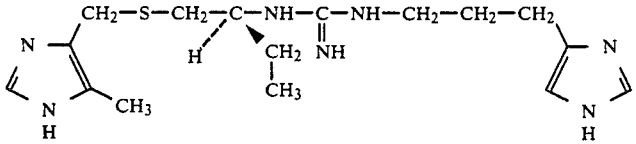

prepared by a method analogous to that of Example 39 from 0.86 g (2.3 mmol) of the previously prepared cyanouanidine. 1.18 g of a hygroscopic foam composed of equimolar quantities of ammonium chloride and (S)-(+)-N-[3-(imidazol-4-yl)propyl]-N'-[1-[(5-methylimidazol-4-yl)methylthio]-2-butyl]-guanidine trihydrochloride are obtained as residue.
$[\alpha]_D^{20} = +29.4° \pm 0.5°$ (c=0.84; 95% (V/V) methanol).

$C_{16}H_{27}N_7S·3HCl·NH_4Cl$ (512.4)

¹H-NMR data (d₆-DMSO, TMS as internal standard): δ=0.88 (t) 3 H, 1.35–1.75 (m) 2 H, 1.89 (m) 2 H, 2.30 (s) 3 H, 2.62 (d) 2 H, 2.77 (t) 2 H, 3.27 (m) 2 H, 3.85–4 2 (m) 3 H, 7.24 (s) 1 H, replaceable by D₂O, 7.44 (s) 1 H, replaceable by D₂O, 7.52 (s) 1 H, 7.65 (s) 1 H, replaceable by D₂O, 7.80 (broad) 2 H, replaceable by D₂O, 8.18 (broad) 1 H, replaceable by D₂O, 9.00 (s) 1 H, 9.08 (s) 1 H, ppm.

EXAMPLE 48

N-[3-(Imidazol-4-yl)propyl]-N'[3-[(5-methylimidazol-4-yl)methylthio]propyl]-guanidine Preparation of the preliminary stage N-Cyano-N'[3-(imidazol-4-yl)propyl]-N''-[3-[(5-methylimidazol-4-yl)methylthio]propyl]-guanidine

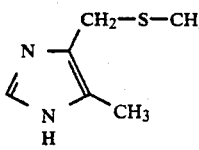 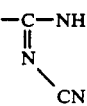 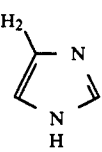

prepared by a method analogous to that of Example 39

(preliminary stage) from 1.74 g (5 mmol) of 3-[(5-methylimidazol-4-yl)methylthio]-propylamine·2HBr, 1.19 g (5 mmol) of N-cyano-diphenylimidocarbonate and 1.29 g (6.5 mmol) of 3-(imidazol-4-yl)-propylamine·2HCl Yield: 0.97 g (52%) of N-cyano-N'-[3-(imidazol-4-yl)propyl]-N''-[3-[(5-methylimidazol-4-yl)methylthio]-propyl]-guanidine·0.25 ethanol, melting range 50°–70° C.

C₁₆H₂₄N₈S·0.25 C₂H₅OH (372.0)

Calc.: C 53.27 H 6.91 N 30.12. Found: C 53.34 H 7.07 N 30.39.

¹H-NMR data (d₆-DMSO, H-D exchange with D₂O, TMS as internal standard): δ=1.65–1.85 (m) 4 H. 2.10 (s) 3 H, 2.35 2.6 (m) 4 H, 3.1–3.25 (t) 2 H, 3.25–3.55 (t) 2 H, 3.59 (s) 2 H, 6.76 (s) 1 H, 7.38 (s) 1 H, 7.51 (s) 1 H, ppm.

N-[3-(Imidazol-4-yl)propyl]-N'-[3[-(5-methylimidazol-4-yl)methylthio]propyl]-guanidine

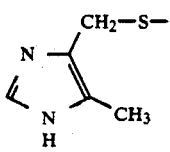  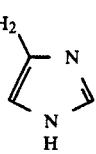

prepared by a method analogous to that of Example 39 from 0.82 g (2.2 mmol) of the previously prepared cyanoguanidine. 1.1 g of a hygroscopic foam composed of equimolar quantities of ammonium chloride and N-[3-(imidazol-4-yl)propyl]-N'[3 [(5-methylimidazol-4-yl)methylthio]propyl]-guanidine trihydrochloride are obtained as residue.

C₁₅H₂₅N₇S·3HCl·NH₄Cl (498.3).

The base is converted into the tripicrate melting at 113°–115° C. (decomposition).

C₁₅H₂₅N₇S·3C₆H₃N₃O₇·H₂O (1040.8).

Calc.: C 38.08 H 3.49 N 21.53. Found: C 37.97 H 3.71 N 21.72.

¹H-NMR data (d₆-DMSO, H-D exchange with D₂O, TMS as internal standard): δ=1.6–2.0 (m) 4 H, 2.26 (s) 3 H, 2.47 (t) 2 H, 2.69 (t) 2 H, 3.05–3.35 (m) 4 H, 3.80 (s) 2 H, 7.39 (s) 1 H, 8.65 (s) 6 H, 8.84 (s) 1 H, 8.90 (s) 1 H, ppm.

EXAMPLE 49

N-[2-(5-Methylimidazol-4-yl)ethyl]-N'-[2-[(5-methylimidazol-4-yl)methylthio]ethyl]-guanidine prepared by a method analogous to that of Example 39 from 0.69 g (2.0 mmol) of N-cyano-N'-[2-(5-methylimidazol-4-yl)ethyl]-N''-[2-[(5-methylimidazol-4-yl)methylthio]ethyl]-guanidine. 0.97 g of a hygroscopic foam composed of equimolar quantities of ammonium chloride and N-[2-(5-methylimidazol-4-yl)ethyl]-N'-[2-[(5-methylimidazol-4-yl)methylthio]ethyl]-guanidine trihydrochloride is obtained as residue.

C₁₄H₂₃N₇S·3HCl·NH₄Cl (484.3)

The base is converted into the tripicrate melting at 161°–164° C. (decomposition).

C₁₄H₂₃N₇S·3C₆H₃N₃O₇·0.5 H₂O (1017.8).

Calc.: C 37.76 H 3.27 N 22.02. Found: C 37.67 H 3.21 N 22.07.

¹H-NMR data (d₆-DMSO, H-D exchange with D₂O, TMS as internal standard): δ=2.20 (s) 3 H, 2.27 (s) 3 H, 2.61 (t) 2 H, 2.83 (t) 2 H, 2.76 (t) 2 H, 3.25–3.50 (m) 4 H, 3.90 (s) 2 H, 8.65 (s) 6 H, 8.84 (s) 1 H, 8.86 (s) 1 H, ppm.

EXAMPLE 50

N-[2-[(2-(4-Chlorobenzyl)-5-methylimidazol-4-yl)methylthio]ethyl]-N'-[3-(imidazol-4-yl)propyl]-guanidine

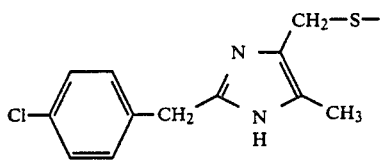

1.1 g (2 mmol) of N-Benzoyl-N'-[[2-(2-(4-chlorobenzyl)-5-methylimidazol-4-yl)methylthio]ethyl]-N''-[3-(imidazol-4-yl)propyl]-guanidine (Example 26) are heated under reflux in 50 ml of 20% hydrochloric acid for 6 hours. The product is worked up by a method analogous to that of Example 4.

Yield: 1.0 g (90%) of a hygroscopic, non-crystalline solid.

$C_{21}H_{28}ClN_7S \cdot 3HCl$ (555.4)

MS (FAB method): m/z (rel. Int. [%])=446 ([M+H]+, 39), 219 (100), 125 (46), 109 (56)

1H-NMR data (d6-DMSO, TMS as internal standard): δ=1.86 (m) 2 H, 2.24 (s) 3 H, 2.62 (t) 2 H, 2.73 (t) 2 H, 3.21 (m) 2 H, 3.38 (m) 2 H, 3.88 (s) 2 H, 4.29 (s) 2 H, 7.4–7.6 (m) 5 H, 7.68 (s) 2 H, replaceable by D2O, 7.94 (m) 1 H, replaceable by D2O, 8.12 (m) 1 H, replaceable by D2O, 9.05 (s) 1 H, ppm.

EXAMPLE 51

N-[2-[(2-Dimethylaminomethyl-5-methylimidazol-4-yl)methylthio]ethyl]-N'-[3-(imidazol-4-yl)propyl]-guanidine

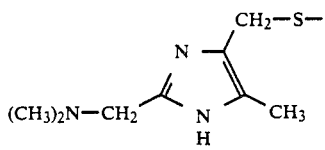

0.85 g (1.6 mmol) of N-Benzoyl-N'-[2-[(2-dimethylaminomethyl-5-methylimidazol-4-yl)methylthio]ethyl]-N''-[3-(imidazol-4-yl)propyl]-guanidine (Example 27) are heated under reflux in 50 ml of 20% hydrochloric acid for 6 hours. The product is worked up by a method analogous to that of Example 4.

Yield: 0.80 g (95%) of hygroscopic, non-crystalline solid.

$C_{17}H_{30}N_8S \cdot 4HCl$ (524.4)

MS (FAB method): m/z (rel. Int.[%])=379 ([M+H]+, 41), 334 (11), 198 (22), 153 (25), 109 (100).

1H-NMR data (d6-DMSO, TMS as internal standard): δ=1.86 (m) 2 H, 2,32 (s) 3 H, 2.66 (t) 2 H, 2.73 (t) 2 H, 2.83 (s) 6 H, 3.21 (dt) 2 H, 3.44 (dt) 2 H, 3.94 (s) 2 H, 4.53 (s) 2 H, 7.50 (s) 1 H, 7.69 (s) 2 H, replaceable by D2O, 7.93 (m) 1 H, replaceable by D2O, 8.12 (m) 1 H, replaceable by D2O, 9.05 (s) 1 H, ppm.

EXAMPLE 52

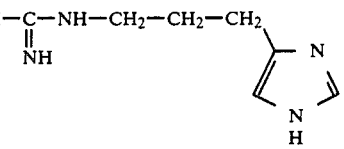

N-Benzoyl-N'-[2-hydroxy-3-(1-naphthoxy)propyl]-N''-[3-(imidazol-4-yl)propyl]-guanidine Preparation of preliminary stage 2-Benzoylimino-5-[(1-naphthoxy)methyl]-oxazolidine

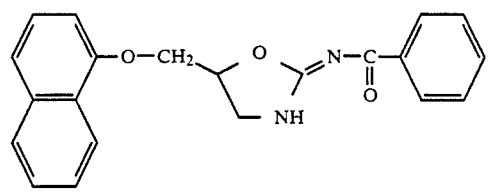

2.17 g (10 mmol) of 2-hydroxy-3-(1-naphthoxy)-propylamine and 3.17 g (10 mmol) of N-benzoyl-diphenylimidocarbonate are stirred together in 20 ml of methylene chloride at room temperature for 5 hours. The solvent is then distilled off under vacuum and the residue is crystallised from acetonitrile.

Yield: 2.32 g (67%), melting point 183° C.

$C_{21}H_{18}N_2O_3$ (346.4). Calc.: C 72.81 H 5.24 N 8.09.

Found: C 72.72 H 5.19 N 8.28.

1H-NMR data (CDCl3, TMS as internal standard): δ=4.07 (dd) 1 H, 4.16 (dd) 1 H, 4.35–4.5 (m) 2 H, 5.28 (m) 1 H, 6.81 (d) 1 H, 7.3–7.55 (m) 7 H, 7.80 (m) 1 H, 8.14 (m) 1 H, 8.26 (m) 2 H, 9.6 (broad) 1 H, replaceable by D2O, ppm.

N-Benzoyl-N'-[2-hydroxy-3-(1-naphthoxy)propyl]-N''-[3-(imidazol-4-yl)propyl]-guanidine

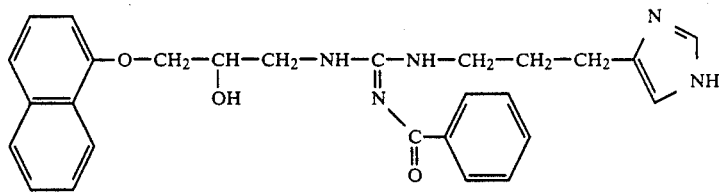

Preparation and isolation of the compound are carried out by a method analogous to that of Example 37 starting from 1.73 g (5 mmol) of 2-benzoylimino-5-[(1-naphthoxy) methyl]-oxazolidine. The oil obtained after concentration of the eluate by evaporation solidifies when stirred up with water.

Yield: 0.8 g (34%) of colourless solid which sinters at 88°–90° C.

$C_{27}H_{29}N_5O_3$ (471.6)

MS (FAB method): m/z (rel. Int. [%]) =472 ([M+H]+, 10), 44 100).

$^1$H-NMR data (d$_6$-DMSO, TMS as internal standard): δ=1.85 (m) 2 H, 2.60 (t) 2 H, 3.37 (m) 2 H, 3.57 (m) 2 H, 3.9–4.5 (m) 3 H, 5.7 (broad) 1 H, replaceable by D$_2$O, 6.6–8.4 (m) 14 H, ppm.

EXAMPLE 53

N-[2-Hydroxy-3-(1-naphthoxy)propyl]-N'-[3-(imidazol-4-yl) propyl]-guanidine

Preparation of the preliminary stages a) N-Benzoyl-N'-[2-hydroxy-3-(1-naphthoxy)propyl]-thiourea

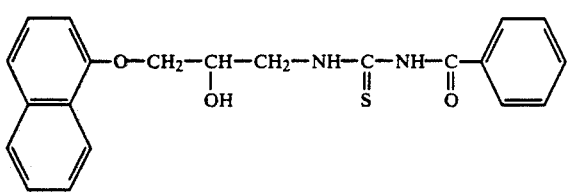

2.17 g (10 mmol) of 2-hydroxy-3-(1-naphthoxy)-propylamine and 1.63 g (10 mmol) of benzoyl isothiocyanate are heated under reflux in 120 ml of chloroform for 60 minutes. The solvent is then distilled off under vacuum and the residue is crystallised with ether and recrystallised from ethanol.

Yield: 3.4 g (89%), melting point 137° C.

$C_{21}H_{20}N_2O_3S$ (380.5). Calc.: C 66.30 H 5.30 N 7.36. Found: C 66.07 H 5.16 N 7.35.

$^1$H-NMR data (CDCl$_3$, TMS as internal standard):

δ=3.10 (d) 1 H, replaceable by D$_2$O, 4.05 (m) 1 H, 4.15–4.35 (m) 3 H, 4.56 (m) 1 H, 6.84 (d) 1 H, 7.3–7.7 (m) 7 H, 7.75–7.9 (m) 3 H, 8.27 (m) 1 H, 9.15 (s) 1 H, replaceable by D$_2$O, 11.17 (m) 1 H, replaceable by D$_2$O, ppm.

b) N-[2-Hydroxy-3-(1-naphthoxy)propyl]-thiourea

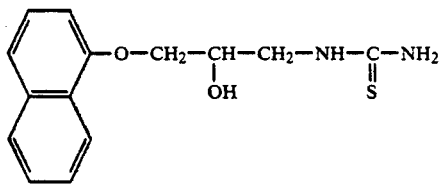

2.85 g (7.5 mmol) of N-benzoyl-N'-[2-hydroxy-3-(1-naphthoxy)propyl]-thiourea and 2.1 g of potassium carbonate are heated under reflux in a mixture of 30 ml of water and 100 ml of methanol for 60 minutes. The reaction mixture is then concentrated by evaporation under vacuum and the precipitated solid is washed with water and recrystallised from ethanol/water.

Yield: 1.82 g (88%) of colourless crystals, melting point 158° C.

$C_{14}H_{16}N_2O_2S$ (276.4). Calc.: C 60.85 H 5.84 N 10.14. Found: C 60.70 H 5.82 N 10.12.

$^1$H-NMR data (d$_6$-DMSO, TMS as internal standard): δ=3.25–3.65 (m) 2 H, 3.7–4.2 (m) 3 H, 5.47 (d) 1 H, replaceable by D$_2$O 6.96 (d) 1 H, 7.1 (broad) 2 H, replaceable by D$_2$O, 7.3–8.0 (m) 6 H, 1 H replaceable by D$_2$O, 8.30 (m) 1 H, ppm.

c) 2-Imino-5-[(1-naphthoxy)methyl]-oxazolidine

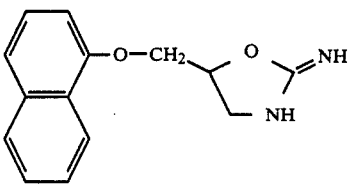

1.38 g (5 mmol) of N-[2-hydroxy-3-(1-naphthoxy)-propyl]thiourea are stirred overnight with 0.4 ml of methyl iodide in 100 ml of ethanol at room temperature. The solvent is distilled off under vacuum and the residue is recrystallised from ethanol/ether Yield: 1,57 g (85%), melting point 169° C.

$C_{14}H_{14}N_2O_2 \cdot HI$ (370.2). Calc.: C 45.42 H 3,81 N 7.57. Found: C 45.22 H 4.05 N 7.63.

$^1$H-NMR data (d$_6$-DMSO, TMS as internal standard): δ=3.87 (dd) 1 H, 4.08 (dd) 1 H, 4.45–4.6 (m) 2 H, 5.64 (m) 1 H, 7.04 (d) 1 H, 7.4–7.6 (m) 4 H, 7.92 (d) 1 H, 8.09 (d) 1 H, 9.25 (broad) 3 H, replaceable by D$_2$O, ppm.

N-[2-Hydroxy-3-(1-naphthoxy)propyl]-N'-[3-(imidazol-4-yl) propyl]-guanidine

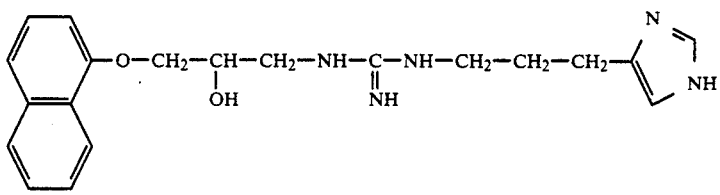

1.30 g (3.5 mmol) of 2-imino-5-(1-naphthoxy)methyl oxazolidine and 0.48 g (3.8 mmol) of 3-(imidazol-4-yl)propylamine are heated under reflux in 40 ml of anhydrous pyridine. After concentration of the reaction mixture by evaporation under vacuum, the product is isolated and purified by preparative layer chromatography (silica gel 60 PF$_{254}$, containing gypsum: solvent: chloroform/methanol 85+15, ammoniacal atmosphere). 0.85 g (49%) of the hydriodide is obtained as a hygroscopic, non-crystalline solid.

$C_{20}H_{25}N_5OS \cdot HI$ (495.4)

(MS (FAB method): m/z (rel. Int. [%])=368 ([M+H]+, 77), 351 (8), 157 (23), 109 (100).

$^1$H-NMR data (d$_6$-DMSO, TMS as internal standard): δ=1.83 (m) 2 H, 2.66 (t) 2 H, 3.22 (dt) 2 H, 3.56 (m) 2 H, 4.2–4.4 (m) 3 H, 6.99 (d) 1 H, 7.3–7.6 (m) 5 H, 7.89 (m) 1 H, 8.26 (m) 1 H, 8.75 (d) 1 H, ppm.

EXAMPLE 54

N-Benzoyl-N'-[3-(imidazol-4-yl)propyl]-N''-(2-benzyloxyethyl)-guanidine

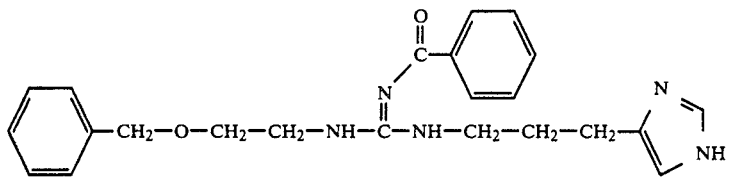

0.76 g (5 mmol) of 2-benzyloxyethylamine and 1.59 g (5 mmol) of N-benzoyl-diphenylimidocarbonate are stirred up in 20 ml of methylene chloride at room temperature for 15 minutes. The solvent is then distilled off under vacuum and the residue is taken up with 30 ml of pyridine and then heated under reflux for 60 minutes after the addition of 0.69 g (5.5 mmol) of 3-(imidazol-4-yl)-propylamine. The reaction mixture is concentrated by evaporation under vacuum and the residue is dissolved in dilute hydrochloric acid and then extracted three times with ether to remove the phenol formed in the process. After the aqueous phase has been made alkaline with ammonia, it is extracted twice with methylene chloride and the organic phase is then washed with water, dehydrated over sodium sulphate and concentrated by evaporation under vacuum. The crude product is purified by preparative layer chromatography (silica gel 60 PF$_{254}$, containing gypsum; solvent: chloroform/methanol, 99+1, ammoniacal atmosphere). 1.42 g (70%) of colourless crystals melting 117°–118° C. are obtained after crystallisation from ethyl acetate.

$C_{23}H_{27}N_5O_2$ (405.5) Calc.: C 68.13 H 6.71 N 17.27. Found: C 67.94 H 6.68 N 17.24.

IR (KBr): 1605 (C=O) cm$^1$.

$^1$H-NMR data (CDCl$_3$, TMS as internal standard); δ=1.75 (m) 2 H, 2.56 (t) 2 H, 3.2–3.9 (m) 6 H, 4.57 (s) 2 H, 6.71 (s) 1 H, 6.9–7.6 (m) 9 H, 8.16 (m) 2 H, ppm.

EXAMPLE 55

N-(2-Benzyloxyethyl-N'-[3-(imidazol-4-yl)propyl]-guanidine

Preparation of preliminary stages a) N-Benzoyl-N'-(2-benzyloxyethyl)-thiourea

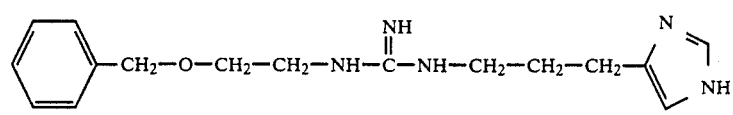

1.51 g (10 mmol) of 2-benzyloxyethylamine and 1.63 g (10 mmol) of benzoyl isothiocyanate are heated under reflux in 120 ml of chloroform for 30 minutes. The solvent is then distilled off under vacuum and the oily residue is crystallised with ether.

Yield: 2.97 g (95%), melting point 89°–90° C. (ether).

$C_{17}H_{18}N_2O_2S$ (314.4) Calc.: C 64.94 H 5.77 N 8.91. Found: C 65.00 H 5.81 N 8.76.

MS: m/z (rel. Int. [%])=314 (M+, 3), 105 (100), 91 (96), 77 (83).

$^1$H-NMR data (CDCl$_3$, TMS as internal standard): δ=3.74 (t) 2 H, 3.95 (dt) 2 H, 4.61 (s) 2 H, 7.25–7.7 (m) 8 H, 7.86 (m) 2 H, 9.05 (broad) 1 H, replaceable by D$_2$O, 11.0 (broad) 1 H, replaceable by D$_2$O, ppm.

b) N-(2-Benzyloxyethyl-S-methyl-isothiouronium iodide

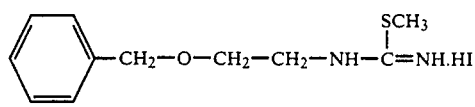

2.36 g (7.5 mmol) of N-benzoyl-N'.(2-benzyloxyethyl)thiourea and 2.1 g of potassium carbonate are together heated under reflux in a mixture of 30 ml of water and 100 ml of methanol for 40 minutes. The reaction mixture is then concentrated by evaporation under vacuum and the residue is taken up with ether and washed three times with water. The organic phase is dehydrated over sodium sulphate and concentrated by evaporation under vacuum, and the oily residue is taken up with 100 ml of ethanol and then stirred overnight at room temperature after the addition of 0.6 ml of methyl iodide. The solvent is distilled off under vacuum and the residue is stirred up with acetone and ether. 2.40 g (91%) of the isothiouronium salt is obtained as a colourless solid melting at 116°–117° C.

$C_{11}H_{16}N_2OS·HI$ (352.2). Calc.: C 37.5 H 4.87 N 7.95. Found: C 37.33 H 4.91 N 7.76.

IR (KBr): 1655 (C=N+) cm$^{-1}$.

$^1$H-NMR data (d$_6$-DMSO, TMS as internal standard): δ=2.60 (s) 3 H, 3.45–3.65 (m) 4 H, 4.52(s) 2 H, 7.35 (m) 5 H. 9.2 (broad) 3 H, replaceable by D$_2$O, ppm.

N-(2-Benzyloxyethyl)-N'-[3-(imidazol-4-yl)propyl]-guanidine

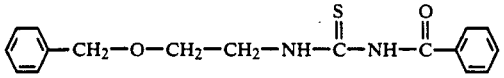

1.76 g (5 mmol) of N-(2-Benzyloxyethyl)-S-methylisothiouronium iodide and 0.69 g (5 mmol) of 3-(imidazol-4-yl)propylamine are heated under reflux in 40 ml of anhydrous pyridine for 3 hours. After concentration of the reaction mixture by evaporation under vacuum, the reaction product is isolated and purified by preparative layer chromatography (silica gel 60 PF$_{254}$, containing gypsum: solvent: chloroform/methanol 85:15, ammoniacal atmosphere). 1.5 g (70%) of N-(2-benzyloxyethyl)-N'-[3-(imidazol-4-yl)propyl]-guanidine hydriodide are obtained as a viscous oil.

$C_{16}H_2N_5O·HI$ (429.3)

MS: m/z (rel. Int. [%])=301 (M+, 1), 128 (70), 127 (40), 95 (44), 91 (100), 81 (38).

$^1$H-NMR data (d$_6$-DMSO, TMS as internal standard): δ = 1.79 (m) 2 H, 2.59 (t) 2 H, 3.20 (dt) 2 H, 3.40 (dt) 2 H, 3.55 (t) 2 H, 4.53 (s) 2 H, 6.94 (m) 1 H, 7.25–7.45 (m) 5 H, 7.85 (d) 1 H, ppm.

The dipicrate melts at 131°–133° C. after recrystallisation from ethanol.

$C_{16}H_{23}N_5O \cdot 2C_6H_3N_3O_7$ (759.6).
Calc.: C 44.27 H 3.85 N 20.28. Found: C 44.03 H 3.85 N 20.12.

EXAMPLE 56

N-Benzoyl-N'-[3-(imidazol-4-yl)propyl]-N"-(2-benzylthioethyl)-guanidine

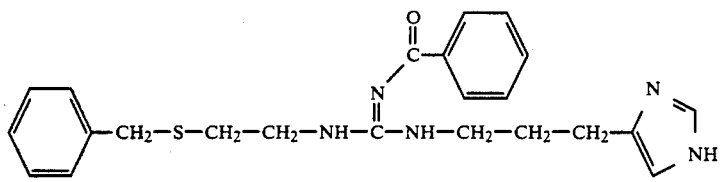

The method of preparation is analogous to that of Example 54 starting from 0.84 g (5 mmol) and 2-benzylthioethylamine.

Yield: 1.53 g (73%); melting point 133°–134° C. (ethyl acetate).

$C_{23}H_{27}N_5OS$ (421 6) Calc.: C 65.53 H 6.46 N 16.61. Found: C 65.50 H 6.46 N 16.60.

$^1$H-NMR data (CDCl$_3$, TMS as internal standard): δ = 1.94 (m) 2 H, 2.69 (t) 2 H, 2.73 (t) 2 H, 3.2–3.7 (m) 4 H, 3.77 (s) 2 H, 6.78 (s) 1 H, 7.05–7.5 (m) 9 H, 8.20 (m) 2 H, ppm.

EXAMPLE 57

N-Benzoyl-N'-[3-(imidazol-4-yl)propyl]-N"-[2-[(naphth-1-yl) methylthio]ethyl]-guanidine

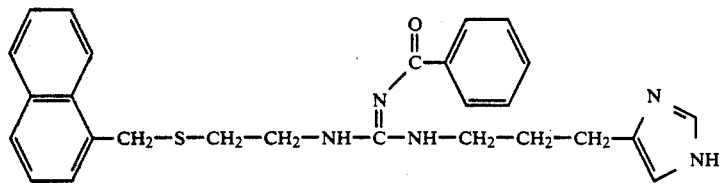

The method of preparation is analogous to that of Example 54 starting from 1.09 g (5 mmol) of 2-[(naphth-1-yl)methylthio]-ethylamine.

Yield: 1.5 g (64%), melting point 128°–130° C. (ethyl acetate).

$C_{27}H_{29}N_5OS$ (471.6) Calc. C 68.76 H 6.20 N 14.85. Found: C 68.70 H 6.16 N 14.82.

IR (KBr): 1605 (C=O) cm$^{-1}$.

$^1$H-NMR data (CDCl$_3$, TMS as internal standard): δ = 1.83 (m) 2 H, 2.67 (t) 2 H, 2.78 (t) 2 H, 3.32 (dt) 2 H, 3.62 (dt) 2 H, 4.20 (s) 2 H, 6.71 (s) 1 H. 7.1–8.4 (m) 13 H, ppm.

EXAMPLE 58

N-[3-(Imidazol-4-yl)propyl]-N'-[2-[(naphth-1-yl)methylthio]ethyl]-guanidine

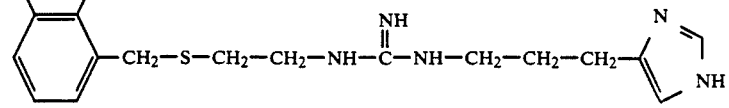

0.85 g (1.8 mmol) of N-Benzoyl-N'-[3-(imidazol-4-yl)propyl]-N"-[2-[(naphth-1-yl)methylthio]ethyl]-guanidine (Example 57) are heated under reflux in 45 ml of 20% hydrochloric acid for 7 hours. When the reaction mixture has cooled, the benzoic acid formed is removed by extraction with ether, the aqueous phase is evaporated to dryness under vacuum and the residue is dried in a high vacuum. 0.72 g (91%) of dry, highly hygroscopic foam is obtained.

$C_{20}H_{25}N_5S \cdot 2HCl$ (440.4) Molar mass (MS): Calc.: 367.18307. Found: 367.18191.

MS: m/z (rel. Int. [%]) = 367 (M.+, 2), 242 (30), 226 (9), 141 (84), 95 (32).

$^1$H-NMR data (d$_6$-DMSO, TMS as internal standard): δ = 1.85 (m) 2 H, 2.4–3.0 (m) 4 H, 3.0–3.7 (m) 4 H, 4.30 (s) 2 H. 7.2–8.4 (m) 12 H, 4 H replaceable by D$_2$O, 8.86 (d) 1 H, ppm.

EXAMPLE 59

N-Benzoyl-N'-3-(imidazol-4-yl)propyl]-N"-[2-[(1-phenylethyl)thio]ethyl]-guanidine Preparation of the preliminary stage a) 2-[(1-Phenylethyl)thio]-ethylamine

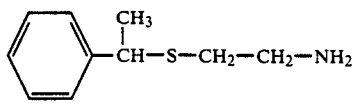

5.68 g (50 mmol) of cysteamine hydrochloride are introduced under a current of nitrogen into a solution of 2.3 g (0.1 mol) of sodium in 150 ml of methanol, and 9.25 g (50 mmol) of 1-phenylethylbromide in 30 ml of methanol are then added dropwise. The reaction mixture is stirred at room temperature for one hour, the solvent is distilled off under vacuum and the residue is dissolved in 5% hydrochloric acid and extracted with ether. After adjustment to an alkaline pH with 15% sodium hydroxide solution, the aqueous phase is extracted by shaking with methylene chloride and the organic phase is washed with water, dehydrated over sodium sulphate and concentrated by evaporation under vacuum. 6.65 g (73%) of an oil which is sufficiently pure for further reactions are obtained as residue. Boiling point 77°-79° C./0.25 mm.

C$_{10}$H$_{15}$NS (181.3)

$^1$H-NMR data (CDCl$_3$, TMS as internal standard): δ=1.58 (d) 3 H, 2.43 (m) 2 H, 2.74 (t) 2 H, 3.97 (q) 1 H, 7.2–7.4 (m) 5 H, ppm.

The hydrochloride melts at 135°–136° C. after recrystallisation from ethanol/ether.

C$_{10}$H$_{15}$NS·HCl (217.8) Calc.: C 55.16 H 7.41 N 6.43. Found:C 55.24 H 7.62 N 6.38.

N-Benzoyl-N'-[3-(imidazol-4-yl)propyl]-N''-[2-[(1-phenylethyl)thio]ethyl]-guanidine

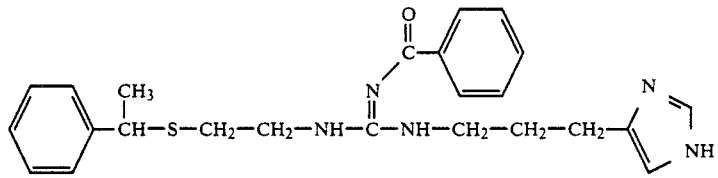

The method of preparation is analogous to that of Example 54 from 0.91 g (5 mmol) of 2-[(1-phenylethyl)-thio]ethylamine.

Yield: 1.6 g (73%), melting point 128°-130° C. (ethyl acetate)

C$_{24}$H$_{29}$N$_5$OS (435.6). Calc.: C 66.18 H 6.71 N 16.08. Found: C 65.99 H 6.73 N 15.88.

MS m/z (rel.Int. [%])=435 (M.+, 1,), 109 (23), 105 (100), 95 (24), 77 (69).

$^1$H-NMR data (CDCl$_3$, TMS as internal standard): δ=1.56 (d) 3 H, 1.91 (m) 2 H, 2.55–2.75 (m) 4 H, 3.37 (m) 2 H, 3.60 (m) 2 H, 4.03 (q) 1 H, 6.75 (s) 1 H, 7.1–7.5 (m) 9 H, 8.20 (m) 2 H, ppm.

EXAMPLE 60

N-[3-(Imidazol-4-yl)propyl]-N'-[2-[(1-phenylethyl)thio ethyl]-guanidine

The method of preparation is analogous to that of Example 55 starting from 1.81 g (10 mmol) of 2-[(1-phenylethyl)thio]-ethylamine (Example 59 a).

Preliminary stages a) N-Benzoyl-N'-[2-[(1-phenylethyl)thio]ethyl]-thiourea

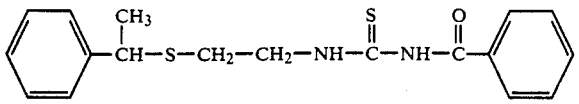

Yield: 3.13 g (91%), melting point 72°–73° C. (ether/petroleum ether)

C$_{18}$H$_{20}$N$_2$OS$_2$ (344.5). Calc.: C 62.76 H 5.85 N 8.13. Found: C 62.57 H 5.89 N 7.95.

MS: m/z (rel. Int. [%])=344 (M.+, 1), 239 (100), 105 (96).

$^1$H-NMR data (CDCl$_3$, TMS as internal standard): δ=1.61 (d) 3 H, 2.66 (t) 2 H, 3.78 (dt) 2 H, 4.07 (q) 1 H, 7.15–7.7 (m) 8 H, 7.85 (m) 2 H, 8.98 (broad) 1 H, replaceable by D$_2$O, 10.9 (broad) 1 H, replaceable by D$_2$O, ppm.

b) S-Methyl-N-[2-[(1-phenylethyl)-thio]ethyl]-isothiouronium iodide

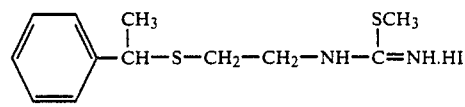

2.44 g (85%) of an oil sufficiently pure for further reactions are obtained from 2.58 g (7.5 mmol) of N-benzoyl-N'-2-[(1-phenylethyl)thio]ethyl]-thiourea.

C$_{12}$H$_{18}$N$_2$S$_2$·HI (382.3) Molar mass(MS):

Calc.: 254.09115, Found: 254.09119.

MS: m/z (rel. Int. [%])=254 (M.+, 6), 149 (100) 128([HI]+, 38), 105 (94).

$^1$NMR data (d$_6$-DMSO, TMS as internal standard): δ=1.50 (d) 3 H, 2.4–2.7 (m) 2 H, 2.60 (s) 3 H, 3.4 (m) 2 H, 4.11 (q) 1 H, 7.33 (m) 5 H, ppm.

N-[3-(Imidazol-4-yl)propyl]-N'-[2-[(1-phenylethyl)thio]ethyl]-guanidine

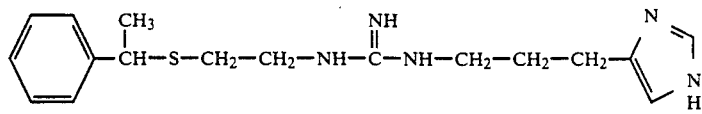

1.4 g (61%) of the guanidine hydriodide are obtained in the form of a viscous oil from 1.91 9 (5 mmol) of S-methyl-N-[2-[(1-phenylethyl)thio]ethyl]-isothiouronium iodide.

C$_{17}$H$_{25}$N$_5$S·HI (459.4)

MS: m/z (rel. Int. [%])=332 ([M+H]+43), 109 (46), 105 (100) (FAB method).

$^1$H-NMR data (d$_6$-DMSO, TMS as internal standard): δ=1.51 (d) 3 H, 1.78 (m) 2 H, 2.25–2.8 (m) 4 H, 2.9–3.5 (m) 4 H, 4.11 (q) 1 H, 7.04 (m) 1 H, 7.1–7.7 (m) 9 H, 4 H replaceable by D₂O, 8.11 (d) 1 H, ppm.

EXAMPLE 61

N-Benzoyl-N'-[3-(imidazol-4-yl)propyl]-N''-[2-[(p-methyl-α-phenylbenzyl)thio]ethyl]-guanidine Preparation of the preliminary stage 2-[(p-Methyl-α-phenylbenzyl)thio]-ethylamine

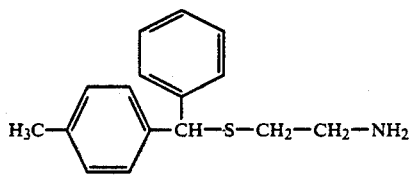

9.41 g (50 mmol) of 4-Methylbenzhydrol and 5.68 g (50 mmol) of cysteamine hydrochloride are heated under reflux for one hour in 100 ml of isopropyl alcohol with the addition of 10 ml of conc. hydrochloric acid. The solvent is then evaporated off under vacuum and the residue is diluted with water and extracted by shaking twice with ether. After the pH has been adjusted to alkaline with 10% sodium hydroxide solution, the aqueous phase is extracted twice with ether and the ethereal solution is washed with water, dehydrated over sodium sulphate and concentrated by evaporation under vacuum. 9.4 g (73%) of an oil sufficiently pure for further reactions are obtained.

C₁₆H₁₉NS (257.4)

MS: m/z (rel. Int. [%])=257 (M.⁺, 2), 181(100) 166(38).

¹H-NMR data (CDCl₃, TMS as internal standard): δ=2,32 (s) 3 H, 2.51 (t) 2 H, 2.81 (t) 2 H, 5.14 (s) 1 H, 7.0–7.45 (m) 9 H, ppm.

The hydrochloride melts at 133°–135° C. after recrystallisation from acetone/ether.

C₁₀H₁₉NS·HCl (293.9). Calc.: C 65.40 H 6.85 N 4.77. Found: C 65.49 H 6.85 N 4.61.

N-Benzoyl-N'-[3-(imidazol-4-yl)propyl]-N''-[2-[(p-methyl-α-phenylbenzyl)thio]ethyl]-guanidine

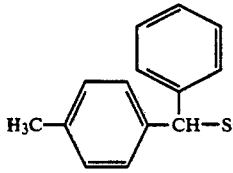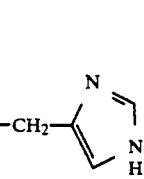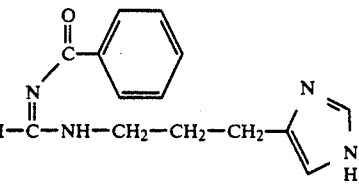

The compound is prepared by a method analogous to that of Example 54 from 1.29 g (5 mmol) of 2-[(p-methyl-α-phenylbenzyl)thio]-ethylamine. After removal of the pyridine by evaporation under vacuum, 1.6 g (63%) of colourless solid crystallise after the addition of ethanol. After recrystallisation from ethanol, this product melts at 155°–156° C.

C₃₀H₃₃N₅OS (511.7). Calc.: C 70.42 H 6.50 N 13.69. Found: C 70.27 H 6.56 N 13.51.

MS: m/z (rel. Int. [%])=511 (M.⁺, 1), 181(81), 166(25), 109(12), 105(100).

¹H-NMR data (CDCl₃, TMS as internal standard): δ=1.90 (m) 2 H, 2.29 (s) 3 H, 2.65 (t) 2 H, 2.70 (t) 2 H, 3.35 (broad) 2 H, 3.65 (broad) 2 H, 5.22 (s) 1 H, 6.73 (s) 1 H, 7.0–7.5 (m) 13 H, 8.20(m) 2 H, ppm.

EXAMPLE 62

N-[3-(Imidazol-4-yl)propyl]-N'-[2-[(p-methyl-α-phenylbenzyl) thio]ethyl]-guanidine The compound is prepared and isolated by a method analogous to that of Example 55, starting from 2.57 g (10 mmol) of 2-[(p-methyl-a-phenylbenzyl)thio]-ethylamine.

Preliminary stages a) N-Benzoyl-N'-[2-[(p-methyl-a-phenylbenzyl)thio]ethyl]thiourea

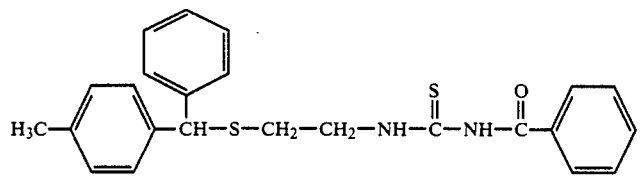

Yield: 3.7 g (88%), melting point 94°–95° C. (ether/petroleum ether)

C₂₄H₂₄N₂OS₂ (420.6) Calc.: C 68.54 H 5.75 N 6.66. Found: C 68.37 H 5.77 N 6.61.

MS: m/z (rel.Int. [%])=239 ([M-C₁₄H₁₃]⁺, 90), 181(100), 105(90).

¹H-NMR data (CDCl₃, TMS as internal standard): δ=2.32 (s) 3 H, 2.75 (t) 2 H, 3.86 (dt) 2 H, 5.28 (s) 1 H, 7.0–7.7 (m) 12 H, 7.85 (m) 2 H, 9.0 (broad) 1 H, replaceable by D₂O, 10.95 (broad) 1 H, replaceable by D₂O, ppm.

b) S-Methyl-N-[2-[(p-methyl-α-phenylbenzyl)thio]ethyl]isothiouronium iodide

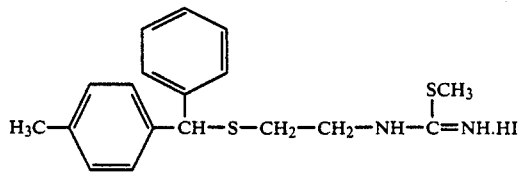

3.15 g (7.5 mmol) of N-benzoyl-N'-[2-[(p-methyl-α-phenylbenzyl)thio]ethyl]-thiourea yield 2.85 g (83%) of the isothiouronium salt in the form of an oil which is sufficiently pure for further reaction $C_{18}H_{22}N_2S_2 \cdot HI$ (458.4) Molar mass (MS):
Calc.: 330.12245; Found: 330.12217.

MS: m/z (rel Int. [%])=330 (M.+,9) 254(5), 181(90), 149(100).

$^1$H-NMR data (d$_6$-DMSO, TMS as internal standard): δ=2.26 (s) 3 H, 2.4–2 7 (m) 2 H, 2.60 (s) 3 H, 3.50 (m) 2 H, 5.39 (s) 1 H, 7.0–7.6 (m) 9 H, ppm.

N-[3-(Imidazol-4-yl)propyl]-N'-[2-[(p-methyl-α-phenylbenzyl)thio]ethyl]-guanidine

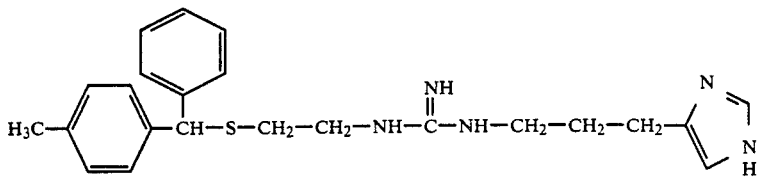

2.29 g (5 mmol) of N-[2-[(p-methyl-α-phenylbenzyl)-thio]ethyl]-S-methyl-isothiouronium iodide yield 1.5 (56%) of the guanidine hydriodide in the form of a dry foam.

$C_{23}H_{29}N_5S \cdot HI$ (535.5)

MS: m/z (rel.Int. [%])=408 ([M+H]+, 25) 181(100), 109(32) (FAB method).

$^1$H-NMR data (d$_6$-DMSO, TMS as internal standard): δ=1.77 (m) 2 H, 2.26 (s) 3 H, 2.3–2.7 (m) 4 H, 2.9–3.6 (m) 4 H, 5.36 (s) 1 H, 6.91 (m) 1 H, 7.0–7.7 (m) 13 H, 4 H replaceable by D$_2$O, 7.84 (d) 1 H, ppm.

EXAMPLE 63

N-Benzoyl-N'-[3-(imidazol-4-yl)propyl]-N''-[2-(p-chlorobenzylthio)ethyl]-guanidine

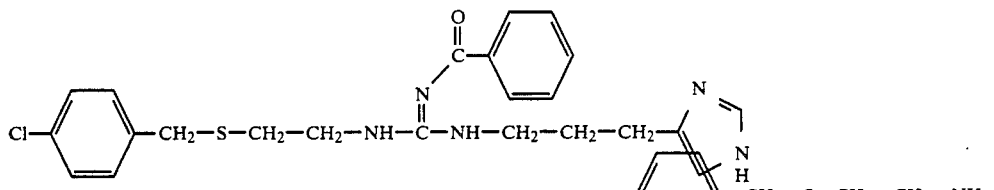

The method of preparation is analogous to that of Example 54, starting from 1.01 g (5 mmol) of 2-(p-chlorobenzylthio)-ethylamine.

Yield: 1.14 g (50%), melting point 128° C. (acetonitrile)

$C_{23}H_{26}ClN_5OS$ (456.0). Calc.: C 60.58 H 5.75 N 15.36. Found: C 60.79 H 5.84 N 15.36.

MS: m/z (rel. Int. [%]) =455 (M+.,2) , 330(60), 125(95), (100), 95(90).

$^1$H-NMR data (CDCl$_3$, TMS as internal standard): δ=1.93 (m) 2 H, 2.69 (t) 2 H, 2.71 (t) 2 H, 3.2–3.7 (m) 4 H, 3.73 (s) 2 H, 6.82 (s) 1 H, 7.2–7.6 (m) 8 H, 8.23 (m) 2 H, ppm.

EXAMPLE 64

N-[3-(Imidazol-4-yl)propyl]-N'-[2-(p-chlorobenzylthio) ethyl]-guanidine

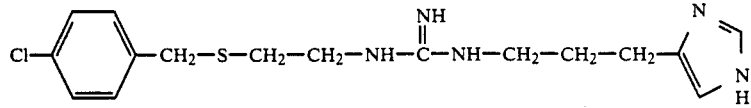

The method of preparation is analogous to that of Example 58, starting from 0.82 g (1.8 mol) of N-benzoyl-N'-[3-(imidazol-4-yl)propyl]-N''-[2-(p-chlorobenzylthio) ethyl]-guanidine (Example 63).

Yield: 0.28 g (37%) of a dry, highly hygroscopic foam $C_{16}H_{22}ClN_5S \cdot 2ClN_5S \cdot 2HCl$ (424.8)

MS: m/z (rel. Int. [%])=352 ([M+H]+100), 125(96), 109(85) (FAB method)

$^1$H-NMR data (d$_6$-DMSO, TMS as internal standard): δ=1.86 (m) 2H, 2.55 (m) 2 H, 2.78 (m) 2 H, 3.4–3.6 (m) 4 H, 3.85 (s) 2 H, 7.39 (m) 4 H, 7.55 (m) 1 H, 7.74 (s) 2 H, replaceable by D$_2$O, 7.95 (t) 1 H, replaceable by D$_2$O, 8.18 (t) 1 H, replaceable by D$_2$O, 9.12 (d) 1 H, ppm

EXAMPLE 65

N-Benzoyl-N'-[3-(imidazol-4-yl)propyl]-N''-[2-(m-chlorobenzylthio)ethyl]-guanidine Preparation of the preliminary stage 2-(m-Chlorobenzylthio)-ethylamine

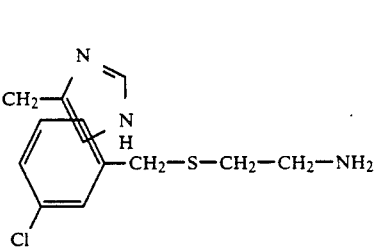

5.68 g (50 mmol) of cysteamine hydrochloride are introduced into a solution of 2.3 g (0.1 mol) of sodium in 60 ml of ethanol, followed by the addition of 8.05 g (50 mmol) of m-chlorobenzyl chloride. The reaction mixture is heated under reflux for one hour and the solvent is distilled off under vacuum. Water is added to the residue and the residue is extracted with ether. The organic phase is extracted with 5N-hydrochloric acid. After adjustment of the pH to alkaline with aqueous ammonia, the aqueous phase is extracted by shaking with ether and the organic phase is washed with water, dehydrated over sodium sulphate and concentrated by evaporation under vacuum. 8.2 g (81%) of an oil sufficiently pure for further reactions are obtained as residue. Boiling point 96°–98° C./0.2 mm.

C₉H₁₂ClNS (201.7)

¹H-NMR data (CDCl₃, TMS as internal standard): δ=2.50 (m) 2 H, 2.85 (m) 2 H, 3.67 (s) 2 H, 7.1–7.4 (m) 4 H, ppm.

N-Benzoyl-N'-[3-(imidazol-4-yl)propyl]-N''-2-(m-chlorobenzylthio)ethyl]-guanidine The method of preparation is analogous to that of Example 54, starting from 1.01 g (5 mmol) of 2-(m-chlorobenzylthio)-ethylamine.

Yield: 0.95 g (42%), melting point 122° C. (acetonitrile)

C₂₃H₂₆ClN₅OS (456.0). Calc.: C 60.58 H 5.75 N 15.36. Found: C 60.31 H 5.69 N 15.24.

MS: m/z (rel. Int. [%])=455 (M.⁺, 5), 330(60), 125(90), 105(100), 95(93).

¹H-NMR data (CDCl₃, TMS as internal standard): δ=1.95 (m) 2 H, 2.6–2.8 (m) 4 H, 3.2–3.6 (m) 4 H, 3.71 (s) 2 H, 6.78 (s) 1 H, 7.1–7.55 (m) 8 H, 8.18 (m) 2 H, ppm.

EXAMPLE 66

N-[3-(Imidazol-4-yl)propyl]-N'-[2-(m.chlorobenzylthio)ethyl]-guanidine

The method of preparation is analogous to that of Example 58, starting from 0.82 g (1.8 mmol) of N-benzoyl-N'-[3-(imidazol-4-yl)propyl]-N''-[2-(m-chlorobenzylthio) ethyl]-guanidine (Example 65).

Yield 0.16 g (21%) of a dry, highly hygroscopic foam.

C₁₆H₂₂ClN₅S.2HCl (424.8)

MS: m/z (rel. Int.) [%])=352([M+H]⁺, 53), 125(100), 109(70) (FAB method).

¹H-NMR data (d₆-DMSO, TMS as internal standard): δ=1.84 (m) 2 H, 2.54 (t) 2 H, 2.71 (t) 2 H, 3.1–3.6 (m) 4 H, 3.82 (s) 2 H, 7.3–7.5 (m) 5 H, 7.58 (s) 2 H, replaceable by D₂O, 7.69 (t) 1 H, replaceable by D₂O, 7.91 (t) 1 H, replaceable by D₂O, 9.00 (d) 1 H, ppm.

EXAMPLE δ

N-Benzoyl-N'-[3-(imidazol-4-yl)propyl]-N''-[2-(p-methylbenzylthio)ethyl]-guanidine Preparation of the preliminary stage 2-(p-Methylbenzylthio)-ethylamine The method of preparation is analogous to that of Example 65, starting from 7.03 g (50 mmol) of p-methylbenzyl chloride.

Yield: 7.08 g (78%) of an oil sufficiently pure for further use.

C₁₀H₁₅NS (181.3)

¹H-NMR data (CDCl₃, TMS as internal standard): δ=2.32 (s) 3 H, 2.53 (t) 2 H, 2.82 (t) 2 H, 3.66 (s) 2 H, 7.1–7.3 (m) 4 H, ppm.

N-Benzoyl-N'-[3-(imidazol-4-yl)propyl]-N''-2-(p-methylbenzylthio)ethyl]-guanidine The method of preparation is analogous to that of Example 54, starting from 0.91 g (5 mmol) of 2-(p-methylbenzylthio)-ethylamine.

Yield: 1.01 g (46%), melting point 155° C. (acetonitrile).

C₂₄H₂₉N₅OS (435.6). Calc.: C 66.18 H 6.71 N16.08. Found: C 65.90 H 6.77 N 16.07.

MS: m/z (rel. Int. [%])=435 (M⁺,43), 330 (100), 105 (6).

¹H-NMR data (CDCl₃, TMS as internal standard): δ=1.96 (m) 2 H, 2.32 (s) 3 H, 2.65–2.8 (m) 4 H, 3.4 (broad) 2 H, 3.7 (broad) 2 H, 3.74 (s) 2 H, 6.78 (s) 1 H, 7.06–7.50 (m) 8 H, 8.19 (m) 2 H, ppm.

EXAMPLE 68

N-[3-(Imidazol-4-yl)propyl]-N'-[2-(p-methylbenzylthio) ethyl]-guanidine

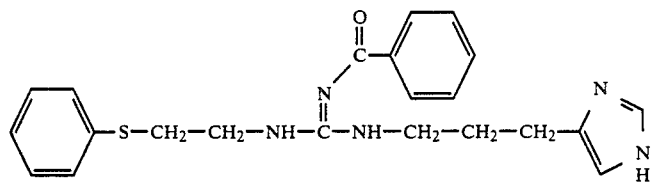

The method of preparation is analogous to that of Example 58, starting from 0.78 g (1.8 mmol) of N-benzoyl-N'-[3-(imidazol-4-yl)propyl]-N''-[2-(p-methylbenzylthio) ethyl]-guanidine (Example 67).

Yield: 0.21 g (29%) of a dry, highly hygroscopic foam.

$C_{17}H_{25}N_5S \cdot 2HCl$ (404.4)

MS: m/z (rel. Int. [%])=332 (([M+H]+,26), 109(27), 1H-NMR data (d$_6$-DMSO, TMS as internal standard): δ=1.86 (m) 2 H, 2.28 (s) 3 H, 2.52 (m) 2 H, 2.72 (t) 2 H, 3.20 (m) 2 H, 3.38 (m) 2 H, 3.77 (s) 2 H, 7.05–7.25 (m) 4 H, 7.43 (m) 1 H, 7.58 (s) 2 H, replaceable by D$_2$O, 7.74 (t) 1 H, replaceable by D$_2$O, 7.95 (t) 1 H, replaceable by D$_2$O, 8.95 (d) 1 H, ppm.

EXAMPLE 69

N-Benzoyl-N'-[3-(imidazol-4-yl)propyl]-N''-(2-phenylthioethyl)-guanidine

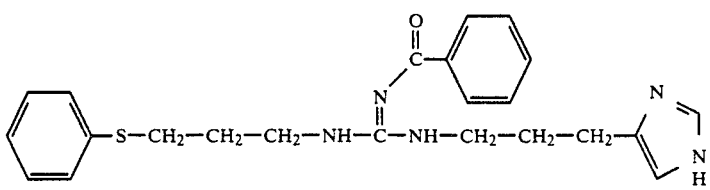

The method of preparation is analogous to that of Example 54, starting from 0.77 g (5 mmol) of 2-phenylthioethylamine After evaporation of the pyridine, the residue is crystallised by stirring with ether. The crude product is freed from phenol adhering to it by repeatedly stirring it with ether, and is then dissolved in dilute hydrochloric acid and reprecipitated by alkalization with ammonia, and finally recrystallised from ethanol.

Yield: 1.9 g (93%), melting point 156°–158° C.

$C_{22}H_{25}N_5OS$ (407.5). Calc.: C 64.84 H 6.18 N 17.18. Found: C 64.42 H 6.19 N 16.98.

MS: m/z (rel. Int. [%]) =407 (M.+,3), 190(25),137(13), 124(27) 109(32), 105(100), 95(30);81(25), 77(57), 58(53), 43(54)

1H-NMR data (d$_6$-DMSO, TMS as internal standard): δ=1.83 (m) 2 H, 2.58 (t) 2 H, 2.9–3.8 (m) 6 H, 6.77 (s) 1 H, 7.0–7.7 (m) 9 H, 8.07 (m) 2 H, ppm.

EXAMPLE 70

N-[3-(Imidazol-4-yl)propyl]-N'-(2-phenylthioethyl)-guanidine

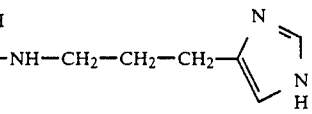

0.82 g (2 mmol) of N-benzoyl-N'-[3-(imidazol 4-yl)propyl]-N''-(2-phenylthioethyl)-guanidine are heated under reflux in 18% hydrochloric acid for 7 hours and then worked up by a method analogous to that of Example 58. 0.72 g (96%) of a dry, hygroscopic foam is obtained.

$C_{15}H_{21}N_5S \cdot 2HCl$ (376.4) Molar mass(MS):
Calc.: 303.15177, Found 303.15214.

MS: m/z (rel. Int. [%])=303 (M.+,10) 178(42), 124(96), 110(100), 109(46), 95(54).

1H-NMR data (d$_6$-DMSO, TMS as internal standard): δ=1.85 (m) 2 H, 2.75 (t) 2 H, 2.9–3.7 (m) 6 H, 7.0–7.55 (m) 6 H, 7.61 (s) 2 H, replaceable by D$_2$O, 8.00 (t) 1 H, replaceable by D$_2$O, 8.16 (t) 1 H, replaceable by D$_2$O, 8.99 (d) 1 H, ppm.

EXAMPLE 71

N-Benzoyl-N'-[3-(imidazol-4-yl)propyl]-N''-[(3-phenylthio)propyl]-guanidine

The compound is prepared by a method analogous to that of Example 54 from 0.84 g (5 mmol) of 3-phenylthiopropylamine. After removal of the pyridine by evaporation under vacuum, the residue is crystallised by stirring with ether. The crude product is repeatedly stirred up with ether, reprecipitated from ethanol/water and finally recrystallised from ethyl acetate.

Yield: 1.86 g (88%), melting point 130°–132° C.

C$_{23}$H$_{27}$N$_5$OS (421.6) Calc.: C 65.53 H 6.46 N 16.61. Found: C 65.27 H 6.49 N 16.59.

MS: m/z (rel. Int. [%])=421 (M+,1),109 (20), 105(10), 95(30), 58(100).

$^1$H-NMR data (CDCl$_3$, TMS as internal standard): δ=1.6–2.3 (m) 4 H, 2.66 (t) 2 H, 3.09 (t) 2 H, 3.15–3.75 (m) 4 H, 6.79 (s) 1 H, 6.9–7.6 (m) 9 H, 8.22 (m) 2 H, ppm.

EXAMPLE 72

N-[3-(Imidazol-4-yl)propyl]-N'-(3-phenylthiopropyl)-guanidine

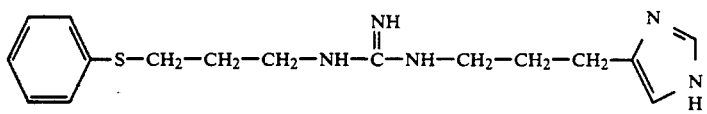

0.84 g (2 mmol) of N-benzoyl-N'-[3-(imidazol-4-yl)propyl]-N''-(3-phenylthiopropyl)-guanidine are heated under reflux in 18% hydrochloric acid for 7 hours and then worked up by a method analogous to that of Example 58. 0.71 g (91%) of a dry, hygroscopic foam is obtained.

C$_{16}$H$_{23}$N$_5$S.2HCl (390.4) Molar mass(MS): Calc.: 317.16742, Found 317.16675

MS: m/z (rel. Int. [%]) =317 (M.+,6), 192(10), 167(87), 109(65), 95(100).

$^1$H-NMR data (d$_6$-DMSO, TMS as internal standard): δ=1.5–2.2 (m) 4 H, 2.4–3.6 (m) 8 H, 7.0–7.5 (m) 6 H, 7.61 (s) 2 H, replaceable by D$_2$O. 7.8–8.3 (m) 2 H, replaceable by D$_2$O, 9.00 (d) 1 H, ppm.

EXAMPLE 73

N-Benzoyl-N'-[3-(imidazol-4-yl)propyl]-N''-(4-phenylbutyl)-guanidine

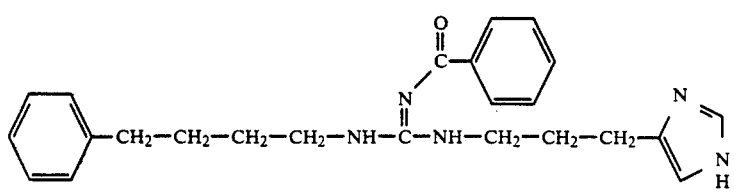

The method of preparation is analogous to that of Example 54, starting from 0.75 g (5 mmol) of 4-phenylbutylamine.

Yield: 1.05 g (52%), m.p. 132° C. (acetonitrile).

C$_{24}$H$_{29}$N$_5$O (403.5)

MS: m/z (rel. Int. [%]) =403 (M.+, 6), 109(17), 105(100), 95(17), 91(30).

$^1$H-NMR data (CDCl$_3$, TMS as internal standard): δ=1.6–2.1 (m) 6 H, 2.67(m) 4 H, 3.1–3.8 (m) 4 H, 6.74 (s) 1 H. 7.1–7.55 (m) 9 H, 8.19 (m) 2 H, ppm.

EXAMPLE 74

N-[(3-Imidazol-4-yl)propyl]-N'-(4-phenylbutyl)-guanidine

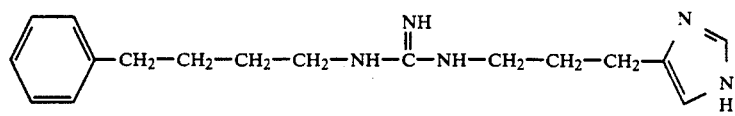

0.8 g (2 mmol) of N-benzoyl-N'-[3-(imidazol-4-yl)propyl]-N''-(4-phenylbutyl)-guanidine are heated under reflux in 45 ml of 20% hydrochloric acid for 7 hours and then worked up by a method analogous to that of Example 58. 0.60 g (81%) of a highly hygroscopic, noncrystalline solid is obtained.

C$_{17}$H$_{25}$N$_5$.2HCl (372.3)

MS: m/z (rel. Int. [%])=300 ([M+H]+, 100), 109(83), 91(88)(FAB method)

$^1$H-NMR data (d$_6$-DMSO, TMS as internal standard): δ=1.3–2.2 (m) 6 H, 2.4–2.9 (m) 4 H, 2.9–3.6 (m) 4 H, 7.0–8.4 (m) 10 H, 4 H replaceable by D$_2$O, 9.00 (d) 1 H, ppm.

EXAMPLE 75

N-Benzoyl-N'-[3-(imidazol-4-yl)propyl]-N''-(3-phenylpropyl)-guanidine

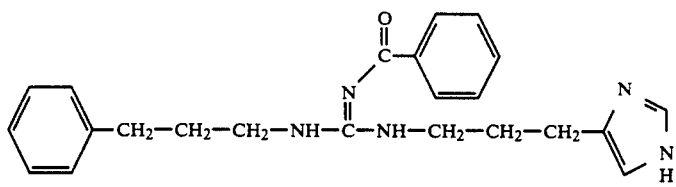

The method of preparation is analogous to that of Example 54, starting from 0.68 9 (5 mmol) of 3-phenylpropylamine.

Yield: 1.1 g (56%), melting point 146° C. (ethyl acetate)

C$_{23}$H$_{27}$N$_5$O (389.5)

MS: m/z (rel. Int. [%])=389 (M+,1), 109(35), 105(100), 91(22), 81(16).

¹H-NMR data (CDCl₃), TMS as internal standard): δ=1.90 (m) 2 H, 2.04 (tt) 2 H, 2.68 (t) 2 H, 2.77 (t) 2 H, 3.1–3.7 (m) 4 H, 6.76 (s) 1 H, 7.1–7.55 (m) 9 H, 8.18 (m) 2 H, ppm.

EXAMPLE 76

N-[3-(Imidazol-4-yl)propyl]-N'-(3-phenylpropyl)-guanidine

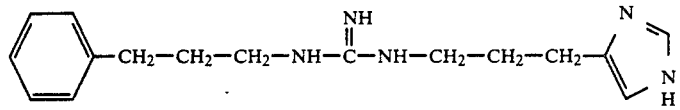

0.73 g (1.9 mmol) of N-benzoyl-N'-[(3-imidazol-4-yl)propyl]-N''-(3-phenylpropyl)-guanidine are heated under reflux in 45 ml of 20% hydrochloric acid for 7 hours. The method of working up is analogous to that of Example 58.

Yield: 0.53 g (78%) of hygroscopic, non-crystalline solid.

C₁₆H₂₃N₅.2HCl (358.3)

MS: m/z (rel. Int.[%])=286 ([M+H]⁺, 100), 109(86), 91(70) (FAB method).

¹H-NMR data (d₆-DMSO, TMS as internal standard): δ=1.78 (m) 2 H, 1.86 (m) 2 H, 2.65 (t) 2 H, 2.74 (t) 2 H, 3.20 (m) 4 H, 7.15–7.4 (m) 5 H, 7.50 (m) 1 H. 7.65 (s) 2 H, replaceable by D₂O, 8.0–8.2 (m) 2 H, replaceable by D₂O, 9.07 (d) 1 H, ppm.

EXAMPLE 77

N-Benzoyl-N'-[3-(imidazol-4-yl)propyl]-N'''-(3,3-diphenylpropyl)-guanidine

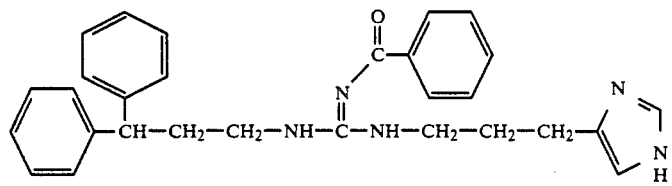

The method of preparation is analogous to that of Example 54, starting from 1.06 g (5 mmol) of 3,3-diphenylpropylamine in acetonitrile as solvent.

Yield: 1.2 g (52%), melting point 148°–149° C. (ethyl acetate).

C₂₉H₃₁N₅O (465.6)

MS: m/z (rel.Int. [%])=465 (M.⁺,1) 167(11), 109(18) 105(100) 95(13)

¹H-NMR data (CDCl₃ TMS as internal standard): δ=1.86 (m) 2 H, 2.44 (dt) 2 H, 2.64 (m) 2 H, 3.3 (broad) 2 H. 3.6 (broad) 2 H, 4.06 t) 1 H, 6.72 (s) 1 H, 7.15–7.55 (m) 14 H, 8.14 (m) 2 H, ppm.

EXAMPLE 78

N-[3-(Imidazol-4-yl)propyl]-N'-(3.3-diphenylpropyl)-guanidine

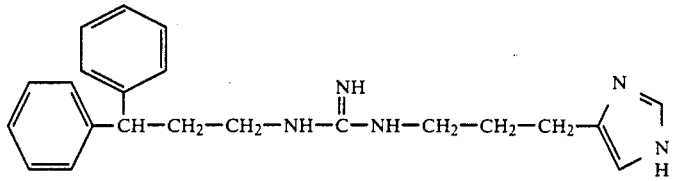

0.84 g (1.8 mmol) of N-benzoyl-N'-[3-(imidazol-4-yl)propyl]-N'''-(3,3-diphenylpropyl)-guanidine are heated under reflux in 45 ml of 20% hydrochloric acid for 7 hours. The method of working up is analogous to that of Example 58.

Yield: 0.67 g (86%) of a hygroscopic, non-crystalline solid.

C₂₂H₂₇N₅.2HCl (434.4)+84), 167(54), 109(100), 91(60) (FAB method)

¹H-NMR data (d₆-DMSO, TMS as internal standard): δ=1.81 (m) 2 H, 2,27 (dt) 2 H, 2.68 (t) 2 H, 3.02 (m) 2 H, 3.16 (m) 2 H, 4.10 (t) 1 H, 7.15–7.6 (m) 13 H, 2 H, replaceable by D₂O. 7.80 (m) 2 H, replaceable by D₂O, 8.99 (d) 1 H, ppm.

EXAMPLE 79

N-Benzoyl-N'-[3-(imidazol-4-yl)propyl]-N'''-[2-[(4-methylphenyl)thio]ethyl]-guanidine

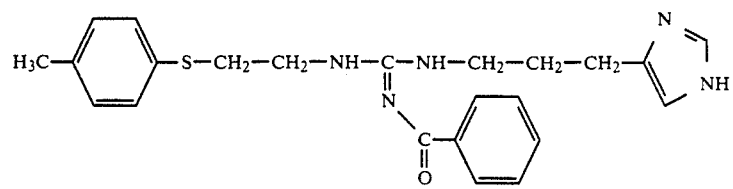

The method of preparation is analogous to that of Example 54, starting from 0.84 g (5 mmol) of 2-[(4-methylphenyl)thio]-ethylamine Yield: 1.5 g (71%), melting point 151° C. (ethyl acetate)

$C_{23}H_{27}N_5OS$ (421.6).Calc.: C 65.53 H 6.46 N 16.61. Found: C 65.63 H 6.58 N 16.64.

$^1$H-NMR data (d$_6$-DMSO, TMS as internal standard): δ = 1.85 (m) 2 H, 2.27 (s) 3 H, 2.57 (t) 2 H, 3.14 (t) 2 H, 3.25 (broad) 2 H, 3.60 (broad) 2 H, 6.81 (s) 1 H, 7.13 (d) 2 H, 7.3–7.55 (m) 5 H, 7.56 (s) 1 H, 8.00 (m) 2 H, ppm.

EXAMPLE 80

N-[3-(Imidazol-4-yl)propyl]-N'-2-[(4-methylphenyl)thio]ethyl]-guanidine

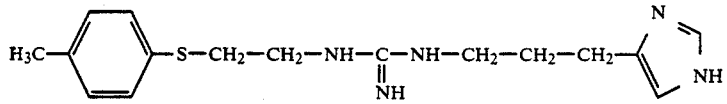

The compound is prepared by a method analogous to that of Example 58 from 0.84 g (2 mmol) of N-benzoyl-N'-[3-(imidazol-4-yl)propyl]-N''-[2-[(4-methylphenyl)-thio]ethyl]-guanidine.

Yield: 0.72 g (92%) of a hygroscopic, non-crystalline solid.

$C_{16}H_{23}N_5S$·2HCl (390.4)

MS (FAB method): m/z (rel. Int. [%]) = 318 ([M+H]+93), 151(63), 123(100), 100(21), 109(67), 91(17).

$^1$H-NMR data (d$_6$-DMSO, TMS as internal standard): δ = 1.86 (m) 2 H, 2.27 (s) 3 H, 2.73 (t) 2 H, 3.11 (t) 2 H, 3.20 (dt) 2 H, 3.38 (dt) 2 H, 7.15 (d) 2 H, 7.31 (d) 2 H, 7.48 (s) 1 H, 7.67 (s) 2 H, replaceable by D$_2$O, 7.95 (t) 1 H, replaceable by D$_2$O, 8.11 (t) 1 H, replaceable by D$_2$O, 9.06 (s) 1 H, 14.8 (broad) 2 H, replaceable by D$_2$O, ppm.

EXAMPLE 81

N-Benzoyl-N'-[2-[(4-chlorophenyl)thio]ethyl]-N''-[3-(imidazol-4-yl)propyl]-guanidine

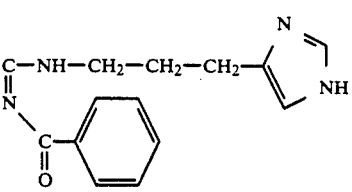

The method of preparation is analogous to that of Example 54, starting from 0.94 g (5 mmol) of 2-[(4-chlorophenyl)thio]ethylamine.

Yield: 1.6 g (72%), melting point 152° C. (ethyl acetate).

$C_{22}H_{24}ClN_5OS$ (442.0). Calc.: C 59.79 H 5.47 N 15.84. Found C 59.68 H 5.48 N 15.88.

$^1$H-NMR data (d$_6$-DMSO, TMS as internal standard): δ = 1.86 (m) 2 H, 2.58 (t) 2 H, 3.21 (t) 2 H, 3.3–3.75 (m) 4 H, 6.81 (s) 1 H. 7.25–7.5 (m) 7 H, 7.56 (s) 1 H, 7.99 (m) 2 H, ppm.

EXAMPLE 82

N-[2-[(4-Chlorophenyl)thio]ethyl]-N'-[3-(imidazol-4-yl)propyl]-guanidine

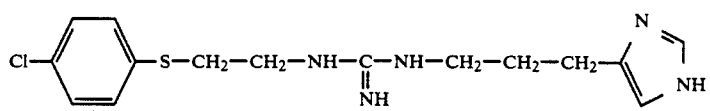

The compound is prepared by a method analogous to that of Example 58 from 0.88 g (2 mmol) of N-benzoyl-N'-[2-[(4-chlorophenyl)thio]ethyl]-N''-[3-(imidazol-4-yl) propyl]-guanidine.

Yield: 0.76 g (93%) of a hygroscopic, non-crystalline solid.

$C_{15}H_{20}ClN_5S$·2HCl (410.8)

MS (FAB method) m/z (rel. Int.[%]) = 338 ([M+H]+,100), 171(29),143(36), 109(71)

$^1$H-NMR data (d$_6$-DMSO, TMS as internal standard): δ = 1.82 (m) 2 H, 2.69 (t) 2 H, 3.14 (t) 2 H, 3.25–3.6 (m) 4 H, 7.40 (m) 4 H, 7.46 (s) 1 H, 7.59 (s) 2 H, replaceable by D$_2$O, 7.83 (t) 1 H, replaceable by D$_2$O, 7.98 (t) 1 H, replaceable by D$_2$O, 9.03 (s) 1 H, 14.8 (broad) 2 H, replaceable by D$_2$O, ppm.

EXAMPLE 83

N-Benzoyl-N'-[3-(imidazol-4-yl)propyl]-N''-[3-[(4-methylphenyl)thio]propyl]-guanidine

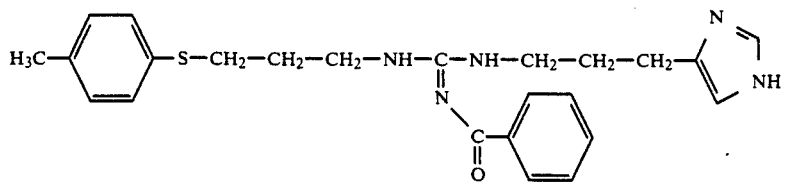

The method of preparation is analogous to that of Example 54, starting from 0.91 g (5 mmol) of 3-[(4-methylphenyl)thio]propylamine.

Yield: 1.4 g (64%), melting point 141° C. (ethyl acetate).

$C_{24}H_{29}N_5OS$ (435.6). Calc.: C 66.18 H 6.71 N 16.08. Found: C 66.37 H 6.80 N 16.11.

$^1$H-NMR data (CDCl$_3$ TMS as internal standard): δ=1.87 (m) 2 H, 1.97 (m) 2 H, 2.29 (s) 3 H, 2.63 (t) 2 H, 2.97 (t) 2 H, 3.45 (broad) 2 H, 3.65 (broad) 2 H, 6.72 (s) 1 H, 7.06 (d) 2 H, 7.23 (d) 2 H, 7.35–7.55 (m) 4 H, 8.18 (m) 2 H, ppm.

EXAMPLE 84

N-[3-(Imidazol-4-yl)propyl]-N'-[3-[(4-methylphenyl)thio]propyl]-guanidine

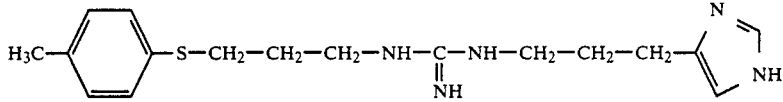

The method of preparation is analogous to that of Example 58, starting from 0.87 g (2 mmol) of N-benzoyl-N'-[3-(imidazol-4-yl)propyl]-N''-[3-[(4-methylphenyl)thio]propyl]-guanidine. The hygroscopic, solid foam initially obtained crystallises when triturated with acetone.

Yield: 0.74 g (91%), melting point 152° C.

$C_{17}H$ 2HCl (404.4). Calc.: C 50.49 H 6.73 N 17.32. Found: C 50.29 H 6.86 N 17.10.

MS (FAB method): m/z (rel. Int. [%])=332 ([M+H]+,100), 165(13), 151(10), 137(37), 123(30), 109(80), 100(30), 91(13).

$^1$H-NMR data (d$_6$-DMSO, TMS as internal standard): δ=1.73 (m) 2 H, 1.84 (m) 2 H. 2.26 (s) 3 H, 2.72 (t) 2 H, 2.99 (t) 2 H, 3.20 (dt) 2 H. 3.28 (dt) 2 H, 7.14 (d) 2 H, 7.26 (d) 2 H, 7.48 (s) 1 H, 7.62 (s) 2 H, replaceable by D$_2$O, 7.98 (t) 1 H, replaceable by D$_2$O, 8.04 (t) 1 H, replaceable by D$_2$O, 9.05 (s) 1 H, 14.6 (broad) 2 H, replaceable by D$_2$O, ppm.

EXAMPLE 85

N-Benzoyl-N'-[3-[(4-chlorophenyl)thio]propyl]-N''-[3-(imidazol-4-yl))propyl]-guanidine

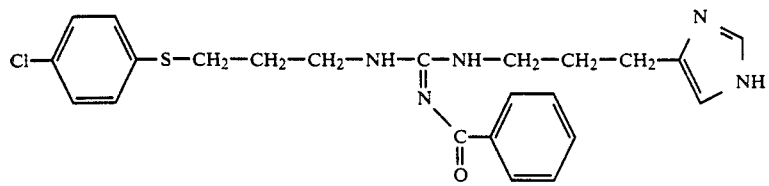

The method of preparation is analogous to that of Example 54, starting from 1.01 g (5 mmol) of 3-[(4-chlorophenyl)thio]-propylamine.

Yield: 1.5 g (66%), melting point 140° C. (ethyl acetate).

$C_{23}H_{26}ClN_5OS$ (456.0).Calc.: C 60.58 H 5.75 N 15.36. Found: C 60.51 H 5.78 N 15.29.

$^1$H-NMR data: 1.88 (m) 2 H, 1.98 (m) 2 H, 2.64 (t) 2 H, 2.98 (t) 2 H, 3.45 (broad) 2 H, 3.65 (broad) 2 H, 6.73 (s) 1 H, 7.20 (s) 4 H, 7.35–7.55 (m) 4 H, 8.18 (m) 2 H, ppm.

EXAMPLE 86

N-[3-[(4-Chlorophenyl)thio]propyl]-N'-[3-(imidazol-4-yl) propyl]-guanidine

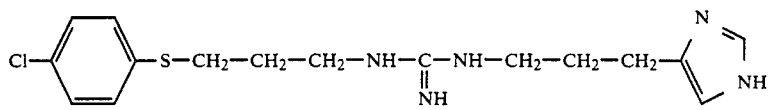

The compound is prepared by a method analogous to that of Example 58 from 0.91 g (2 mmol) of N-benzoyl-N'-[3-(4-chlorophenyl)thio]propyl]-N''-[3-(imidazol-4-yl)propyl]-guanidine. The hygroscopic foam initially obtained crystallises when triturated with acetone.

Yield: 0.75 g (88%), melting point 153° C.

$C_{16}H_{22}ClN_5S.2HCl$ (424.8). Calc.: C 45.24 H 5.69 N 16.49. Found: C 44.98 H 5.79 N 16.19.

MS (FAB method): m/z (rel. Int. [%]) =352 ([M+H]+,54), 185(10), 157(15), 143(12), 109(100), 100(37).

$^1$H-NMR data (d$_6$-DMSO, TMS as internal standard): δ=1.76 (m) 2 H, 1.84 (m) 2 H, 2.72 (t) 2 H, 3.05 (t) 2 H, 3.19 (dt) 2H, 3.28 (dt) 2 H, 7.38 (s) 4 H, 7.48 (s) 1 H, 7.59 (s) 2 H, replaceable by D$_2$O, 7.95 (t) 1 H, replaceable by D$_2$O, 8.00 (t) 1 H, replaceable by D$_2$O, 9.04 (s) 1 H, 14.6 (broad) 2 H, replaceable by D$_2$O, ppm.

EXAMPLE 87

N-Benzoyl-N'-[3-(imidazol-4-yl)propyl]-N'''(2-phenoxyethyl)-guanidine

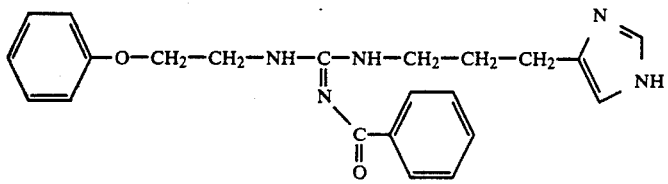

The compound is prepared by a method analogous to that of Example 54 from 0.69 g (5 mmol) of 2-phenoxyethylamine.

Yield: 1.1 g (56%), melting point 144° C. (ethyl acetate).

$C_{22}H_{25}N_5O_2$ (391.5). Calc.: C 67.50 H 6.44 N 17.89. Found: C 67.33 H 6.40 N 17.86.

$^1$H-NMR data (CDCl$_3$, TMS as internal standard): δ=1.92 (m) 2 H, 2.66 (t) 2 H, 3.25–4.1 (m) 4 H, 4.19 (t) 2 H, 6.73 (s) 1 H, 6.8–7.05 (m) 3 H, 7.2–7.5 (m) 6 H, 8.19 (m) 2 H, ppm.

EXAMPLE 88

N-[3-(Imidazol-4-yl)propyl]-N'(2-phenoxyethyl)-guanidine

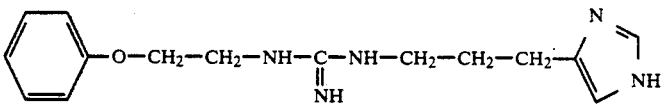

The compound is prepared by a method analogous to that of Example 58 from 0.8 g (2 mmol) of N-benzoyl-N'-[3-(imidazol-4-yl)propyl]-N''-(2-phenoxyethyl)-guanidine.

Yield: 0.66 g (90%) of a hygroscopic, non-crystalline solid.

$C_{15}H_{21}N_5O \cdot 2HCl$ (360.3)

MS (FAB method): m/z (rel. Int. [%])=288 ([M+H]+, 100), 180(5), 151(5), 109(77), 100(16).

$^1$H-NMR data (d$_6$-DMSO, TMS as internal standard): δ=1.86 (m) 2 H, 2,73 (t) 2 H, 3.22 (dt) 2 H, 3.61 (dt) 2 H, 4.07 (t) 2 H, 6.9–7.05 (m) 3 H, 7.47 (m) 2 H, 7.47 (s) 1 H, 7.72 (s) 2 H. replaceable by D$_2$O, 7.95 (t) 1 H, replaceable by D$_2$O, 8.16 (t) 1 H, replaceable by D$_2$O, 9.05 (s) 1 H, 14.6 (broad) 2 H, replaceable by D$_2$O, ppm.

EXAMPLE 89

N-Benzoyl-N'-3-(imidazol-4-yl)propyl]-N''-(1-methyl-2-phenoxyethyl)-guanidine

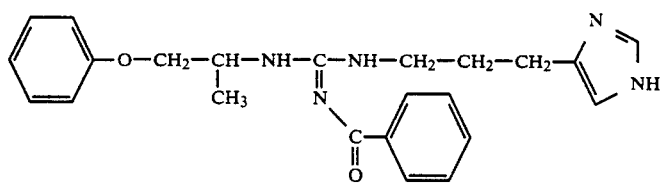

The method of preparation is analogous to that of Example 54, starting from 0.76 g (5 mmol) of 1-methyl-2-phenoxyethylamine.

Yield: 1.2 g (59%), melting point 122° C. (ethyl acetate/ether)

$C_{23}H_{27}N_5O_2$ (405.5). Calc.: C 68.13 H 6.71 N 17.2. Found: C 67.99 H 6.72 N 17.23.

$^1$H-NMR data (CDCl$_3$, TMS as internal standard): δ=1.43 (d) 3 H, 1.91 (m) 2 H, 2.66 (t) 2 H, 3.50 (d) 2 H, 4.03 (d) 2 H, 4.5 (broad) 1 H. 6.72 (s) 1 H, 6.8–7.05 (m) 3 H, 7.02–7.5 (m) 6 H, 8.18 (m) 2 H, ppm.

EXAMPLE 90

N-[3-(Imidazol-4-yl)propyl]-N'-(1-methyl-2-phenoxyethyl)-guanidine

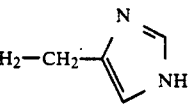

The compound is prepared by a method analogous to that of Example 58 from 0.81 g (2 mmol) of N-benzoyl-N'-[3-(imidazol-4-yl)propyl]-N''-(1-methyl-2-phenoxyethyl)-guanidine.

Yield: 0.68 g (91%) of a hygroscopic, non-crystalline solid.

$C_{16}H_{23}N_5O \cdot 2HCl$ (374.3)

MS (FAB method): m/z (rel. Int.[%])=302 ([M+H]+93), 194(9), 151(9), 135(7), 126(20), 109(100).

$^1$H-NMR data (d$_6$-DMSO, TMS as internal standard): δ=1.23 (d) 3 H, 1.85 (m) 2 H, 2.72 (t) 2 H. 3.22 (dt) 2 H, 3.96 (d) 2 H, 4.17 (m) 1 H, 6.9–7.05 (m) 3 H, 7.29 (m) 2 H, 7.47 (s) 1 H, 7.70 (s) 2 H, replaceable by D$_2$O, 7.88 (d) 1 H, replaceable by D$_2$O, 8.11 (t) 1 H, replaceable by D$_2$O, 9.05 (s) 1 H, 14.6 (broad) 2 H, replaceable by D$_2$O, ppm.

EXAMPLE 91

N-Benzoyl-N'[3-(imidazol-4-yl)propyl]-N''-(1-methyl-2-benzylthioethyl)-guanidine

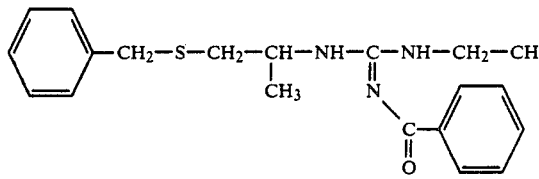

The method of preparation is analogous to that of Example 54, starting from 0.91 g (5 mmol) of 1-methyl-2benzylthioethylamine.

Yield: 1.3 g (60%) of viscous oil $C_{24}H_{29}N_5OS$ (435.6) Calc.: C 66.18 H 6.71 N 16.08. Found: C 66.01 H 6.88 N 15.71.

$^1$H-NMR data (CDCl$_3$, TMS as internal standard): δ = 1.31 (d) 3 H, 1.89 (m) 2 H, 2.65 (m) 4 H, 3.2–3.8 (m) 3 H, 3.73 (s) 2 H, 6.72 (s) 1 H, 7.15–7.55 (m) 9 H, 8.19 (m) 2 H, ppm.

EXAMPLE 92

N-[3-(Imidazol-4-yl)propyl]-N'-(1-methyl-2-benzylthioethyl)-guanidine

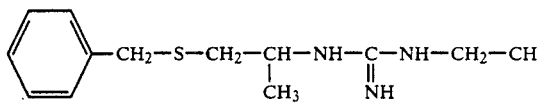

The compound is prepared by a method analogous to that of Example 58 from 0.87 g (2 mmol) of N-benzoyl-N'-[(3-imidazol-4-yl)propyl]-N''-(1-methyl-2-benzylthioethyl)-guanidine.

Yield: 0.69 g (85%) of a hygroscopic, non-crystalline solid.

$C_{17}H_{25}N_5S \cdot 2HCl$ (404.4)

MS (FAB method): m/z (rel. Int. [%]) = 332 ([M+H]$^+$, 22), 109(42), 91(100).

$^1$H-NMR data (d$_6$-DMSO, TMS as internal standard) δ = 1.17 (d) 3 H. 1.87 (m) 2 H, 2.5–2.9 (m) 4 H, 3.22 (dt) 2 H, 3.82 (s) 2 H, 4.04 (m) 1 H. 7.2–7.6 (m) 6 H, 7.68 (s) 2 H, replaceable by D$_2$O, 7.78 (d) 1 H, replaceable by D$_2$O, 8.08 (m) 1H, replaceable by D$_2$O, 9.05 (s) 1 H, 14.6 (broad) 2 H, replaceable by D$_2$O, ppm.

EXAMPLE 93

N-Benzoyl-N'-[3-(imidazol-4-yl)propyl]-N''-[2-[(naphth-2-yl)methylthio]ethyl]-guanidine Preparation of the preliminary stage N-Benzoyl-N'-[2-[(naphth-2-yl)methylthio]ethyl]-O-phenyl-isourea

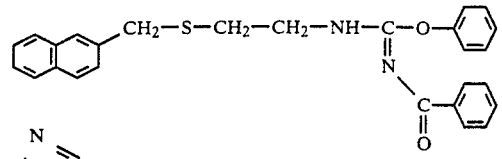

1.63 g (7.5 mmol) of 2-[(naphth-2yl)methylthio]ethylamine and 2.38 g (7.5 mmol) of N-benzoyldiphenylimidocarbonate in 30 ml of methylene chloride are stirred together at room temperature for 20 minutes. The solvent is then distilled off under vacuum and the residue is crystallised from ethanol/ether.

Yield: 3.07 g (93%), melting point 123° C.

$C_{27}H_{24}N_2O_2S$ (440.6) Calc.: 73.61 H 5.49 N 6.36. Found: C 73.78 H 5.58 N 6.40.

$^1$H-NMR data (CDCl$_3$, TMS as internal standard): δ = 2.73 (t) 2 H, 3.67 (dt) 2 H, 3.96 (s) 2 H, 7.09 (m) 2 H, 7.25–8.0 (m) 15 H, 10.35 (t) 1 H, replaceable by D$_2$O, ppm.

N-Benzoyl-N'-[3-(imidazol-4-yl)propyl]-N''-[2-[(naphth-2-yl)methylthio]ethyl]-guanidine

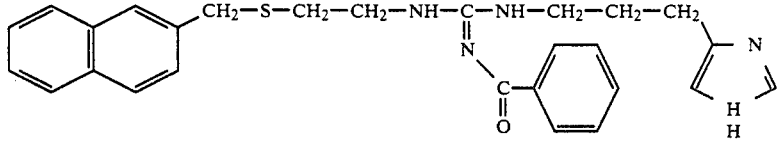

2.2 g (5 mmol) of N-benzoyl-N'-[2-[(naphth-2-yl)methylthio]ethyl]-0-phenylisourea and 0.69 g (5.5 mmol) of 3 (imidazol-4-yl)-propylamine are heated together under reflux in 40 ml of pyridine for one hour. The reaction mixture is worked up by a method analogous to that of Example 54. The solid which precipitates on concentration of the methylene chloride extract by evaporation is recrystallised from methanol.

Yield: 1.6 g (77%). melting point 137° C.

$C_{27}H_{29}N_5OS$ (471.6). Calc.: C 68.76 H 6.20 N 14.85. Found: C 68.61 H 6.22 N 14.75.

$^1$H-NMR data (CDCl$_3$, TMS as internal standard): δ = 1.86 (m) 2 H, 2.62 (t) 2 H, 2.71 (t) 2 H. 3.34 (broad) 2 H, 3.70 (broad) 2 H, 3.91 (s) 2 H, 6.71 (s) 1 H, 7.3–7.55 (m) 7 H, 7.6–7.85 (m) 4 H, 8.21 (m) 2 H, ppm.

EXAMPLE 94

N-[3-(Imidazol-4-yl)propyl]-N'-[2-[(naphth-2-yl)methylthio]ethyl]-guanidine

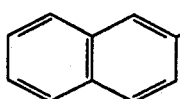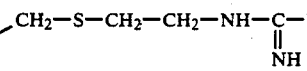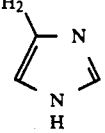

The compound is prepared by a method analogous to that of Example 58 from 0.94 9 (2 mmol) of N-benzoyl-N'-[3-(imidazol-4-yl)propyl]-N''-[2-[(naphth-2-yl)methylthio]ethyl]-guanidine.

Yield: 0.77 g (87%) of a hygroscopic, non-crystalline $C_{20}H_{25}N_5S \cdot 2HCl$ (440.4)

MS (FAB method) m/z (rel. Int [%])=368 ([M+H]+ 26), 141(100), 109(51, 100(15)

$^1$H-NMR data (d$_6$-DMSO, TMS as internal standard): δ=1.85 (m) 2 H, 2.55 (t) 2 H, 2.72 (t) 2 H, 3.20 (dt) 2 H, 3.43 (dt) 2 H, 3.99 (s) 2 H, 7.45–7.55 [m] 4 H, 7.67 (s) 2 H, replaceable by D$_2$O, 7.85–8.00 (m) 5 H, 1 H replaceable by D$_2$O, 8.09 (t) 1 H, replaceable by D$_2$O, 9.05 (s) 1 H, 14.6 (broad) 2 H, replaceable by D$_2$O, ppm.

EXAMPLE 95

N-Benzoyl-N'-[3-(5-methylimidazol-4-yl)propyl]-N''-(3,3-diphenylpropyl)-guanidine

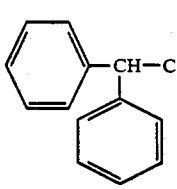

1.06 g (5 mmol) of 3,3-diphenylpropylamine and 1.59 g (5 mmol) of N-benzoyl-diphenylimidocarbonate are stirred together at room temperature in 20 ml of methylene chloride for 15 minutes. The solvent is then distilled off under vacuum and the residue is taken up with 30 ml of pyridine and then heated for one hour under reflux with the addition of 0.77 g (5.5 mmol) of 3-(5-methylimidazol-4-yl)-propylamine. The reaction product is isolated and purified by a method analogous to that of Example 54.

Yield: 1.1 g (46%) of dry foam.
$C_{30}H_{33}N_5O$ (479.6)

MS: m/z (rel. Int. [%])=479 (M+, 12), 312(8), 167(12), 109(27), 105(100), 95(17), 77(45).

$^1$H-NMR data (CDCl$_3$, TMS as internal standard): δ=1.83 (m) 2 H, 2.12 (s) 3 H, 2.2–2.8 (m) 4 H, 3.0–3.6 (m) 4 H, 4.08 (t) 1 H, 6.9–7.6 (m) 14 H, 8.13 (m) 2 H, ppm.

EXAMPLE 96

N-[3-(5-Methylimidazol-4-yl)propyl]-N'-(3,3-diphenylpropyl)-guanidine

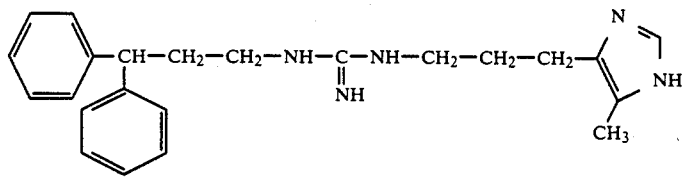

The compound is prepared by a method analogous to that of Example 58 from 0.77 g (1.5 mmol) of N-benzoyl-N'-[3-(5-methylimidazol-4-yl)propyl]-N''-(3,3-diphenylpropyl)-guanidine.

Yield: 0.57 g (85%) of a hygroscopic, non-crystalline solid.

$C_{23}H_{29}N_5 \cdot 2HCl$ (448.4)

MS (FAB method): m/z (rel. Int. [%]) =376 ([M+H]+100), 254(14), 208(4), 167(26), 123(76), 100(30), 91(28).

$^1$H-NMR data (d$_6$-DMSO, TMS as internal standard): δ=1.80 (m) 2 H, 2.22 (s) 3 H, 2.05–2.9 (m) 4 H, 2.9–3.5 (m) 4. H, 4.16 ( t) 1 H, 7.1–7.4 (m) 10 H, 7.51 (s) 2 H, replaceable by D$_2$O, 7.98 (m) 2 H, replaceable by D$_2$O, 8.90 (s) 1 H, 14.6 (broad) 2 H, replaceable by D$_2$O, ppm.

EXAMPLE 97

N-[3-(Imidazol-4-yl)propyl]-N'(4,4-diphenylbutyl)-guanidine

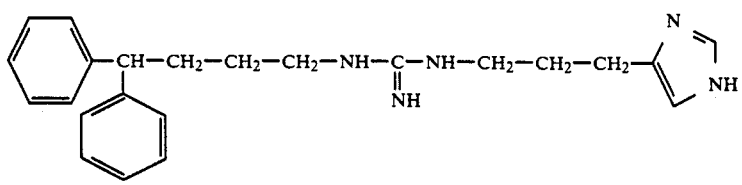

The method of preparation is analogous to that of Example 58, starting from 0.96 g (2 mmol) of N-benzoyl-N'-[3-(imidazol-4-yl)propyl]-N''-(4,4-diphenylbutyl)-guanidine.

Yield. 0.76 g (85%) of a hygroscopic, non-crystalline solid.

$C_{23}H_{29}N_5.2HCl$ (448.4)

$^1$H-NMR data (d$_6$-DMSO, TMS as internal standard): δ=1.3–2.1 (m) 4 H, 2.2 (m) 2 H, 2.73 (t) 2 H, 2.9–3.5 (m) 4 H. 4.08 (t) 1 H, 7.15–7.6 (m) 13 H, 2 H replaceable by D$_2$O, 7.7–8.1 (m) 2 H, replaceable by D$_2$O, 9.5 (s) 1 H, 14.6 (broad) 2 H, replaceable by D$_2$O, ppm.

EXAMPLE 98

N-[3-(Imidazol-4-yl)propyl]-N'[2-[(3-trifluoromethylphenyl) methylthio]ethyl]-guanidine

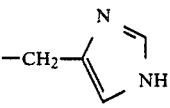

The method of preparation is analogous to that of Example 58, starting from 0.69 g (1.4 mmol) of N-benzoyl-N'-[3-(imidazol-4-yl)propyl]-N''-[2-[(3-trifluoromethylphenyl)methylthio]ethyl]-guanidine.

Yield: 0.59 g (92%) of a hygroscopic, non-crystalline solid.

$C_{17}H_{22}F_3N_5S.2HCl$ (458.4)

$^1$H-NMR data (d$_6$-DMSO, TMS as internal standard): δ=1.85 (m) 2 H, 2.59 (t) 2 H, 2.73 (t) 2 H, 3.1–3.6 (m) 4 H. 3.92 (s) 2 H, 7.4–8.1 (m) 9 H, 4 H replaceable by D$_2$O, 9.05 (s) 1 H, 14.6 (broad) 2 H, replaceable by D$_2$O, ppm.

EXAMPLE 99

N-[3-(Imidazol-4-yl)propyl]-N'-[2-[(4-methoxyphenyl)-methylthio]ethyl]-guanidine

The method of preparation is analogous to that of Example 58, starting from 0.54 g (1.2 mmol) of N-benzoyl-N'-[3-(imidazol-4-yl)propyl]-N''-[2-[(4-methoxyphenyl)methylthio]ethyl]-guanidine.

Yield: 0.11 g (22%) of a hygroscopic, non-crystalline solid $C_{17}H_{25}N_5OS.2HCl$ (420.4)

$^1$H-NMR data (d$_6$-DMSO, TMS as internal standard): δ=1.83 (m) 2 H, 2.59 (t) 2 H, 2.73 (t) 2 H, 3.1–3.6 (m) 4 H, 3.7 (s) 5 H, 6.88 (d) 2 H, 7.29 (d) 2 H, 7.43 (s) 1 H, 7.6 (s) 2 H, replaceable by D$_2$O, 7.7–8.0 (m) 2 H, replaceable by D$_2$O, 9.05 (s) 1 H. 14.6 (broad) 2 H, replaceable by D20. ppm.

EXAMPLE 100

N$^1$-Benzoyl-N$^2$-3-(4-imidazolyl)propyl]-N$^3$-[2-(N-benzyl-N-phenylamino)-ethyl]-guanidine

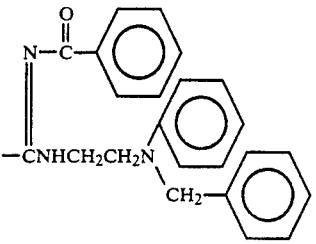

A mixture of 3.48 g (10 mmol) of N$^1$-benzoyl-N$^2$-(3-(4-imidazolyl)propyl]-O-phenyl-isourea and 2.26 g (10 mmol) of N-benzyl-N-phenyl-ethylenediamine in 50 ml of ethanol is boiled under reflux for 17 hours. The residue obtained after rotation is chromatographed on silica gel, using ethyl acetate/ethanol (80:20). After the main fraction has been concentrated by evaporation, it yields 3.14 g (65%) of N$^1$-benzoyl-N$^2$-[3-(4-imidazolyl)-propyl]-N$^3$-[2-(N-benzyl-N-phenylamino)ethyl]-guanidine as a colourless solid. Colourless crystals melting at 148.1°–149.5° C. are obtained after recrystallisation from ethyl acetate.

$C_{29}H_{32}N_6O$ (480.62)

$^1$H-NMR data (CD$_3$OD, TMS as internal standard): δ=1.88 (m) 2 H, 2.63 (t) 2 H, 3.20 (t) 2 H, 3.58–3.72 (m) 4 H, 4.59 (s) 2 H, 4.8 (broad) 3 H, replaceable by D$_2$O, 6.50–7.58 (m) 15 H, 8.04–8.21 (m) 2 H, ppm.

EXAMPLE 101

N$^1$-[3-(4-Imidazolyl)propyl]-N$^2$-[2-(N-benzyl-N-phenylamino)-ethyl]-guanidine trihydrochloride

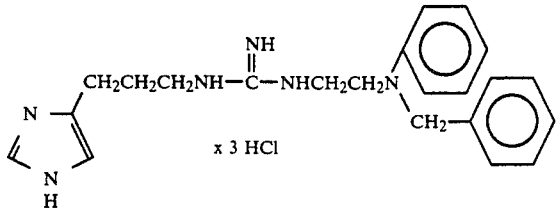

1.60 g (3.3 mmol) of N$^1$-benzoyl-N$^2$[3-(4-imidazolyl) propyl]-N$^3$ [2-(N-benzyl-N-phenylamino)ethyl]-guanidine (Example 100) are boiled in 30 ml conc.hydrochloric acid for 1.4 hours. After cooling, the reaction mixture is concentrated by evaporation to one third of its original quantity and the aqueous solution obtained is extracted three times with 30 ml of ether. The aqueous phase is then filtered and concentrated by evaporation under vacuum. The residue is taken up twice with 20 ml portions of ethanol and again concentrated by evaporation. The residue finally obtained is recrystallised from absolute ethanol. 0.92 g (57%) of the title compound is obtained in the form of a colourless, hygroscopic solid.

$C_{22}H_{31}Cl$ (485.89)

$^1$H-NMR data (CD$_3$OD, TMS as internal standard): δ=1.79–2.20 (m) 2 H, 2.88 (t) 2 H, 3.32 (t) 2 H, 3.60 (m) 2H, 4.13 (t) 2 H, 4.83 (s) 2 H, 4.9 (broad) 7 H, replaceable by D$_2$O, 7.28–7.90 (m) 11 H, 9.02 (s) 1 H, ppm.

EXAMPLE 102

$N^1$-[3-(4-Imidazolyl)propyl]-$N^2$-[2-(N-benzyl-N-(4-fluorophenyl)amino)ethyl]-guanidine trihydrochloride

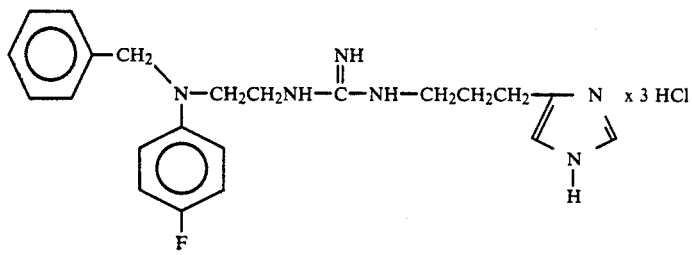

The method of preparation is analogous to that of Example 101.

$C_{22}H_{30}Cl_3FN_6$ (503.88)

$^1$H-NMR data (CD$_3$OD, TMS as internal standard): δ=1.80–2.21 (m) 2 H, 2.88 (t) 2 H, 3.30 (t) 2 H, 3.59 (m) 2 H, 4.12 (t) 2 H, 4.83 (s) 2 H, 4.9 (broad) 7 H, 7.14–7.86 (m) 10 H, 9.01 (s) 1 H, ppm.

EXAMPLE 103

$N^1$-[3-(4-Imidazolyl)propyl]-$N^2$-[2-(N-benzyl-N-(4-chlorophenyl)amino)ethyl]-guanidine trihydrochloride

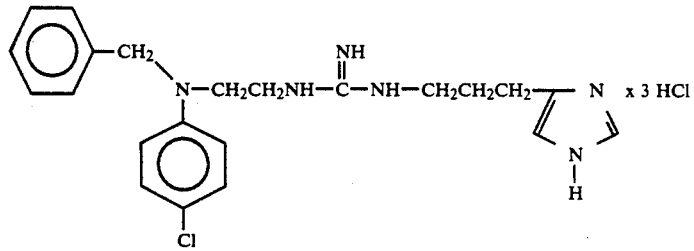

The method of preparation is analogous to that of Example 101.

$C_{22}H_{30}Cl_4N_6$ (520.33)

$^1$H-NMR data (CD$_3$OD, TMS as internal standard): δ=1.79–2.18 (m) 2 H, 2.87 (t) 2 H, 3.31 (t) 2 H, 3.58 (m) 2 H, 4.11 (t) 2 H, 4.81 (s) 2 H, 4.9 (broad) 7 H, 7.24–7.89 (m) 10 H, 8.99 (s) 1 H, ppm.

EXAMPLE 104

$N^1$-[3-(4-Imidazolyl)propyl]-$N^2$-[2-(N-benzyl-N-(4-bromophenyl)amino)ethyl]-guanidine trihydrochloride

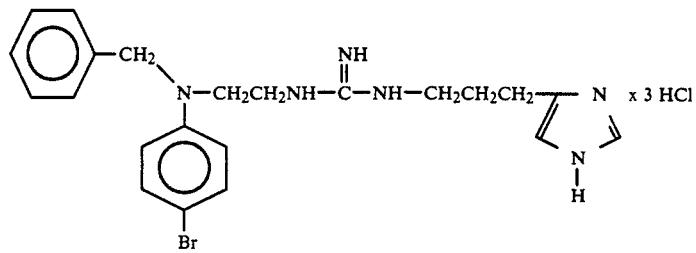

The method of preparation is analogous to that of Example 101.

$C_{22}H_{30}BrCl_3N_6$ (564.78)

$^1$H-NMR data (CD$_3$OD, TMS as internal standard): δ=1.81–2.20 (m) 2 H, 2.87 (t) 2 H, 3.28 (t) 2 H, 3.56 (m) 2 H, 4.12 (t) 2 H,

EXAMPLE 105

N-[3-(Imidazol-4-yl)propyl]-N'-[2-(2-thenylthio)ethyl]-guanidine

Preparation of the preliminary stages a) N-Benzoyl-N'-[2 (2 thenylthio)ethyl]-thiourea

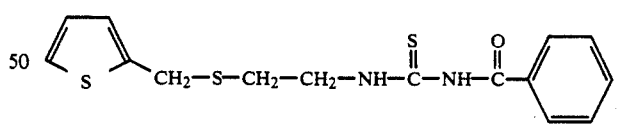

1.73 g (10 mmol) of 2-(2-thenylthio)ethylamine and 1.63 g (10 mmol) of benzoyl isothiocyanate are heated under reflux in 120 ml of chloroform for 30 minutes.

The solvent is then distilled off under vacuum and the oily residue is crystallised with ether.

Yield: 3.06 g (91%), melting point 85° C. (ether).

C$_{15}$H$_{16}$N$_2$OS$_3$ (336.5) Calc.: C 53.54 H 4.79 N 8.32. Found: C 53.54 H 4.79 N 8.17.

MS m/z (rel Int. [%]) = 336 (M.+,1), 239(94), 105(95), $^1$H-NMR data (CDCl$_3$ TMS as internal standard): δ=2.84 (t) 2 H, 3.91 (dt) 2H, 4.03 (s) 2 H, 6.9–7 05 (m) 2 H, 7.24 (dd) 1 H, 7.53 (m) 2 H, 7.62 (m) 1 H, 7.86 (m) 2 H, 9.06 (broad) 1 H, replaceable by D$_2$O, 10.98 (broad) 1 H. replaceable by D$_2$O, ppm.

b) S-Methyl-N-[2-(2-thenylthio)ethyl]-isothiouronium iodide

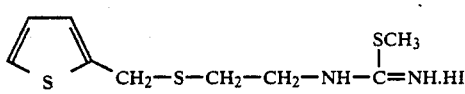

2.52 g (7.5 mmol) of N-benzoyl-N'-[2-(2-thenylthio)ethyl]-thiourea and 2.1 g of potassium carbonate are heated together under reflux in a mixture of 30 ml of water and 100 ml of methanol for 40 minutes. The reaction mixture is then concentrated by evaporation under vacuum and the residue is taken up with ether and washed three times with water. The organic phase is dehydrated over sodium sulphate and concentrated by evaporation under vacuum, and the oily residue is taken up with 100 ml of ethanol and then stirred overnight at room temperature after the addition of 0.6 ml of methyl iodide. The solvent is distilled off under vacuum and the residue is stirred up with acetone and ether. 1.97 g (70%) of the isothiouronium salt are obtained as a colourless solid melting at 80° to 81° C.

C$_9$H$_{14}$N$_2$S$_3$.HI (374.3) Calc.: C 28.88 H 4.04 N 7.48. Found: C 28.80 H 4.06 N 7.43.

Molar mass (MS): Calc. 246.03192, Found: 246.03186

MS: m/z (rel. Int. [%])=246 (M.+,6). 149(100), 97(96)

$^1$H-NMR data (d$_6$-DMSO, TMS as internal standard): δ=2.61 (s) 3 H, 2.67 (t) 2 H, 3.52 (t) 2 H, 4.06 (s) 2 H, 6.97 (m) 1 H, 7.02 (m) 1 H, 7.46 (dd) 1 H, 9.2 (broad) 3 H, replaceable by D$_2$O, ppm.

N-[3-(Imidazol-4-yl)propyl]-N'-[2-(2-thenylthio)ethyl]-guanidine

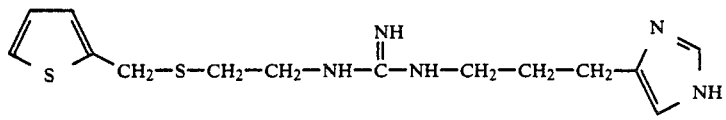

1.87 g (5 mmol) of S-methyl-N[2-(2-thenylthio)ethyl]isothiouronium iodide and 0.69 g (5.5 mmol) of 3-(imidazol-4-yl)-propylamine are together heated under reflux in 40 ml of anhydrous pyridine for 3 hours. After concentration by evaporation under vacuum, the reaction product is isolated and purified by preparative layer chromotography (silica gel 60 PF$_{254}$, containing gypsum; solvent: chloroform/methanol 85+15, ammoniacal atmosphere). 1.53 g (68%) of N-[3-(imidazol-4-yl)propyl]-N'-[2-(2-thenylthio)ethyl]-guanidine hydriodide are obtained as a viscous oil.

C$_{14}$H$_{21}$N$_5$S$_2$.HI (451.4)

Molar mass (MS) Calc.:323.12384, found: 323.12405

MS: m/z (rel. Int-[%]) =323 (M+, 4) 198(11), 128([HI]+,23), 97(100).

$^1$H-NMR data (d$_6$-DMSO, TMS as internal standard): δ=1.80 (m) 2 H, 2.35–2.9 (m) 4 H, 2.9–3.6 (m) 4 H, 4.06 (s) 2 H, 6.8–7.15 (m) 3 H, 7.2–7.8 (m) 5 H , 4 H replaceable by D$_2$O, 8.07 (d) 1 H, ppm.

The dipicrate melts at 123° C. after recrystallisation from ethanol.

C$_{14}$H$_{21}$N$_5$S$_2$.2C$_6$H$_3$N$_3$O$_7$,½C$_2$H$_5$OH (804.7).

Calc.: C 40.30 H 3.76 N 19.15. Found: C 40.21 H 3.73 N 19.25.

EXAMPLE 106

N-Benzoyl-N'-[3-(imidazol-4-yl)propyl]-N"-[2-(2-thenylthio)ethyl]-guanidine

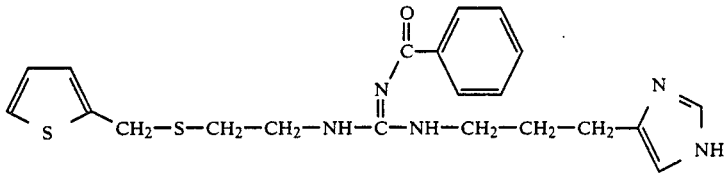

0.87 g (5 mmol) of 2-(2-thenylthio)-ethylamine and 1.59 g (5 mmol) of N-benzoyl-diphenylimidocarbonate are stirred together in 20 ml of methylene chloride for 15 minutes at room temperature. The solvent is distilled off under vacuum and the residue is taken up with 30 ml of pyridine and then heated under reflux for 60 minutes after the addition of 0.69 g (5.5 mmol) of 3-(imidazol-4-yl)-propylamine. The reaction mixture is concentrated by evaporation under vacuum and the residue is dissolved in dilute acid and extracted with ether to remove the phenol formed in the reaction. Alkalization of the aqueous phase with ammonia is followed by extraction with methylene chloride, and the organic phase is washed with water, dehydrated over sodium sulphate and concentrated by evaporation under vacuum. The crude product is purified by preparative layer chromatography (silica gel 60 PF$_{254}$, containing gypsum; solvent: chloroform/methanol 99+1, ammoniacal atmosphere). 1.55 g (72%) of colourless crystals melting at 128°–129° C. are obtained after crystallisation from ethyl acetate.

C$_{21}$H$_{25}$N$_5$OS$_2$ (427.6). Calc.: C 58:99 H 5.89 N 16.38. Found: C 58.91 H 5.93 N 16.29.

$^1$H-HMR data (d$_6$-DMSO, TMS as internal standard): δ=1.95 (m) 2 H, 2.68 (m) 2 H, 2.80 (t) 2 H, 3.0–3.7 (m) 4 H, 4.02 (s) 2 H, 6.7–7.05 (m) 3 H, 7.25–7.7 (m) 5 H, 8.13 (m) 2 H, ppm.

EXAMPLE 107

N-Benzoyl-N'-[3-(imidazol-4-yl)propyl]-N''-[2-[(pyrid-2-yl)methylthio]ethyl]-guanidine

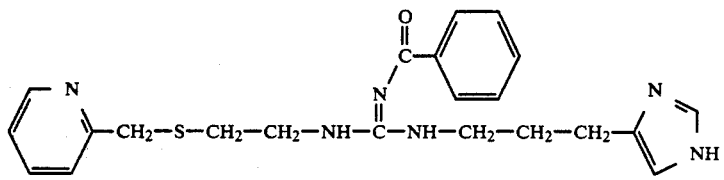

The compound is prepared and isolated by a method analogous to that of Example 106, starting from 0.84 g (5 mmol) of 2-[(pyrid-2-yl)methylthio]-ethylamine.

Yield: 1.2 g (57%), melting point 122°–123° C. (ethyl acetate)

$C_{22}H_{26}N_6OS$ (422.6). Calc.: C 62.54 H 6.20 N 19.89. Found: C 62.45 H 6.13 N 19.92.

$^1$H-NMR data (CDCl$_3$, TMS as internal standard): δ=1.92 (m) 2 H, 2.67 (t) 2 H, 2.77 (t) 2 H, 3.15–3.85 (m) 4 H, 3.86 (s) 2 H, 6.75 (s) 1 H, 6.9–7.8 (m) 7 H, 8.17 (m) 2 H, 8.43 (m) 1 H, ppm.

EXAMPLE 108

N-Benzoyl-N'-[3-(imidazol-4-yl)propyl]-N''-[2-[(pyrid-methylthio]ethyl]-guanidine

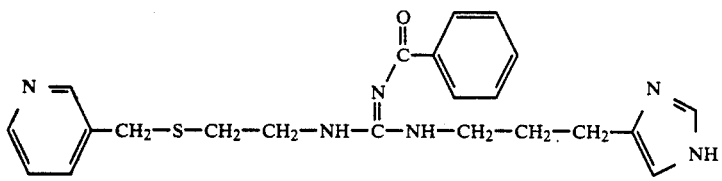

The compound is prepared and isolated by a method analogous to that of Example 106, starting from 0.84 g (5 mmol) of 2-[(pyrid-3-yl)methylthio]-ethylamine.

Yield: 1.36 (64%), melting point 130°–131° C. (ethyl acetate)

$C_{22}H_{26}N_6OS$ (422.6). Calc.: C 62.54 H 6.20 N 19.89. Found: C 62.31 H 6.24 N 19.63.

MS: m/z (rel. Int. [%])=422 (M+, <1), 330(12), 105(100), 95(29), 92(49), 77(80).

$^1$H-NMR data (CDCl$_3$, TMS as internal standard): δ=1.92 (m) 2 H, 2.67 (t) 2 H, 2.73 (t) 2 H, 3.4 (broad) 2 H, 3.7 (broad) 2 H, 3.73 (s) 2 H, 6.76 (s) 1 H, 7.16 (m) 1 H, 7.3–7.5 (m) 4 H, 7.65 (m) 1 H, 8.19 (m) 2 H, 7.45 (m) 1 H, 8.49 (m) 1 H, ppm.

EXAMPLE 109

N-[3-(Imidazol-4-yl)propyl]-N'-[2[(pyrid-3-yl)methylthio]ethyl]-guanidine

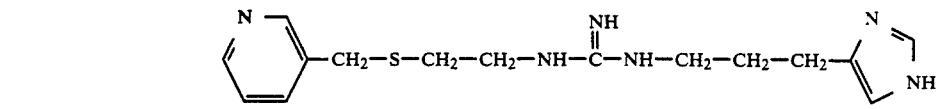

0.85 g (2 mmol) of N-benzoyl-N'-[3-(imidazol-4-yl)propyl]-N''-[2-[(pyrid-3-yl)methylthio]ethyl]-guanidine (Example 108) are heated under reflux in 45 ml of 18% hydrochloric acid for 6 hours. When the reaction mixture has cooled down, the benzoic acid formed is removed by extraction with ether, the aqueous phase is evaporated to dryness under vacuum and the residue is dehydrated in a high vacuum. 0.78 g (91%) of a dry, highly hygroscopic foam is obtained.

$C_{15}H_{22}N_6S·3HCl$ (427.8)

Molar mass (MS) Calc.: 318.16267, found: 318,16299.

MS: m/z (rel. Int-[%])=318 (M+, 3), 168(17) 125(29) 95(51), 93(100), 92(57), 44(89).

$^1$H-NMR data (d$_6$-DMSO, TMS as internal standard): δ=1.87 (m) 2 H, 2.62 (t) 2 H, 2.73 (t) 2 H, 3.0–3.7 (m) 4 H, 4.10 (s) 2 H, 7.3–8.3 (m) 6 H, 4 H replaceable by D$_2$O, 8.5–9.1 (m) 4 H, ppm.

EXAMPLE 110

N-Benzoyl-N'-[3-(imidazol-4-yl)propyl]-N''-[2-[(pyrid-4-yl)methylthio]ethyl]-guanidine

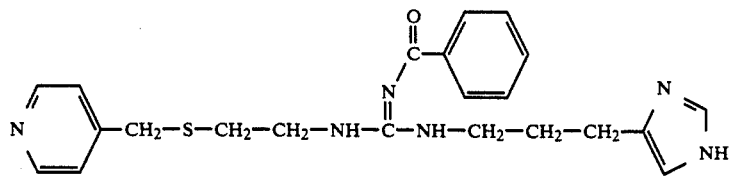

The method of preparation is analogous to that of Example 106, starting from 0.84 g (5 mmol) of 2-[(pyrid-4-yl)methylthio]-ethylamine.

Yield: 1.4 g (66%), melting point 135°–136° C. (ethyl acetate)

$C_{22}H_{26}N_6OS$ (422.6). Calc.: C 62.54 H 6.20 N 19.89. Found: C 62.25 H 6.20 N 19.82.

MS: m/z (rel. Int.[%])=422 (M+, 1), 105(100) 95(55), 92(76) 81(45) 77(69).

$^1$H-NMR data (CDCl$_3$, TMS as internal standard): δ=1.93 (m) 2 H, 2.68 (t) 2 H, 2.74 (t) 2 H, 3.4 (broad) 2 H, 3.7 (broad) 2 H, 3.71 (s) 2 H, 6.78 (s) 1 H, 7.23 (d) 2 H, 7.3–7.5 (m) 4 H, 8.21 (m) 2 H, 8.47 (d) 2 H, ppm.

EXAMPLE 111

N-3-(Imidazol-4-yl)propyl]-N'-[2-[(pyrid-4-yl)methylthio]ethyl]-guanidine

 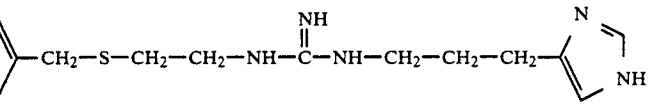

0.85 g (2 mmol) of N-benzoyl-N'-[3-(imidazol-4-yl)propy]-N''-[2-[(pyrid-4-yl)methylthio]ethyl]-guanidine are heated under reflux in 45 ml of 18% hydrochloric acid for 6 hours and then worked up by a method analogous to that of Example 109.

Yield: 0.81 g (95%) of a dry, hygroscopic foam C$_{15}$H$_{22}$N$_6$S.3HCl (427.8)

Molar mass: (.MS) Calc.: 318.16267, found: 318.16287.

MS: m/z (rel.Int.[%])=318 (M+,2), 125(1295(35), 93(100), 92(27).

$^1$H-NMR data (d$_6$-DMSO, TMS as internal standard): δ=1.85 (m) 2 H. 2.3–2.9 (m) 4 H, 2.9–3.7 (m) 4 H, 4.10 (s) 2 H, 7.45 (m) 1 H, 7.70 (broad) 2 H, replaceable by D$_2$O. 7.75–8.4 (m) 2 H, replaceable by D$_2$O, 8.07 (d) 2 H, 8.84 (d) 2 H, 9.03 (d) 1 H, ppm.

EXAMPLE 112

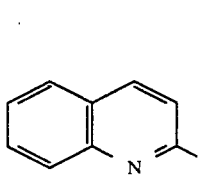 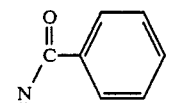 

N-Benzoyl-N'-[2-[(quinolin-2-yl)methylthio]ethyl]-N''-3-(imidazol-4-yl)propyl]-guanidine Preparation of the preliminary stage 2-[(Quinolin-2-yl)methylthio]-ethylamine

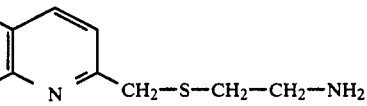

4.28 g (20 mmol) of 2-Chloromethylquinoline.HCl and 2.27 g (20 mmol) of cysteamine.HCl are heated under reflux in 50 ml of 48% aqueous hydrobromic acid for 5 hours. The reaction mixture is then evaporated to dryness under vacuum and the residue is recrystallised from ethanol/water.

Yield 5.5 g (72%), melting point 207°–209° C.

C$_{12}$H$_{14}$N$_2$S.2HBr (380.2). Calc.: C 37.92 H 4.24 N 7.37. Found: C 37.65 H 4:26 N 7.31.

MS: m/z (rel. Int.[%])=218 (M+,3), 143(95, 142(90), 80(100), 77(38).

$^1$NMR data (d$_6$-DMSO, TMS as internal standard): δ=2.6–3.3 (m) 4 H, 4.40 (s) 2 H, 7.65–8.4 (m) 5 H, 9.01 (d) 1 H, ppm.

N-Benzoyl-N'-[2-[(quinolin-2-yl)methylthio]ethyl]-N''-[3-(imidazol-4-yl)propyl]-guanidine The method of preparation is analogous to that of Example 106, starting from 1.09 g (5 mmol) of 2-[(quinolin-2-yl)methylthio]-ethylamine prepared from the dihydrobromide by reaction with 10 mmol of sodium methylate in ethanol.

Yield: 1.77 g (75%), melting point 120°–122° C. (ethyl acetate)

C$_{26}$H$_{28}$N$_6$OS (472.6). Calc.: C 66.08 H 5.97 N 17.78. Found: C 65.89 H 6.04 N 17.78.

$^1$H-NMR data (d$_6$-DMSO, TMS as internal standard): δ=1.88 (m) 2 H, 2.73 (t) 2 H, 2.86 (t) 2 H. 3.43 (dt) 2 H, 3.67 (dt) 2 H, 4.08 (s) 2 H, 6.80 (s) 1 H, 7.3–8.4 (m) 12 H, ppm.

EXAMPLE 113

N-[2-[(Quinolin-2-yl)methylthio]ethyl]-N'-[3-(imidazol-4-yl)propyl]-guanidine

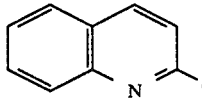 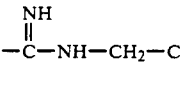

0.95 g (2 mmol) of N-benzoyl-N'-[2-[(quinolin-2-yl) methylthio]ethyl]-N''-[3-(imidazol-4-yl)propyl]-guanidine are heated under reflux in 45 ml of 18% hydrochloric acid for 6 hours and the product is worked up by a method analogous to that of Example 109. 0.86 g (90%) of a hygroscopic, non-crystalline solid is obtained.

C$_{19}$H$_{24}$N$_6$S.3HCl (477.9)

MS (FAB method): m/z (rel. Int.[%])=369 (M+H]+ 100), 226(10), 174(48), 143(55), 142(21), 109(64), 95(17).

$^1$H-NMR data (d$_6$-DMSO, TMS as internal standard): δ1.85 (m) 2 H, 2.73 (t) 4 H, 3.0–3.7 (m) 4 H, 4.43 (s) 2 H, 7.4–8.6 (m), 10 H, 4 H replaceable by D$_2$O, 8.93 (d) 1 H, 9.01 (d) 1 H, ppm.

EXAMPLE 114

N-[2-[(Benzimidazol-2-yl)methylthio]ethyl]-N'-benzoyl-N''-[3-(imidazol-4-yl)propyl]-guanidine

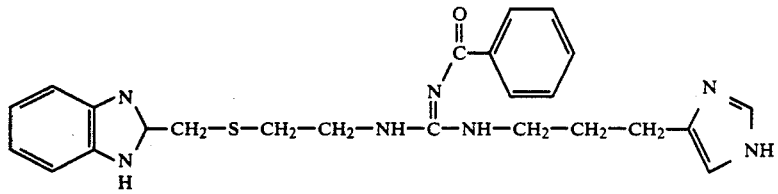

The method of preparation is analogous to that of Example 106, starting from 1.04 g (5 mmol) of 2-[(benzimidazol-2-yl)methylthio]-ethylamine.

Yield: 1.15 g (50%) of a non-crystalline solid (foam) $C_{24}H_{27}N_7OS$ (461.6)

MS: m/z (rel. Int. [%])=461 (M+,1), 131(90), 109(22), 105(100).

$^1$H-NMR data (d$_6$-DMSO, TMS as internal standard): $\delta = 1.85$ (m) 2 H, 2.5–3.0 (m) 4 H, 3.0–3.7 (m) 4 H, 3.99 (s) 2 H, 6.77 (s) 1 H, 7.0–7.7 (m) 8 H, 8.07 (m) 2 H, ppm.

EXAMPLE 115

N-[2-[(Benzimidazol-2-yl)methylthio]-ethyl]-N'-[3-(imidazol-4-yl)propyl]-guanidine

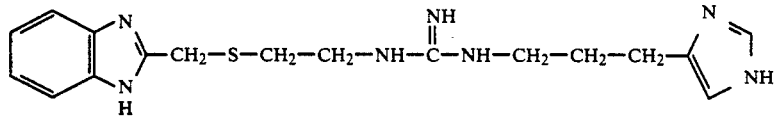

0.65 g (1.4 mmol) of N-[2-[(benzimidazol-2-yl) methylthio]ethyl]-N'-benzoyl-N''-[3-(imidazol-4-yl)propyl]-guanidine are heated under reflux in 45 ml of 18% hydrochloric acid for 6 hours and worked up by a method analogous to that of Example 109.

Yield: 0.57 g (87%) of non-crystalline, hygroscopic solid (foam)

$C_{17}H_{23}N_7S.3HCl$ (466.9)

MS (FAB method): m/z (rel. Int.[%])=358 ([M+H]+,100), 228(53), 226(10), 131(86), 109(43)

$^1$H-NMR data (d$_6$-DMSO, TMS as internal standard): $\delta 1.85$ (m) 2 H, 2.75 (t) 2 H, 2.83 (t) 2 H, 2.9–3.7 (m) 4 H, 4.39 (s) 2 H, 7.3–8.3 (m) 9 H, 4 H replaceable by D$_2$O, 9.02 (d) 1 H, ppm.

EXAMPLE 116

N-Benzoyl-N'-[3-(imidazol-4-yl)propyl]-N''-[2-[(pyrid-2-yl) thio]ethyl]-guanidine

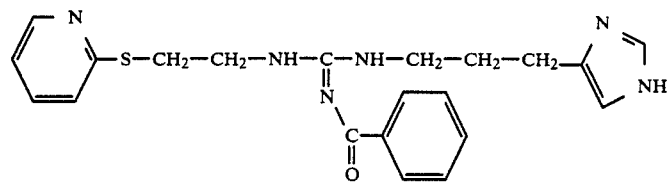

The method of preparation is analogous to that of Example 106, starting from 0.77 g (5 mmol) of 2-[(pyrid-2-yl)thio]-ethylamine.

Yield: 1.5 g (73%). melting point 145° C. (ethyl acetate)

$C_{21}H_{24}N_6OS$ (408.5). Calc.: C 61.74 H 5.92 N 20.57. Found: C 61.74 H 6.00 N 20.57.

$^1$H-NMR data (CDCl$_3$, TMS as internal standard): $\delta 1.96$ (m) 2 H, 2.68 (t) 2 H, 3.27 (m) 2 H, 3.54 (m) 2 H, 3.94 (m) 2 H, 6.72 (s) 1 H, 7.09 (m) 1 H, 7.26 (m) 1 H. 7.35–7.6 (m) 5 H, 8.14 (m) 2 H, 8.38 (d) 1 H, ppm.

EXAMPLE 117

N-[(3-Imidazol-4-yl)propyl]-N'-[2-[(pyrid-2-yl)thio]ethyl]-guanidine

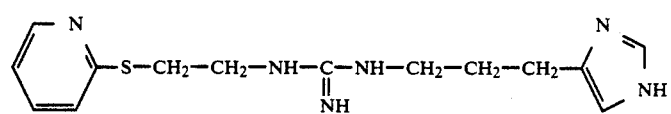

0.82 g (2 mmol) of N-benzoyl-N'-[3-(imidazol-4-yl propyl]-N''-[2-[(pyrid-2-yl)thio]-ethyl]-guanidine are heated under reflux in 45 ml of 20% hydrochloric acid for 6 hours. The reaction product is worked up by a method analogous to that of Example 109. It is initially obtained in the form of a dry, hygroscopic foam which gradually crystallises when triturated with acetone and a few drops of ethanol.

Yield: 0.77 g (93%), melting point 170° C. (decomposition),

Molar mass 304 (FAB-MS)

$C_{14}H_{20}N_6S.3HCl$ (413.8). Calc.: C 40.64 H 5.60 N 20.31. Found: C 40.58 H 5.70 N 20.00.

$^1$H-NMR data (d$_6$-DMSO, TMS as internal standard): $\delta = 1.87$ (m) 2 H, 2.74 (t) 2 H, 3.21 (dt) 2H, 3.35 (t) 2 H, 3.48 (dt) 2 H, 7.27 (dd) 1 H, 7.49 (s) 1 H, 7.51 (d) 1

H. 7.81 (m) 3 H, 2 H replaceable by D₂O, 8.13 (t) 1 H, replaceable by D₂O, 8.20 (t) 1 H, replaceable by D₂O, 8.52 (d) 1 H, 9.08 (s) 1 H, 14.6 (broad) 1 H, replaceable by D₂O, 14.9 (broad) 1 H, replaceable by D₂O, ppm.

EXAMPLE 118

N-Benzoyl-N'-[3-(imidazol-4-yl)propyl]-N''-[3-[(pyrid-2-yl)thio]propyl]-guanidine

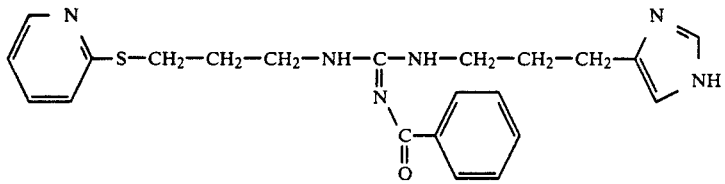

The method of preparation is analogous to that of Example 106, starting from 0.84 g (5 mmol) of 3-[(pyrid-2-yl)thio]-propylamine.

Yield: 1.5 g (71%), melting point 123° C. (ethyl acetate)

$C_{22}H_{26}N_6OS$ (422.6). Calc.: C 62.54 H 6.20 N 19.89. Found: C 62.52 H 6.19 N 19.87.

¹H-NMR data (CDCl₃, TMS as internal standard): δ = 1.92 (m) 2 H, 2.07 (m) 2 H, 2.67 (t) 2 H, 3.26 (t) 2 H, 3.45 (broad) 2 H, 3.62 (broad) 2 H, 6.74 (s) 1 H. 6.97 (dd) 1 H, 7.17 (d) 1 H, 7.35–7.55 (m) 5 H, 8.19 (m) 2 H, 8.38 (m) 1 H, ppm.

EXAMPLE 119

N-[3-(Imidazol-4-yl)propyl]-N'-[3-[(pyrid-2-yl)thio]-propyl]-guanidine

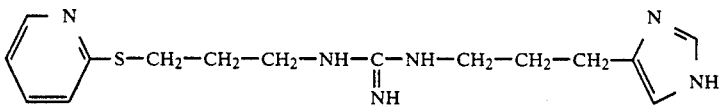

0.84 g (2 mmol) of N-benzoyl-N'[3-(imidazol-4-yl)propyl]-N''-[3-[(pyrid-2-yl)thio]propyl]-guanidine are heated under reflux in 45 ml of 20% hydrochloric acid for 6 hours. The reaction product is worked up by a method analogous to that of Example 109. It initially precipitates as a dry, hygroscopic foam but this foam gradually crystallises when triturated with acetone and a few drops of ethanol.

Yield: 0.76 g (89%), melting point 188° C.
Molar mass 318 (FAB-MS).
$C_{15}H_{22}N_6S.3HCl$ (427.8). Calc.: C 42.11 H 5.89 N 19.64. Found: C 41.99 H 5.99 N 19.29.

¹H-NMR data (d₆-DMSO, TMS as internal standard): δ = 1.86 (m) 4 H, 2.73 (t) 2 H, 3.15–3.4 (m) 6H, 7.25 (dd) 1 H, 7.49 (s) 1H, 7.51 (d) 1 H, 7.66 (s) 2 H, replaceable by D₂O, 7.81 (dd) 1 H, 8.03 (t) 1 H, replaceable by D₂O, 8.09 (t) 1 H, replaceable by D₂O, 8.50 (d) 1 H, 9.06 (s) 1 H, 14.5 (broad) 1 H, replaceable by D₂O, 14.8 (broad) 1 H, replaceable by D₂O, ppm.

EXAMPLE 120

N-Benzoyl-N'-[3-(imidazol-4-yl)propyl]-N''-[1-methyl-2-[(pyrid-2yl)methylthio]ethyl]-guanidine Preparation of preliminary stage 1-Methyl-2-[(pyrid-2-yl)methylthio]-ethylamine

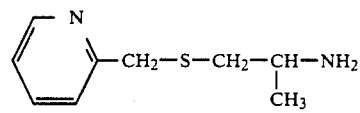

2.18 g (20 mmol) of 2-(hydroxymethyl)-pyridine and 2.55 g (20 mmol) of 2-mercapto-1-methylethylamine hydrochloride are heated under reflux in 50 ml 48% hydrobromic acid for 4 hours. The reaction mixture is then evaporated to dryness under vacuum and the residue is recrystallised from ethanol/water.

Yield: 5.5 g (80%), melting point 188° C.
$C_9H_{14}N_2S.2HBr$ (344.1). Calc.: C 31.41 H 4.69 N 8.14. Found: C 31.50 H 4.76 N 8.00.

¹H-NMR data (d₆-DMSO, TMS as internal standard): δ = 1.28 (d) 3 H, 2.77 (m) 2 H, 3.40 (m) 1 H, 4.24 (s) 2 H, 7.8–8.2 (m) 2H, 8.51 (m) 1 H, 8.82 (m) 1 H, ppm.

N-Benzoyl-N'-[3-(imidazol-4-yl)propyl]-N''-[1-methyl-2-(pyrid-2-yl)methylthio]ethyl]-guanidine

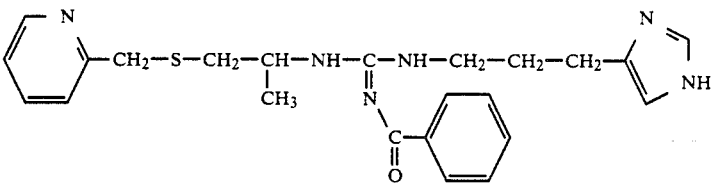

The method of preparation is analogous to that of Example 106, starting from 0.91 g (5 mmol) of 1-methyl-2-(pyrid-2-yl)methylthio]-ethylamine prepared from the dihydrobromide by reaction with sodium ethylate in ethanol.

Yield: 1.2 g (55%) of a viscous oil
$C_{23}H_{28}N_6OS$ (436.6)
MS (FAB method): m/z (rel. Int.[%]) = 437 ([M+H]⁺, 54), 166(13), 124(100), 109(34), 105(98).

¹H-NMR data (CDCl₃, TMS as internal standard): δ = 1.32 (d)3 H, 1.93 (m) 2 H, 2.5–3.1 (m) 4 H, 3.2–4.0 (m) 5 H, 6.75 (s) 1 H, 6.9–7.8 (m) 7 H, 8.17 (m) 2 H, 8.46 (m) 1 H, ppm.

EXAMPLE 121

N-[3-(Imidazol-4-yl)propyl]-N'-[1-methyl-2-[(pyrid-2-yl) methylthio]-ethyl]-guanidine

[Structure: pyridine-CH2-S-CH2-CH(CH3)-NH-C(=NH)-NH-CH2-CH2-CH2-imidazole]

The method of preparation is analogous to that of Example 109, starting from 0.74 g (1.7 mmol) of N-benzoyl-N'-[3-(imidazol-4-yl)propyl]-N''-[1-methyl-2-[(pyrid-2-yl) methylthio]-ethyl]-guanidine.

Yield: 0.68 g (91%) of hygroscopic, non-crystalline solid.

$C_{16}H_{24}N_6S \cdot 3HCl$ (441.8)

MS (FAB method): m/z (rel. Int. [%])=333 ([M+H]+,100), 208(6), 124(55), 109(47).

$^1$H-NMR data (d$_6$-DMSO, TMS as internal standard): δ=1.17 (d) 3 H, 1.87 (m) 2 H, 2.65–2.85 (m) 4 H, 3.22 (dt) 2 H, 4.09 (m) 1 H, 4.30 (m) 2 H, 7.51 (s) 1 H, 7.71 (s) 2 H, replaceable by D$_2$O, 7.90 (m) 2 H, 1 H replaceable by D$_2$O, 8.10 (m) 2 H, 1 H replaceable by D$_2$O, 8.50 (dd) 1 H, 8.82 (d) 1 H, 9.07 (s) 1 H, 14.6 (broad) H, replaceable by D$_2$O, 14.9 (broad) 1 H, replaceable by D$_2$O, ppm.

EXAMPLE 122

N-Benzoyl-N'[3-(imidazol-4-yl)propyl]-N''2-[(phenyl(-pyrid-2-yl)methyl)thio]-ethyl]-guanidine

[Structure: pyridine-CH(phenyl)-S-CH2-CH2-NH-C(=N-C(=O)-phenyl)-NH-CH2-CH2-CH2-imidazole]

The method of preparation is analogous to that of Example 106, starting from 1.25 g (5 mmol) of 2-[[phenyl (pyrid-2-yl)methyl]-thio]-ethylamine.

Yield: 1.2 g (48%), melting point 134° C. (ethyl acetate).

$C_{28}H_{30}N_6OS$ (498.7). Calc.: C 67.44 H 6.06 N 16.85. Found: C 67.12 H 6.10 N 16.62.

$^1$H-NMR data (CDCl$_3$, TMS as internal standard): δ=1.89 (m) 2 H, 2.64 (t) 2 H, 2.73 (t) 2 H, 3.3 (broad) 2 H, 3.65 (broad) 2 H, 5.34 (s) 1 H, 6.72 (s) 1 H, 7.05–7.65 (m) 10 H, 8.17 (d) 2 H, 8.51 (d) 1 H, ppm.

EXAMPLE 123

N-[3-(Imidazol-4-yl)propyl]-N'-[2-[(phenyl(pyrid-2-yl)methyl)thio]ethyl]-guanidine

[Structure: pyridine-CH(phenyl)-S-CH2-CH2-NH-C(=NH)-NH-CH2-CH2-CH2-imidazole]

The method of preparation is analogous to that of Example 109, starting from 0.85 g (1.7 mmol) of N-benzoyl-N'-[3-(imidazol-4-yl)propyl]-N''-[2-[(phenyl)-pyrid-2-yl) methyl)thio]ethyl]-guanidine.

Yield: 0.78 g (91%) of a hygroscopic, non-crystalline solid.

$C_{21}H_{26}N_6S \cdot 3HCl$ (503.9)

MS (FAB method): m/z (rel. Int. [%])=395 ([M+H]+38), 168(100), 109(21)

$^1$H-NMR data (d$_6$-DMSO, TMS as internal standard): δ=1.83 (m) 2 H, 2.57 (t) 2 H, 2.70 (t) 2 H, 3.18 (dt) 2 H, 3.44 (dt) 2 H, 5.87 (s) 1 H, 7.2–7.8 (m) 10 H, 2 H replaceable by D$_2$O, 7.87 (m) 2 H, 1 H replaceable by D$_2$O, 8.10 (m) 2 H,1 H replaceable by D$_2$O, 9.05 (s) 1 H, 14.4 (broad) 1 H, replaceable by D$_2$O, 14.7 (broad) 1 H, replaceable by D$_2$O, ppm.

EXAMPLE 124

N-[2-[(5-Chloro-2-thenyl)thio]ethyl]-N'-[3-(imidazol-4-yl)propyl]-guanidine

Preparation of the preliminary stages a) 2-[(5-Chloro-2-thenyl)thio]ethylamine

[Structure: 5-chlorothiophene-CH2-S-CH2-CH2-NH2]

3.41 g (30 mmol) of cysteamine hydrochloride are introduced under a current of nitrogen into a solution of 1.38 g (60 mmol) of sodium in 100 ml of methanol. 5.01 g (30 mmol) of 5-chloro-2-(chloromethyl)thiophene are added after 10 minutes, stirring at room temperature. The solvent is distilled off under vacuum after one hour and the residue is dissolved in 5% hydrochloric acid and extracted with ether.

After alkalization with sodium hydroxide solution, the aqueous phase is extracted by shaking with methylene chloride and the organic phase is washed with water, dehydrated over sodium sulphate and concentrated by evaporation under vacuum. The oily amine base left as residue is converted into the hydrochloride by reaction with ethanolic hydrochloric acid and recrystallised from ethanol/water.

Yield: 4.0 g (55%) melting point 166° C.
C$_7$H$_{10}$ClNS$_2$.HCl (244.2). Calc.: C 34.43 H 4.54 N 5.74. Found: C 34.41 H 4.63 N 5.79.

$^1$H-NMR data (d$_6$-DMSO, TMS as internal standard): δ=2.6–3.15 (m) 4 H, 3.98 (s) 2 H, 6.86 (d) 1 H, 6.95 (d) 1 H. ppm.

b) N-Benzoyl-N'-[2-[(5-chloro-2-thenyl)thio]ethyl]-thiourea

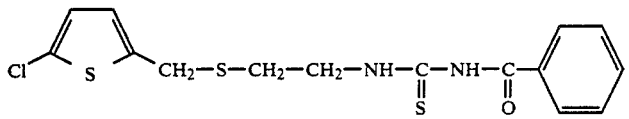

2.07 g (10 mmol) of 2-[(5-Chloro-2-thenyl)thio]-ethylamine hydrochloride are converted into the base by reaction with the equivalent quantity of sodium ethylate in ethanol. After the precipitated sodium chloride has been filtered off and the ethanolic solution has been concentrated by evaporation under vacuum, the base is reacted with 1.63 g (10 mmol) of benzoyl isothiocyanate by a method analogous to that of Example 105 (preliminary stage a).

Yield: 3.3 g (89%), melting point 104° C. (ethanol/water)

C$_{15}$H$_{15}$ClN$_2$OS$_3$ (370.9). Calc.: C 48.57 H 4.08 N 7.55. Found: C 48.48 H 4.13 N 7.64.

$^1$H-NMR data (CDCl$_3$, TMS as internal standard): δ=2.84 (t) 2 H, 3.91 (s) 2 H, 3.91 (dt) 2 H, 6.72 (d) 1 H, 6.78 (d) 1 H, 7.52 (m) 2 H, 7.64 (m) 1 H, 7.85 (m) 2 H, 9.05 (broad) 1 H, replaceable by D$_2$O, 11.0 (broad) 1 H, replaceable by D$_2$O, ppm.

c) N'-[2-[(5-Chloro-2-thenyl)thio]ethyl]-thiourea

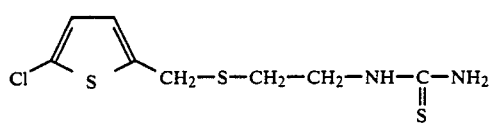

2.78 g (7.5 mmol) of N-benzoyl-N'-[2-[(5-chloro-2-thenyl)thio]ethyl]-thiourea and 2.1 9 of potassium carbonate are heated together under reflux in a mixture of 30 ml of water and 100 ml of methanol for one hour. The reaction mixture is then concentrated by evaporation under vacuum and the residue is crystallised from ethanol/water.

Yield: 1.8 g (90%), melting point 63° C.
C$_8$H$_{11}$ClN$_2$S$_3$ (266.8). Calc.: C 36.01 H 4.16 N 10.50. Found: C 36.25 H 4.23 N 10.59.

$^1$NMR data (CDCl$_3$, TMS as internal standard): δ=2.74 (t) 2 H, 3.7 (broad) 2 H, 3.87 (s) 2 H, 5.99 (s) 2 H, replaceable by D$_2$O, 6.65–6.8 (m) 3 H, 1 H replaceable by D$_2$O, ppm.

d) N-[2-[(5-Chloro-2-thenyl)thio]ethyl]-S-methyl-isothiouronium iodide

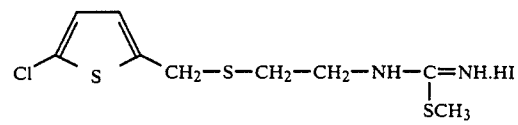

1.33 g (5 mmol) of N-[2-[(5-Chloro-2.thenyl)thio]ethyl]-thiourea and 0.4 ml of methyl iodide in 100 ml of ethanol are stirred overnight at room temperature. 2.0 g (98%) of thin layer chromatographically pure oil are obtained as residue after removal of the solvent by evaporation under vacuum.

C$_9$H$_{13}$ClN$_2$S$_3$.HI (408.8). Molar mass (MS): Calc. 279.99295, Found 279.99234.

MS (FAB method): m/z (rel. Int. [%]) =281 ([M+H]$^+$,72), 131(100), 103(10).

$^1$H-NMR data (d$_6$-DMSO, TMS as internal standard): δ2.66 (s) 3 H, 2.72 (t) 2 H, 3.56 (t) 2 H, 4.03 (s) 2 H, 6.95 (m) 2 H, 9.1 (broad) 3 H, replaceable by D$_2$O, ppm.

N-[2-[(5-Chloro-2-thenyl)thio]ethyl]-N'[3-(imidazol-4-yl) propyl]-guanidine

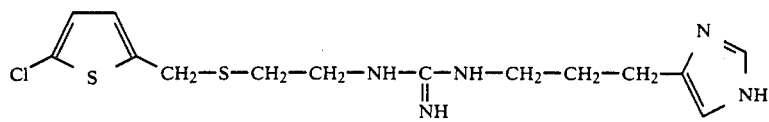

The compound is prepared and isolated by a method analogous to that of Example 105, starting from 1.43 g (3.5 mmol) of N-[[2-(5-chloro-2-thenyl)thio]ethyl]-S-methyl-isothiouronium iodide.

Yield: 0.87 g (51%) of a viscous oil
C$_{14}$H$_{20}$ClN$_5$S$_2$.HI (485.8)

MS (FAB method): m/z (rel. Int. [%])=358 ([M+H]$^+$,94), 131(100), 109(94).

$^1$H-NMR data (d$_6$-DMSO, TMS as internal standard): δ=1.79 (m) 2 H, 2.56 (t) 2 H, 2.63 (t) 2 H, 3.19 (dt) 2 H, 3.37 (dt) 2 H, 4.01 (s) 2 H, 6.90 (d) 1 H, 6.95 (s) 1 H, 6.97 (d) 1 H, 7.86 (s) 1 H, ppm.

EXAMPLE 125

N-[3-(Imidazol-4-yl)propyl]-N'-[2-[(5-piperidinomethyl-2-thenyl)thio]ethyl]-guanidine Preparation of the preliminary stage N-Benzoyl-N'-[2-[(5-piperidinomethyl 2-thenyl)thio]ethyl]thiourea

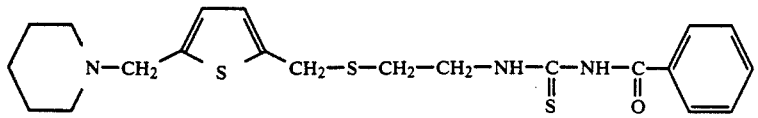

The method of preparation is analogous to that of Example 105 (preliminary stage a), starting from 2.7 g (10 mmol) of 2-[(5-piperidinomethyl-2-thenyl)thio]ethylamine.

Yield: 3.95 g (91%), melting point 83° C. (methanol/water).

$C_{21}H_{27}N_3OS_3$ (433.7) Calc.: C 58.16 H 6.28 N 9.69. Found: C 58.35 H 6.39 N 9.65.

¹H-NMR data (CDCl₃, TMS as internal standard): δ=1.42 (m) 2 H, 1.57 (m) 4 H, 2.41 (m) 4 H, 2.84 (t) 2 H, 3.62 (s) 2 H, 3.90 (dt) 2 H, 3.96 (s) 2 H, 6.70 (d) 1 H, 6.82 (d) 1 H, 7.52 (m) 2 H, 7.64 (m) 1 H, 7.86 (d) 2 H, 9.05 (broad) 1 H, replaceable by D₂O, 10.97 (broad) 1 H, replaceable by D₂O, ppm.

N-[3-(Imidazol-4-yl)propyl]-N'-[2-[(5-piperidinomethyl-2-thenyl)thio]ethyl]-guanidine

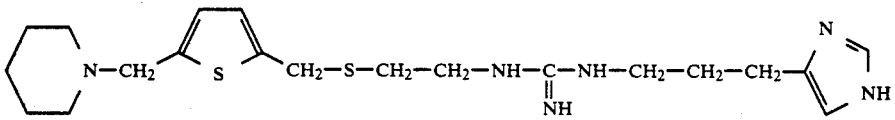

2.17 g (5 mmol) of N-benzoyl-N'-[2-[(5-piperidinomethyl-2-thenyl)thio]ethyl]thiourea and 1.4 g of potassium carbonate are heated together under reflux in a mixture of ml of water and 100 ml of methanol for one hour. The solvent is then distilled off under vacuum and the residue is taken up with ether, and the organic phase is washed with water, dehydrated over sodium sulphate, concentrated by evaporation under vacuum and stirred overnight at room temperature with the addition of 0.4 ml of methyl iodide in 100 ml of ethanol. The solvent is distilled off under vacuum and the oily residue is heated under reflux with 0.69 g (5.5 mmol) of 3-(imidazol-4-yl)propylamine in 30 ml of pyridine for 3 hours. The reaction mixture is then concentrated by evaporation under vacuum and the product is isolated and purified by preparative layer chromotography (silica gel 60 PF₂₅₄ containing gypsum: solvent: chloroform/methanol 85+15 (ammoniacal atmosphere). When the eluates have been concentrated by evaporation, 0.78 g (28%) of the hydriodide is obtained as residue in the form of a viscous oil.

$C_{20}H_{32}N_6S_2 \cdot HI$ (548.5)

MS (FAB method): m/z (rel. Int. [%])=421 ([M+H]⁺, 37), 336(4), 194(41), 141(24), 109(61), 100(17), 98(100), 84(24).

¹H-NMR data (d₆-DMSO, TMS as internal standard): δ=1.2-2.1 (m) 8 H, 2.1-2.9 (m) 8 H, 2.9-3.7 (m) 4 H, 3.49 (s) 2 H, 3.91 (s) 2 H, 6.6-6.9 (m) 3 H, 7.48 (d) 1 H, ppm

EXAMPLE 126

N-Benzoyl-N'-[3-(imidazol-4-yl)propyl]-N''-[3-phenyl-3-(pyrid-2-yl)propyl]-guanidine

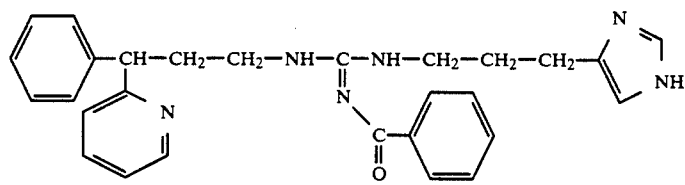

The method of preparation is analogous to that of Example 106, starting from 1.06 g (5 mmol) of 3-phenyl-3-(pyrid-2-yl)-propylamine.

Yield: 1.3 g (56%) of non-crystalline solid (foam)

$C_{28}H_{30}N_6O$ (466.6)

MS (FAB method): m/z (rel. Int. [%])=467 ([M+H]+20). 196(87), 109(30), 105(100), 77(28).

¹H-NMR data (CDCl₃, TMS as internal standard): δ=1.96 (m) 2 H, 2.32 (broad) 1 H, 2.70 (m) 3 H, 3.1-4.05 (m) 4 H, 4.20 (m) 1 H, 6.73 (s) 1 H, 7.0-7.7 (m) 12 H, 8.13 (m) 2 H, 8.57 (m) 1 H, ppm.

EXAMPLE 127

N-[3-(Imidazol-4-yl)propyl]-N'[3-phenyl 3-(pyrid-2-yl)) propyl]-guanidine

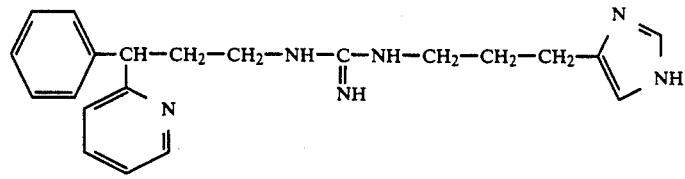

The method of preparation is analogous to that of Example 109, starting from 0.93 g (2 mmol) of N-benzoyl-N'-[3 (imidazol-4-yl)propyl]-N''-[3-phenyl-3-(pyrid-2-yl) propyl]-guanidine.

Yield: 0.86 g (91%) of a hygroscopic, non-crystalline solid

C₂₁H₂₆N₆.3HCl (471.9) Molar mass (MS): Calc.: 362.22189, Found: 362.2223.

MS (FAB method): m/z (rel. Int. [%])=363 ([M+H]⁺,89), 196(100), 168(32), 109(40), 100(26).

¹H-NMR data (d₆-DMSO, TMS as internal standard): δ=1.84 (m) 2 H, 2.3–2.7 (m) 2 H, 2.72 (t) 2 H, 3.0–3.3 (m) 4 H, 4.67 (t) 1 H. 7.2–7.65 (m) 8 H, 2 H replaceable by D₂O, 7.74 (dd) 1 H, 7.98 (m) 3 H, 2 H replaceable by D₂O, 8.32 (m) 1 H, 8.74 (d) 1 H, 9.04 (s) 1 H, 14.4 (broad) 1 H, replaceable by D₂O, 14.7 (broad) 1 H, replaceable by D₂O, ppm.

EXAMPLE 128

N-Benzoyl-N'-[3-(4-chlorophenyl)-3-(pyrid-2-yl)propyl]-N''-[3-(imidazol-4-yl)propyl]-guanidine

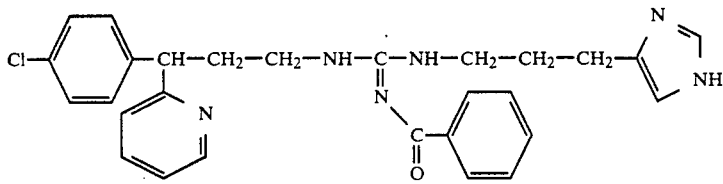

The method of preparation is analogous to that of Example 106, starting from 1.23 g (5 mmol) of 3-(4-chlorophenyl)-3-pyrid-2-yl)-propylamine.

Yield: 1.4 g (56%) of a non-crystalline solid (foam). C₂₈H₂₉ClN₆O (501.0)

MS (FAB method): m/z (rel. Int. [%])=501 ([M+H]⁺, 20), 230(58), 167(19), 109(37), 105(100), 77(28).

¹H-NMR data (CDCl₃, TMS as internal standard): δ1.96 (m) 2 H, 2.3 (broad) 1 H, 2.55–2.8 (m) 1 H, 2.70 (t) 2 H, 3.1–4.0 (m) 4 H, 4.18 (dd) 1 H, 6.73 (s) 1 H, 7.0–7.7 (m) 11 H, 8.12 (m) 2 H, 8.57 (m) 1 H, ppm.

EXAMPLE 129

N-[3-(4-Chlorophenyl)-3-(pyrid-2-yl)propyl]-N'-[3-(imidazol -4-yl)propyl]-guanidine

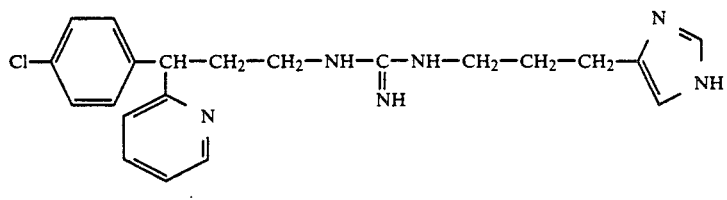

The method of preparation is analogous to that of Example 109 from 1.0 9 (2 mmol) of N-benzoyl-[3-(4-chlorophenyl)-3-(pyrid-2-yl)propyl]-N''-[3-(imidazol-4-yl) propyl]-guanidine Yield: 0.95 g (94%) of a hygroscopic, non-crystalline solid.

C₂₁H₂₅ClN₆.3HCl (506.3). Molar mass (MS): Calc.: 396.18292, Found: 396.18237.

MS: m/z (rel. Int.[%])=396 (M⁺,2), 315(14), 230(31), 216(57), 203(100), 194(41), 167(41), 109(16), 95(22), 81(14).

¹H-NMR data (d₆-DMSO, TMS as internal standard): δ=1.84 (m) 2 H, 2.41 (m) 1 H, 2.55 (m) 1 H, 2.72 (t) 2 H, 3.11 (dt) 2 H, 3.18 (dt) 2 H, 4.70 (t) 1 H, 7.35–7.65 (m) 7 H, 2 H replaceable by D₂O, 7.74 (dd) 1 H, 7.96 (m) 3 H, 2 H replaceable by D₂O, 8.33 (dd) 1 H, 8.74 (d) 1 H, 9.05 (s) 1 H, 14.4 (broad) 1 H, replaceable by D₂O, 14.7 (broad) 1 H, replaceable by D₂O, ppm.

EXAMPLE 130

N-Benzoyl-N'-[3-(4-bromophenyl)-3-(pyrid-2-yl)propyl]-N''-[3-imidazol-4-yl)propyl]-guanidine

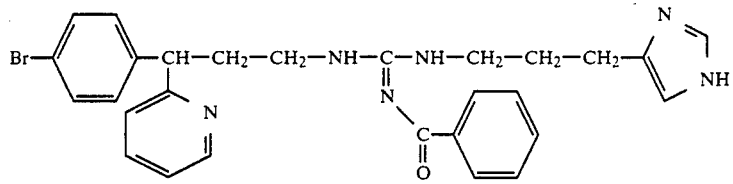

The method of preparation is analogous to that of starting from 1.46 g (5 mmol) of 3-(4-bromo-3-(pyrid-2-yl)-propylamine.

Yield: 1.3 g (48%) of a non-crystalline solid (foam). C₂₈H₂₉BrN₆O (545.5)

MS (FAB method): m/z (rel. Int. [%])=545 ([M+H]⁺,8), 274(36), 167(16). 109(40), 105(100), 81(11), 77(23).

¹H-NMR data (CDCl₃, TMS as internal standard): δ=1.96 (m) 2 H, 2.3 (broad) 1 H, 2.5–2.8 (m) 3 H, 3.1–4.05 (m) 4 H, 4.17 (dd) 1 H, 6.74 (s) 1 H, 6.9–7.7 (m) 11 H, 8.12 (m) 2 H, 8.57 (m) 1 H, ppm.

EXAMPLE 131

N-[3-(4-Bromophenyl)-3-(pyrid-2-yl)propyl]-N'-[3-(imidazol-4-yl)propyl]-guanidine

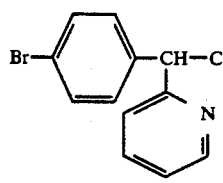
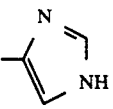

The compound is prepared by a method analogous to that of Example 109 from 1.09 g (2 mmol) of N-benzoyl-N'-[3-(4-bromophenyl)-3-(pyrid-2-yl)propyl]-N''-[3-(imidazol-4-yl)propyl]-guanidine.

Yield: 0.98 g (89%) of a hygroscopic, non-crystalline solid.

$C_{21}H_{25}BrN_6 \cdot 3HCl$ (550.8). Molar mass (MS): Calc.: 440.13242, Found: 440.13283.

MS: m/z (rel. Int.[%]) = 440 (M+, 1) 359(7), 260(36), 247(100), 194(70), 180(29), 167(61), 109(18), 95(43), 81(32).

$^1$H-NMR data (d$_6$-DMSO, TMS as internal standard): δ = 1.85 (m) 2 H, 2.40 (m) 1 H, 2.55 (m) 1 H, 2.73 (t) 2 H, 3.12 (dt) 2 H, 3.20 (dt) 2 H, 4.66 (t) 1 H, 7.45–7.8 (m) 8 H, 2 H replaceable by D$_2$O, 7.85–8.1 (m) 3H, 2 H replaceable by D$_2$O, 8.28 (m) 1 H, 8.72 (d) 1 H, 9.05 (s) 1 H. 14.4 (broad) 1 H, replaceable by D$_2$O, 14.8 (broad) 1 H, replaceable by D$_2$O, ppm.

EXAMPLE 132

N-Benzoyl-N'-[3-(4-fluorophenyl)-3-(pyrid-2-yl)propyl]N''-[3-(imidazol-4-yl)propyl]-guanidine Preparation of the preliminary stages a)     N-[3-(Cyano-3-(4-fluorophenyl)-3-(pyrid-2-yl)propyl]-phthalimide

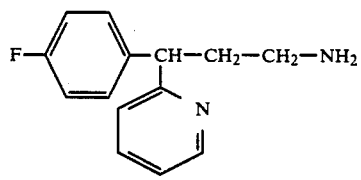

42.4 g (0.2 mol) of (4-Fluorophenyl)-pyrid-2-yl)-acetonitrile are dissolved in 50 ml of dimethylformamide and introduced dropwise into a suspension, cooled with ice, of 5.0 g of sodium hydride (put into the process as a dispersion in mineral oil) in 150 ml of dimethylformamide. The reaction mixture is then stirred at room temperature for 15 minutes and thereafter heated under reflux for 5 hours after the addition of 53.4 g (0.21 mol) of N-(2-bromoethyl)-phthalimide. When the resulting reaction mixture has cooled down, it is diluted with 500 ml of ether and the organic phase is washed with water until neutral, dehydrated over sodium sulphate and then concentrated by evaporation under vacuum. The oily residue crystallises on addition of methanol.

Yield: 48.5 g (63%). melting point 154° C. (methanol).
$C_{23}H_{16}FN_3O_2$ (385.4) Calc.: C 71.68 H 4.18 N 10.90. Found: C 71.59 H 3.87 N 11.07.

IR (KBr): 2240, 1770, 1715, 1605, 1585, 1570 cm$^{-1}$.

$^1$H-NMR data (CDCl$_3$, TMS as internal standard): δ = 2.9 (m) 2 H, 3.88 (m) 2 H, 6.8–8.0 (m) 11 H 8.55 (m) 1 H, ppm.

b) 3-(4-Fluorophenyl)-3-(pyrid-2-yl)-propylamine

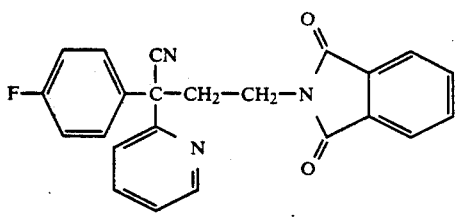

46.25 g (0.12 mol) of N-[3-Cyano-3-(4-fluorophenyl)-3-(pyrid-2-yl)propyl]-phthalimide in 100 ml of 75% sulphuric acid are heated to 150° C. for 5 hours. When the reaction mixture is cold, it is poured out on ice, filtered through a glass frit, alkalized with sodium hydroxide solution and extracted with ether. The combined extracts are washed with water, dehydrated over sodium sulphate and concentrated by evaporation under vacuum, and the product obtained is isolated by distillation at 150°–155° C./0.8 mm Hg.

Yield: 19.1 g (69%) of thin layer chromatographically pure oil.

$C_{14}H_{15}FN_2$ (230.3) Molar mass (MS): Calc.: 230.12193, Found: 230.12174

MS: m/z (rel. Int. [%]) = 230 (M+, 2), 229(2), 212(4), 200(32), 187(100).

$^1$H-NMR data (CDCl$_3$, TMS as internal standard): δ = 1.7 (broad) 2 H, replaceable by D$_2$O, 2.17 (m) 1 H, 2.38 (m) 1 H, 2.64 (t) 2 H, 4.17 (t) 1 H, 6.97 (dd) 2 H, 7.09 (dd) 1 H, 7.14 (d) 1 H, 7.31 (dd) 2 H, 7.56 (dd) 1 H, 8.56 (d) 1 H, ppm.

N-Benzoyl-N'-[3-(4-fluorophenyl)-3-(pyrid-2-yl)propyl]-N''-[3-(imidazol-4-yl)propyl]-guanidine

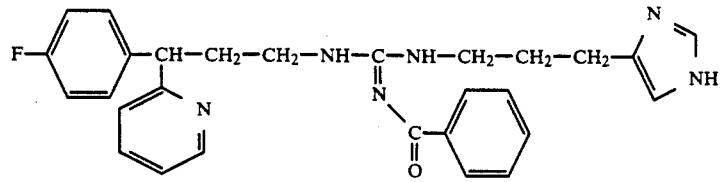

The method of preparation is analogous to that of Example 106, starting from 1.15 g (5 mmol) of 3-(4-fluorophenyl)-3-pyrid-2-yl)-propylamine.

Yield: 1.4 g (58%) of a non-crystalline solid (foam).

C₂₈H₂₉FN₆O (484.6)

MS (FAB method): m/z (rel. Int. [%])=485 ([M+H]⁺,29), 214(93), 186(24), 109(31), 105(100), 77(29).

¹H-NMR data (CDCl₃, TMS as internal standard): δ=1.97 (m) 2 H, 2.3 (broad) 1 H, 2.5-2.8 (m) 3 H, 3.0-4.1 (m) 4 H, 4.18 (dd) 1 H, 6.72 (s) 1 H, 6.8-7.8 (m) 11 H, 8.12 (m) 2 H, 8.56 (m) 1 H, ppm.

EXAMPLE 133

N-[3-(4-Fluorophenyl)-3-(pyrid-2-yl)propyl]-N'-[3-(imidazol-4-yl)propyl]-guanidine

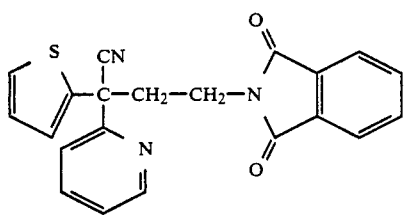

The compound is prepared by a method analogous to that of Example 109 from 0.97 g (2 mmol) of N-benzoyl-N'-[3-(4-fluorophenyl)-3-(pyrid-2-yl)propyl]-N''-[3-(imidazol4-yl)propyl]-guanidine.

Yield: 0.9 g (92%) of a hygroscopic, non-crystalline C₂₁H₂₅FN₆.3HCl (489.9)

MS (FAB method): m/z (rel. Int. [%])=381 ([M+H]⁺, 100), 256(40), 214(86), 186(20), 109(44), 100(28).

¹H-NMR data (d₆-DMSO, TMS as internal standard): δ=1.83 (m) 2 H, 2.39 (m) 1 H, 2.55 (m) 1 H, 2.71 (t) 2 H, 3.09 (dt) 2 H, 3.17 (dt) 2 H, 4.68 (t) 1 H, 7.19 (dd) 2 H, 7.49 (s) 1 H, 7.56 (m) 4 H, 2 H replaceable by D₂O, 7.71 (m) 1 H, 7.95 (m) 3 H, 2 H replaceable by D₂O, 8.29 (m) 1 H, 8.72 (m) 1 H, 9.04 (s) 1 H, 14.4 (broad) 1 H, replaceable by D₂O, 14.8 (broad) 1 H. replaceable by D₂O, ppm.

EXAMPLE 134

N-[3-(Imidazol-4-yl)propyl]-N'-[3-(pyrid-2-yl)-3-(2-thienyl) propyl]-guanidine

Preparation of the preliminary stages a) N-[3-Cyano-3-(pyrid-2-yl)-3-(2-thienyl)propyl]-phthalimide

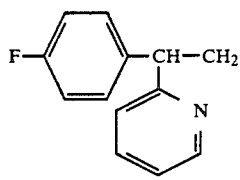

The method of preparation is analogous to that of Example 132 (preliminary stage a) starting from 20.0 g (0.1 mol) of (pyrid-2-yl)-(2-thienyl)-acetonitrile.

Yield: 12.3 g (33%), melting point 104° C. (ethanol) C₂₁H₁₅N₃O₂S (373.4). Calc.: C 67.54 H 4.05 N 11.25. Found: C 67.27 H 3.87 N 11.18.

IR (KBr): 2245, 1770, 1720, 1615, 1586, 1572 cm⁻¹.

¹H-NMR data (CDCl₃, TMS as internal standard): δ=2.95 (m) 2 H, 3.90 (t) 2 6.8-7.4 (m) 6 H, 7.5-7.9 (m) 6H 8.57 (m) 1H, ppm.

b) 3-Pyrid-2-yl)-3-(2-thienyl)-propylamine

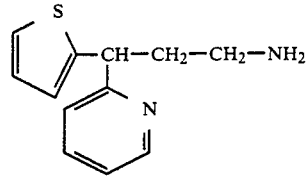

11.2 g (30 mmol) of N-[3-Cyano-3-(pyrid-2-yl)-3-(2-thienyl)-propyl]-phthalimide are heated under reflux with 30 g of potassium hydroxide in 100 ml of butanol for 8 hours. The reaction product is then diluted with ml of ether, washed with water, dehydrated over sodium sulphate, concentrated by evaporation under vacuum and distilled at 145°-148° C./0.8.

Yield: 3.8 g (58%) of thin layer chromatographically pure oil.

C₁₂H₁₄N₂S (218.3) Molar mass (MS): Calc.: 218,08777, Found: 218.08779.

MS: m/z (rel. Int. [%])=218 (M⁺, 20), 201(14), 188(100). 175(69).

¹H-NMR data (CDCl₃, TMS as internal standard): δ=1.6 (broad) 2 H, replaceable by D₂O, 2.2-2.45 (m) 2H, 2.67 (t) 2 H, 4.48 (t) 1 H, 6.93 (m) 2 H, 7.1-7.25 (m) 3 H. 7.60 (m) 1 H, 8.57 (m) 1 H, ppm.

c) N-Benzoyl-(N'-[3-(pyrid-2-yl)-3-(2-thienyl)propyl]-thiourea

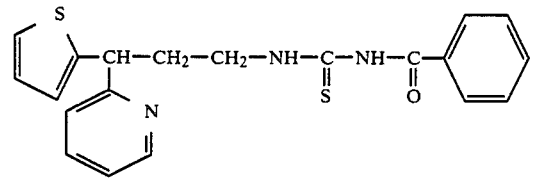

2.18 g (10 mmol) of 3-(pyrid-2-yl)-3-(2-thienyl)-propylamine are heated under reflux with 1.63 g (10 mmol) of benzoyl isothiocyanate in 100 ml of chloroform for one hour. The solvent is distilled off under vacuum and the residue is crystallised from ethanol.

Yield: 3.43 g (90%), melting point 95° C.

C₂₀H₁₉N₃OS₂ (381.5). Calc.: C 62.96 H 5.02 N 11.01. Found: C 62.63 H 4.85 N 11.06.

¹H-NMR data (CDCl₃, TMS as internal standard): δ=2.57 (m) 1 H, 2.71 (m) 1 H, 3.73 (dt) 2 H, 4.48 (t) 1 H, 6.9-7.05 (m) 2 H, 7.1-7.3 (m) 3 H, 7.45-7.7 (m) 4 H, 7.84 (m) 2 H, 8.61 (m) 1 H, 9.00 (s) 1 H, replaceable by D₂O, 10.8 (broad) 1 H, replaceable by D₂O, ppm.

d) N-[3-(Pyrid-2-yl)-3-(2-thienyl)-propyl]-thiourea

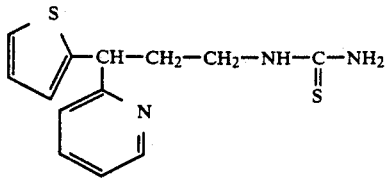

4.51 (t) 1 H, 6.95–7.05 (m) 2 H, 7.2–7.5 (m) 3 H, 7.78 (m) 1 H, 8.57 (m) 1 H. 9.1 (broad) 3 H, replaceable by D₂O, ppm.

N-[3-(Imidazol-4-yl)propyl]-N'-[3-(pyrid-2-yl)-3-(2thienyl)propyl]-guanidine

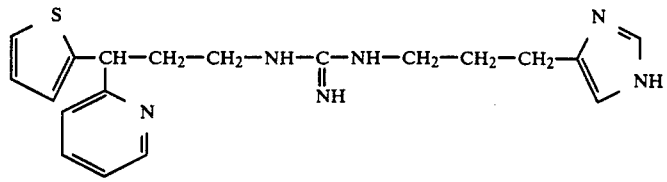

The method of preparation is analogous to that of Example 105, starting from 1.47 g (3.5 mmol) of S-methyl-N-[3-(pyrid-2-yl)-3-(2-thienyl)propyl]-isothiouronium iodide.

Yield: 0.89 g (51%) of a hygroscopic, non-crystalline solid.

C₁₉H₂₄N₆S.HI (496.4) Molar mass (S): Calc.: 368.17832, Found: 368.1787.

MS (FAB method): m/z (rel. Int.[%])=369 ([M+H]+,100), 202(97), 188(10), 174(18), 109(49), 100(33), 78(69).

¹H-NMR data (d₆-DMSO, TMS as internal standard): δ=1.78 (m) 2 H, 2.23 (m) 1 H, 2.44 (m) 1 H, 2.60 (t) 2 H, 3.06 (broad) 2 H. 3.16 (dt) 2 H, 6.9–7.05 (m) 2 H, 7.16 (s) 1 H, 7.28 (dd) 1 H, 7.3–7.55 (m) 6 H, 4 H replaceable by D₂O, 7.77 (m) 1 H, 8.33 (s) 1 H, 8.56 (m) 1 H, ppm.

The compound is prepared by a method analogous to that of Example 124 (preliminary stage c) from 2.86 g (7.5 mmol) of N-benzoyl-N'-[3-(pyrid-2-yl)-3-(2-thienyl) propyl]-thiourea.

Yield: 1.93 g (93%), melting point 138° C. (ethanol).

C₁₃H₁₅N₃S₂ (277.4). Calc.: C 56.29 H 5.45 N 15.15. Found: C 56.28 H 5.44 N 15.21.

¹H-NMR data (CDCl₃ TMS as internal standard): δ=2.4 (broad) 1 H, 2.55 (broad) 1 H, 3.1–3.5 (m) 2 H, 4.48 (m) 1 H, 6.8–7.5 (m) 8 H, 3 H replaceable by D₂O, 7.65 (m) 1 H, 8.51 (m) 1 H, ppm.

e) S-Methyl-N-[3-(pyrid-2 yl)-3-(2-thienyl)propyl]-isothiouronium iodide

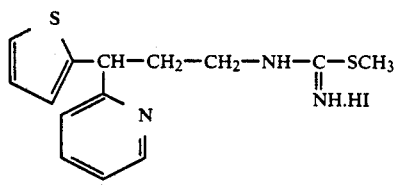

EXAMPLE 135

N-Benzoyl-N'-[3-(imidazol-4-yl)propyl]-N''-[4-phenyl-4-(pyrid-2-yl)butyl]-guanidine

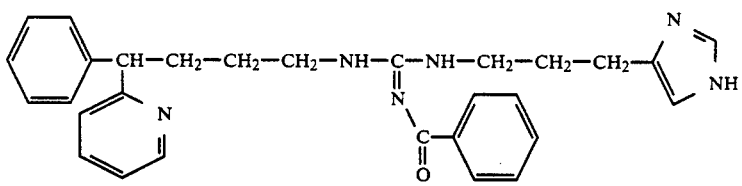

1.39 g (5 mmol) of N-[3-(pyrid-2-yl)-3-(2-thienyl) propyl]-thiourea are stirred overnight with 0.4 ml of methyl iodide in 100 ml of ethanol at room temperature. The solvent is distilled off under vacuum and the residue is crystallised from ethanol/ether.

Yield: 1.78 g (85%), melting point 158° C.

C₁₄H₁₇N₃S₂.HI (419.3). Calc.: C 40.10 H 4.33 N 10.02. Found: C 40.17 H 4.31 N 10.05.

¹H-NMR data (d₆-DMSO, TMS as internal standard): δ=2.25–2.7 (m) 2 H, 2.60 (s) 3 H, 3.24 (m) 2 H, The method of preparation is analogous to that of Example 106, starting from 1.13 g (5 mmol) of 4-phenyl-4-(pyrid-2-yl)-butylamine.

Yield: 1.2 g (50%) of a non-crystalline solid (foam).

C₂₉H₃₂N₆O (480.6)

MS (FAB method): m/z (rel. Int.[%])=481 ([M+H]+,18), 210(47), 109(38), 105(100), 77(31).

¹H-NMR data (CDCl₃, TMS as internal standard): δ=1.64 (m) 2 H, 1.90 (m) 2.H, 2.17 (m) 1 H. 2.36 (m) 1 H, 2.66 (t) 2 H, 3.1–3.8 (m) 4 H, 4.11 (t) 1 H, 6.74 (s) 1 H, 7.0–7.65 (m) 12 H, 8.17 (m) 2 H, 8.54 (m) 1 H, ppm.

EXAMPLE 136

N-[3-(Imidazol-4-yl)propyl]-N'-[4-phenyl-4-(pyrid-2-yl)butyl]-guanidine

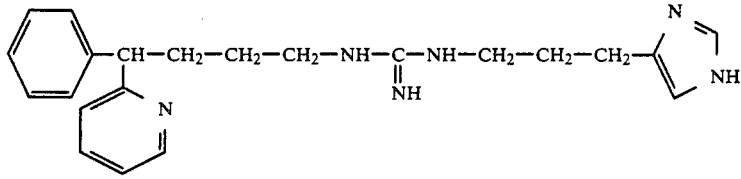

The method of preparation is analogous to that of Example 109 starting from 0.96 g (2 mmol) of N-benzoyl-N'-[3-(imidazol-4-yl)propyl]-N''-[4-phenyl-4-(pyrid-2-yl) butyl]-guanidine $C_{22}H_{28}N_6 \cdot 3HCl$ (485.9) Molar mass (MS): Calc.: 376.23754, Found: 376.23645

$[M-NH_3]^+$: Calc.: 359 21099, Found: 359.21030

MS: m/z (rel. Int. [%])=376 (M+, 4), 359(3), 295(8), 210(31), 196(16), 182(100), 168(75), 109(12), 95(35), 81(22).

$^1$H-NMR data ($d_6$-DMSO, TMS as internal standard): δ=1.41 (m) 2 H, 1.83 (m) 2 H, 2.15–2.55 (m) 2 H, 2.71 (t) 2 H. 3.1–3.35 (m) 4 H, 4.68 (t) 1 H, 7.15–7.7 (m) 8 H, 2 H replaceable by $D_2O$, 7.81 (m) 1 H, 7.93 (m) 1 H, replaceable by $D_2O$, 8.01 (m) 1 H, replaceable by $D_2O$, 8.10 (m) 1 H, 8.43 (m) 1 H, 8.76 (m) 1 H, 9.05 (s) 1 H, 14.4 (broad) 1 H, replaceable by $D_2O$, 14.8 (broad) 1 H, replaceable by $D_2O$, ppm.

EXAMPLE 137

N-[4-(4-Fluorophenyl)-4-(pyrid-2-yl)butyl]-N'-[3-(imidazol-4-yl)propyl]-guanidine

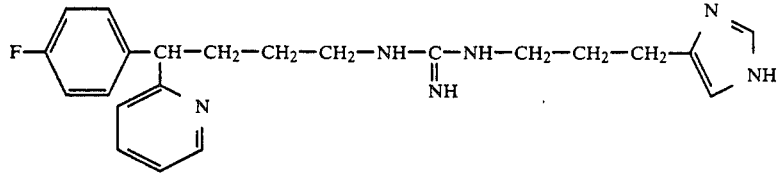

The method of preparation is analogous to that of Example 109, starting from 1.0 g (2 mmol) of N-benzoyl-N'-[4-(4-fluorophenyl)-4-(pyrid-2-yl)butyl]-N''-[3-(imidazol-4-yl)propyl]-guanidine.

Yield: 0.89 g (88%) of a hygroscopic, non-crystalline solid.

$C_{22}H_{27}FN_6 \cdot 3HCl$ (503.9)

$^1$H-NMR data ($d_6$-DMSO, TMS as internal standard): δ=1.43 (m) 2 H, 1.83 (m) 2 H, 2.15–2.6 (m) 2 H., 2.72 (t) 2 H, 3.1–3.4 (m) 4 H, 4.68 (t) 1 H, 7.19 (dd) 2 H, 7.4–7.65 (m) 5 H, 2 H replaceable by $D_2O$, 7.7–8.15 (m) 4 H, 2 H replaceable by $D_2O$, 8.36 (m) 1 H, 8.75 (m) 1 H, 9.05 (s) 1 H, 14.4 (broad) 1 H, replaceable by $D_2O$, 14.8 (broad) 1 H, replaceable by $D_2O$, ppm.

EXAMPLE 138

$N^1$-Benzoyl-$N^2$-[3-(4-imidazolyl)propyl]-$N^3$-[2-(N-benzyl-N-(pyrid-2-yl)amino)ethyl]-guanidine

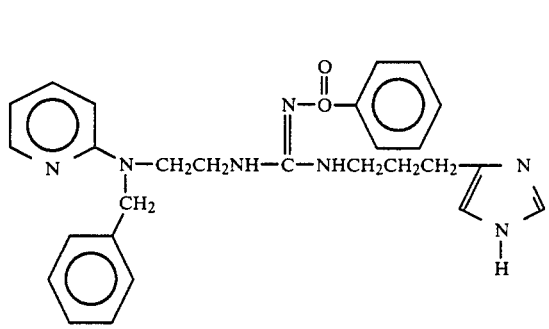

3.48 g (10 mmol) of $N^1$-benzoyl-$N^2$-[3-(4-imidazolyl)propyl]-O-phenyl-isourea and 2.27 g (10 mmol) of N-benzyl-N-pyrid-2-yl)-ethylene diamine are boiled in 50 ml of ethanol for 20 hours. After concentration of the reaction mixture by evaporation under vacuum, the crude product is chromatographed on silica gel with ethyl acetate/ethanol (80:20). After concentration by evaporation, the main fraction yields 3.51 g (73%) of a colourless solid.

$C_{28}H_{31}N_7O$ (481.60)

$^1$H-NMR data ($CD_3OD$, TMS as internal standard): δ=1.90 (m) 2 H, 2.67 (t) 2 H, 3.23 (t) 2 H, 3.71–3.89 (m) 4 H, 4.57 (s) 2 H, 4.9 (broad) 3 H, replaceable by $D_2O$, 6.43–7.57 (m) 13 H, 7.96–8.21 (m) 3 H, ppm.

EXAMPLE 139

N¹-Benzoyl-N2-[3-(1H-imidazol-4-yl)propyl]-N-[2-[N-(4-chlorobenzyl)-N-(pyridin-2-yl)-amino]-ethyl]-guanidine

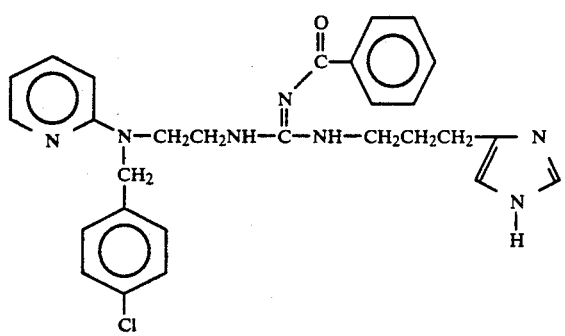

1.74 g (5 mmol) of N'-benzoyl-N--[3-(1H-imidazol-4-yl) propyl]-O-phenyl-isourea and 1.31 g (5 mmol) of N-(4-chlorobenzyl)-N-(pyridin-2-yl)-ethylene diamine are heated under reflux in 30 ml of ethanol for 24 hours. After concentration by evaporation, the crude product obtained is purified on silica gel with ethyl acetate/ethanol 80:20). The main fraction is concentrated by evaporation and the residue is recrystallised from ethyl acetate/tert.-butyl-methyl ether (1:1). 2.20 g (85%) of the title compound are obtained in the form of colourless crystals, melting point 166°–167° C.

$C_{28}H_{30}ClN_7O$ (516.04)

¹H-NMR data (d₆-DMSO, TMS as internal standard): δ = 1.70–2.03 (m) 2 H, 2.59 (t) 2 H. 3.10–3.48 (m) 2 H, 3.48–3.83 (m) 4 H, 4.79 (s) 2 H, 6.51–6.87 (m) 3 H, 7.11–7.63 (m) 9 H, 7.98–8.28 (m) 3 H, 10.0 (broad) 1 H, replaceable by D₂O, 10.3 (broad) 1 H, replaceable by D₂O, ppm.

EXAMPLE 140

N¹-[3-(4-imidazolyl)propyl]-N²-[2-(N-benzyl-N-(pyrid-2-yl)-amino)ethyl]-guanidine trihydrochloride

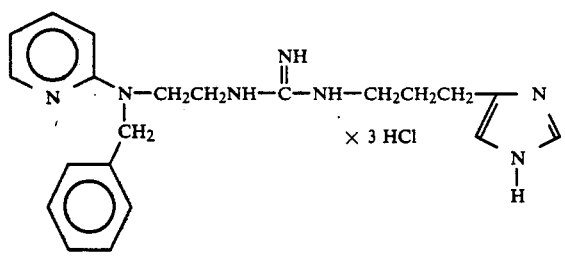

Method A 2.41 g (5.0 mmol) of N¹-benzoyl-N²-[3-(4-imidazolyl) propyl]-N³-[2-N-benzyl-N-(pyrid-2-yl)-amino)ethyl]-guanidine (Example 138) are boiled in 50 ml of conc. hydrochloric acid for 18 hours. After the reaction mixture has been concentrated by evaporation to half its original volume, it is extracted three times with 50 ml of ether. The aqueous phase is filtered and concentrated by evaporation and the residue is taken up twice with 20 ml of ethanol and evaporated to dryness. Recrystallisation of the residue from isopropanol/ethanol yields 1.17 g (48%) of the title compound.

$C_{21}H_{30}Cl_3N_7$ (486.88)

¹H-NMR data (CD₃OD (TMS as internal standard): δ = 1.80–2.19 (m) 2 H, 2.87 (t) 2 H, 3.34 (t) 2 H, 3.65 (m) 2 H, 3.78 (m) 2 H, 4.16 (t) 2 H, 4.9 (broad) 7 H, replaceable by D₂O, 7.21–8.10 (m) 10 H, 9.00 (s) 1 H, ppm.

Method B a) N¹-Benzoyl-N²-[2-(N-benzyl-N-(pyridin-2-yl)-amino) ethyl]-thiourea

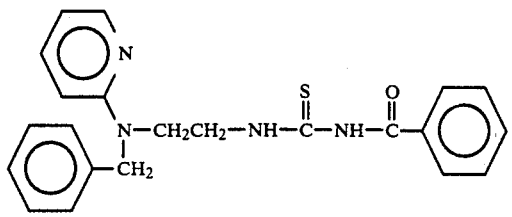

3.89 g (17 mmol) of N-benzyl-N-(pyridin-2-yl)-ethylene diamine and 2.79 g (17 mmol) of benzoyl isothiocyanate are heated under reflux in 70 ml of methylene chloride for 2 hours. After removal of the solvent by evaporation under vacuum, the residue is crystallised with ethyl acetate. 3.50 g (52%) of colourless crystals melting at 124.8°–125.7° C. are obtained.

$C_{22}H_{22}N_4OS$ (390.51)

¹H-NMR data (d₆-DMSO, TMS as internal standard): δ = 3.86 (s, broadened) 4 H, 4.83 (s) 2 H, 6.57 (dd) 1 H, 6.80 (d) 1 H, 7.28 (s) 5 H, 7.35–7.69 (m) 4 H, 7.85–8.06 (m) 2 H, 8.14 (dd) 1 H, 11.12 (broad) 1 H, replaceable by D₂O, 11.29 (broad) 1 H, replaceable by D₂O, ppm.

b) N-[2-(N-benzyl-N-(pyridin-2-yl)-amino)ethyl]-S-methyl-isothiouronium iodide

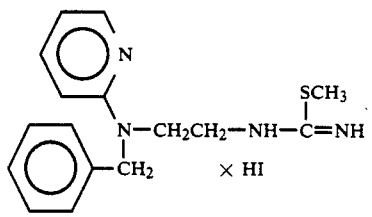

3.40 g (8.7 mmol) of N¹-benzoyl-N²-[2-(N-benzyl-N-(pyridin-2-yl)-amino)ethyl]-thiourea and 2.41 g (17.4 mmol) of potassium carbonate are boiled under reflux in 35 ml of water and 115 ml of methanol for 40 minutes. After evaporation under vacuum, the residue is taken up with 50 ml of ethyl acetate and washed three times with 20 ml portions of water. The organic phase is dehydrated over sodium sulphate, filtered and concentrated by evaporation under vacuum. The residue obtained is taken up with 110 ml of ethanol and stirred up with 0.7 ml of methyl iodide for 15 hours at room temperature. After evaporation of the solvent under vacuum, the residue is crystallised with ethyl acetate. 2.82 g (76%) of the isothiouronium iodide are obtained in the form of colourless crystals, melting point 152°–152.8° C.

$C_{16}H_{21}IN_4S$ (428.34)

¹H-NMR data (d₆-DMSO, TMS as internal standard): δ = 2.67 (s) 3 H, 3.40–3.99 (m) 4 H, 4.80 (s) 2 H, 6.52–6.83 (m) 2 H, 7.05–7.68 (m) 6 H, 8.18 (dd) 1 H, 9.53 (broad) 3 H, replaceable by D₂O, ppm.

N¹-[3-(1H-Imidazol-4-yl)propyl]-N²-[2-(N-benzyl-N-(pyridin-2-yl)-amino)ethyl]-guanidine 1.00 g (2.3 mmol) of N-[2-(N-benzyl-N-(pyridin-2-yl)-amino)ethyl]-S-methyl-isothiouronium iodide and 0.28 g (2.3 mmol) of 3-(1H-imidazol-4-yl)-propylamine are heated under reflux in 20 ml of pyridine for 3 hours. After evaporation of the solvent under vacuum, the residue is chromatographed on aluminium oxide with ethyl acetate/methanol (1:1) (triethylamine). After concentration by evaporation, the main fraction yields 0.83 g (94%) of the title compound as a colourless, amorphous solid.

$C_{21}H_{27}N_7$ (377.49)

$^1$H-NMR data (CD$_3$OD, TMS as internal standard):
δ = 1.89 (quin) 2 H, 2.65 (t) 2 H, 3.12–3.88 (m) 6 H, 4.70 (s) 2 H, 4.80 (broad) 4 H, 6.56–6.78 (m) 2 H, 6.86 (s) 1 H, 7.14–7.64 (m) 6 H, 7.60 (s) 1 H, 8.13 (dd) 1 H, ppm.

EXAMPLE 141

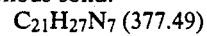
N$^1$-[3-(1H-Imidazol-4-yl)propyl]-N$^2$-[2-[N-(4-chlorobenzyl) N-(pyridin-2-yl).amino]ethyl]-guanidine

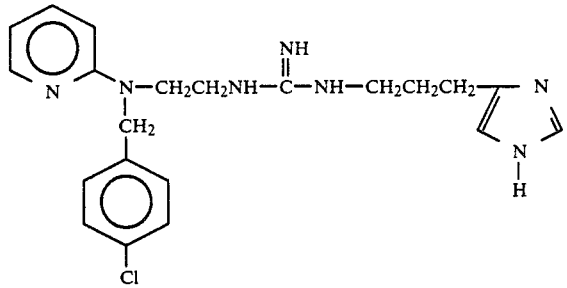

0.80 g (88%) of the title compound are obtained in the form of a colourless, amorphous solid from 1.00 g (2.2 mmol) of N-[2-[N-(4-chlorobenzyl)N-(pyridin-2-yl)ethyl]-S-methyl-isothiouronium iodide and 0.30 g (2.4 mmol) of 3-(1H-imidazol-4-yl)-propylamine (analogously to Example 140 (Method B).

$C_{21}H_{26}ClN_7$ (411.94)

$^1$H-NMR data (CD$_3$OD, TMS as internal standard):
δ = 1.75–2.21 (m) 2 H, 2.70 (t) 2 H, 3.16–3.93 (m) 6 H, 4.70 (s) 2 H, 5.4 (broad) 4 H, 6.52–6.81 (m) 2 H, 6.91 (s) 1 H, 7.14–7.63 (m) 5 H, 7.67 (s) 1 H, 8.20 (dd) 1 H, ppm.

EXAMPLE 142

N$^1$-[3-(1H-Imidazol-4-yl)propyl]-N2-[2-[N-(4-methoxybenzyl)-N-(pyridin-2-yl)-amino]ethyl]-guanidine

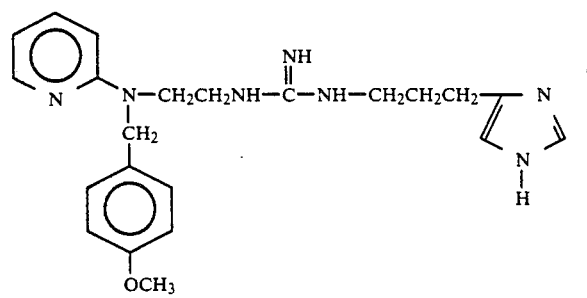

The title compound is obtained by a method analogous to that of Example 140 from 1.00 g (2.2 mmol) of N-[2-[N-(4-methoxybenzyl)N-(pyridin-2-yl)-amino]ethyl]-S-methyl-isothiouronium iodide and 0.30 g (2.4 mmol) of 3-(1H-imidazol-4-yl)-propylamine.

Yield: 0.39 g (44%) of a colourless, amorphous solid.

$C_{22}H_{29}N_7O$ (407.52)

$^1$H-NMR data (CD$_3$OD, TMS as internal standard):
δ = 1.93 (quin) 2 H, 2.69 (t) 2 H, 3.13–3.91 (m) 6 H, 3.73 (s) 3 H, 4.62 (s) 2 H, 5.2 (broad) 4 H, 6.56–7.73 (m) 8 H, 7.64 (s) 1 H, 8.16 (s) 1 H, ppm.

EXAMPLE 143

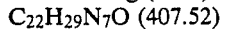
N$^1$-[3-(1H-Imidazol-4-yl)propyl]-N$^2$-[2-[N-(4-fluorobenzyl)-N-(pyridin-2-yl)-amino]ethyl]-guanidine

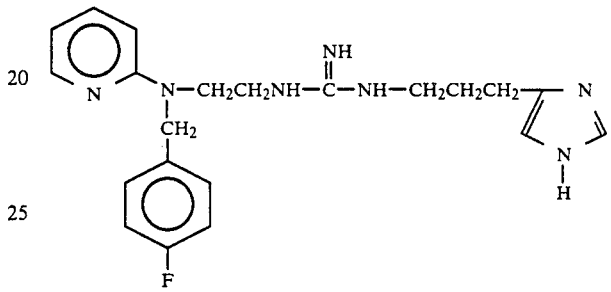

The compound is prepared by a method analogous to that of Example 140 from 2.00 g (4.48 mmol) of N-[2-N-(4-fluorobenzyl)-N-(pyridin-2-yl)-amino]ethyl]-S-methyl-isothiouronium iodide and 0.63 g(4.93 mmol) of 3-(1H-imidazol-4-yl)-propylamine in 40 ml of pyridine. 1.08 g (61%) of the title compound is obtained as a beige coloured solid after purification of the crude product by preparative layer chromatography and crystallisation from methylene chloride. Melting point 60°–63° C.

$C_{21}H_{26}FN_7$ (395.49)

$^1$H-NMR data (CD$_3$OD, TMS as internal standard):
δ = 1.91 (quin) 2 H, 2.68 (t) 2 H, 3.12–3.58 (m) 4 H, 3.61–3.90 (m) 2 H, 4.63 (s) 2 H, 4.7 (broad) 4 H, 6.58–7.65 (m) 8 H, 7.73 (s) 1 H, 8.16 (dd) 1 H, ppm.

EXAMPLE 144

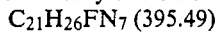
N$^1$-[2-[N-(5-Bromo-3-methyl-pyridin-2-yl)-benzylamino]ethyl]-N$^2$-[3-(1H-imidazol-4-yl)propyl]-guanidine trihydrochloride

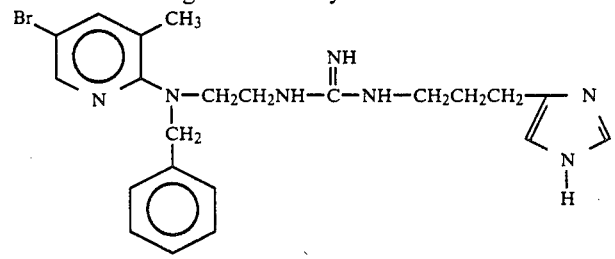

The method of preparation is analogous to that of Example 140.

0.82 g (71%) of a colourless, highly hygroscopic solid
$C_{22}H_{31}BrCl_3N_7$ (579.80)

¹H-NMR data (CD₃OD, TMS as internal standard):
δ=1.80–2.18 (m) 2 H, 2.61 (s) 3 H, 2.89 (t) 2 H, 3.34 (t) 2 H, 3.60 (m) 2 H, 3.83 (m) 2 H, 4.15 :t) 2 H, 4.9 (broad) 7 H, 7.37–7.55 (m) 6 H, 8.84 (d) 1 H, 8.92 (d) 2 H, ppm.

EXAMPLE 145

N¹-[3-(Imidazol-4-yl)propyl]-N²-[2-(diphenylamino)ethyl]-guanidine trihydrochloride

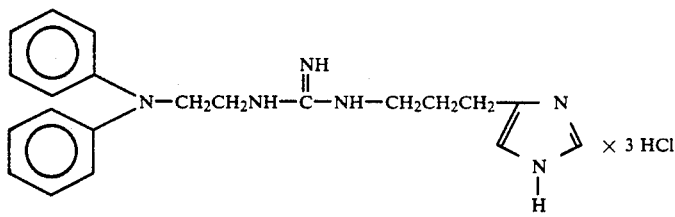

The method of preparation is analogous to that of Example 101.

C₂₁H₂₉Cl₃N₆ (471.9)

¹H-NMR data (CD₃OD, TMS as internal standard):
δ=1.81–2.20 (m) 2 H, 2.90 (t) 2 H, 3.30 (t) 2 H, 3.60 (m) 2 H, 4.13 (t) 2 H, 4.85 (broad) 7 H, 7.2–7.9 (m) 11 H, 9.00 (s) 1 H, ppm.

EXAMPLE 146

N¹-[3-(Imidazol-4-yl)propyl]-N²-[2-N-(phenyl-N(4-fluorophenyl)amino)ethyl]-guanidine trihydrochloride

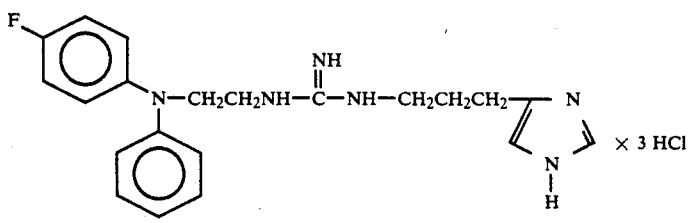

The method of preparation is analogous to that of Example 101.

C₂₁H₂₈Cl₃FN₆ (489.9)

¹H-NMR data (CD₃OD, TMS as internal standard):
δ=1.80–2.19 (m) 2 H, 2.88 (t) 2 H, 3.30 (t) 2 H, 3.58 (m) 2 H, 4.11 (t) 2 H, 4.85 (broad) 7 H, 7.30–7.9 (m) 10 H, 9.01 (s) 1 H, ppm.

EXAMPLE 147

N¹-[3-(Imidazol-4-yl)propyl]-N²-[2-(N-(2-pyridyl)-N-phenylamino)ethyl]-guanidine trihydrochloride

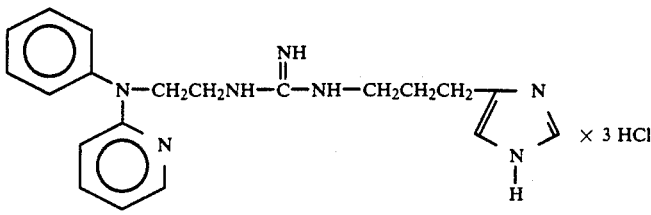

The method of preparation is analogous to that of Example 101.

C₂₀H₂₈Cl₃N₇ (472.9)

¹H-NMR data (CD₃OD, TMS as internal standard):
δ=1.81–2.20 (m) 2 H, 2.87 (t) 2 H, 3.32 (t) 2 H, 3.60 (m) 2 H, 4.12 (t) 2 H, 4.90 (broad) 7 H, 7.24–8.15 (m) 10 H, 9.02 (s) 1 H, ppm.

EXAMPLE 148

N¹-[3-(Imidazol-4-yl)propyl]-N²-[2-(N-(2-pyridyl)N-(4-fluorophenyl)amino)ethyl]-guanidine trihydrochloride

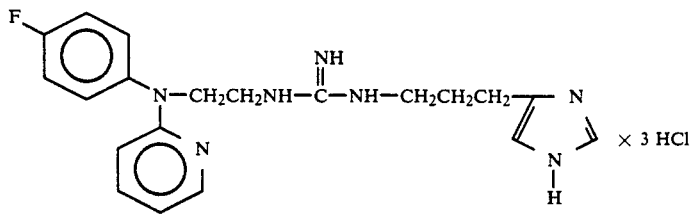

The method of preparation is analogous to that of Example 101.

C₂₀H₂₇Cl₃FN₇ (490.8)

¹H-NMR data (CD₃OD, TMS as internal standard):
δ1.80–2.18 (m) 2 H, 2.90 (t) 2 H, 3.32 (t) 2 H, 3.61 (m) 2 H, 4.11 (t) 2 H, 4.86 (broad) 7 H, 7.15–8.20 (m) 9 H, 9.01 (s) 1 H ppm.

We claim:

1. An imidazolyl alkyl guanidine derivative corresponding to the formula I

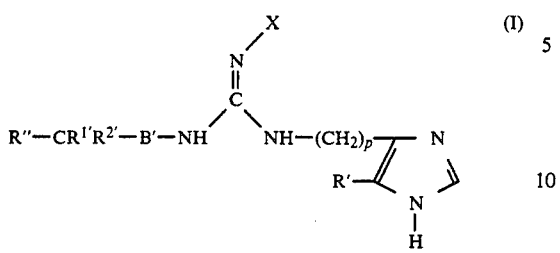

wherein X denotes hydrogen or benzoyl; p has the value 2 or 3; R' denotes hydrogen or methyl; R" represents phenyl, pyridine, thiophene, or naphthyl, each of which may be unsubstituted or substituted with a halogen atom, $C_1$-$C_3$-alkyl or $C_1$-$C_3$-alkoxy; $R^{1'}$ denotes hydrogen or methyl and $R^{2'}$ denotes phenyl or pyridyl, each of said phenyl or pyridyl may be unsubstituted or substituted with at least one halogen atom or $C_1$-$C_3$-alkyl; and B' represents the group —CH(Y)—S—$(CH_2)_{m'}$—, —$CH_2$—S—$CH_2$—CH(Y)—$CH_2$—, —$CH_2$—S—CH(Y)—$CH_2$—, —$CH_2$—S—$CH_2$—CH(Y)—, —$(CH_2)_{n''}$—, —$(CH_2)_{n''}$—CH(Y)—, —O—$(CH_2)_2$—, —$CH_2$—O—$(CH_{2o'})$—, —$CH_2$—O—$CH_2$—CH(Y)—$CH_2$—, —O—$CH_2$—CH(Y)—, —O—CH(Y)—$CH_2$—, —S—$(CH_2)_q$—, —S—$CH_2$—CH(Y)—, —S—CH(Y)—$CH_2$— or —S—$CH_2$—CH(Y)—$CH_2$— wherein Y denotes hydrogen or a straight chain $C_1$-$C_3$-alkyl, m' and o' have the value 2 or 3, and n" and q have the value 2, 3, 4 or 5.

2. A composition of matter comprising (i) the imidazolyl alkyl guanidine compound as claimed in claim 1, or a pharmaceutically effective salt thereof, and (ii) a pharmaceutically acceptable carrier or diluent thereof, said composition having therapeutic susceptibility to a compound displaying both an $H_1$-antagonistic and an $H_2$-agonistic activity in a mammalian organism in need of treatment for hypertension, cardiac disease or diseases of arterial occlusion.

3. A compound according to claim 1, wherein R" is a substituted or unsubstituted phenyl, B' is –$(CH_2)_{n''}$, wherein n" is 2, 3 or 4, X and R' are hydrogen, and p is 3.

4. A method for eliciting an agonistic response on histamine —$H_2$ receptors and an antagonistic response on $H_1$-receptors in a mammalian organism, comprising administering to such organism a pharmaceutically effective amount of the imidazolyl alkyl guanidine compound as claimed in claim 1, or a pharmaceutically active salt thereof.

5. A method for treating cardiac disease susceptible to a compound displaying both an $H_1$-antagonistic and an $H_2$-agonistic activity in a mammalian organism in need of such treatment, comprising administering to said organism a therapeutically effective amount of imidazolyl alkyl guanidine compound as claimed in claim 1, or a pharmaceutically effective salt thereof.

6. A method for treating hypertension in a mammalian organism in need of such treatment, comprising administering to said organism a therapeutically effective amount of the imidazoyl alkyl guanidine compound as claimed in claim 1, or a pharmaceutically effective salt thereof.

7. A method for treating arterial occlusion in a mammalian organism in need of such treatment, comprising administering to said organism a therapeutically effective amount of the imidazolyl alkyl guanidine compound as claimed in claim 1, or a pharmaceutically effective salt thereof.

8. An imidazolyl alkyl guanidine derivative corresponding to the formula I

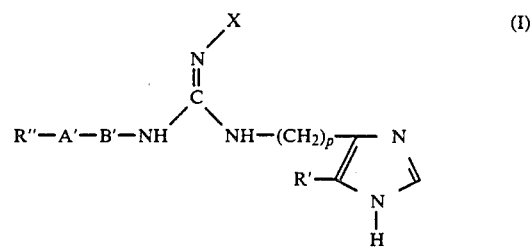

wherein X denotes hydrogen or benzoyl; p has the value 2 or 3; R' denotes hydrogen atom or methyl; R" represents phenyl, pyridine, thiophene or naphthyl, each of which may be unsubstituted or substituted with a halogen atom, $C_1$-$C_3$-alkyl or $C_1$-$C_3$-alkoxy; A' represents nitrogen substituted with hydrogen, a straight chain $C_1$-$C_3$-alkyl, phenyl or benzyl, each of said phenyl or benzyl may be unsubstituted or substituted with at least one halogen atom or $C_1$-$C_3$-alkoxy; and B' represents the group —CH(Y)—S—$(CH_2)_{m'}$—, —$CH_2$—S—$CH_2$—CH(Y)—, —$(CH_2)_{n''}$—, —$(CH_2)_{n''}$—CH(Y)—, —$CH_2$—O—$(CH_2)_{o'}$—, or —$Ch_2$—O—$CH_2$—CH(Y)—$CH_2$—, wherein Y denotes hydrogen or a straight chain $C_1$-$C_3$-alkyl, m' and o' have the value 2 or 3, and n" has the value 2, 3, 4 or 5.

9. A composition of matter comprising (i) the imidazolyl alkyl guanidine compound as claimed in claim 8, or a pharmaceutically effective salt thereof, and (ii) a pharmaceutically acceptable carrier or diluent thereof, said composition having therapeutic susceptibility to a compound displaying both an $H_1$-antagonistic and an $H_2$-agonistic activity in a mammalian organism in need of treatment for hypertension, cardiac disease or diseases of arterial occlusion.

10. A compound according to claim 8, wherein R" is a substituted or unsubstituted phenyl, A' is nitrogen substituted with phenyl or benzyl, B' is —$(CH_2)_{n''}$, wherein n" is 2 or 3, X and R' are each hydrogen and p is 3.

11. A method for eliciting an agonistic response on histamine —$H_2$ receptors and an antagonistic response on $H_1$-receptors in a mammalian organism, comprising administering to such organism a pharmaceutically effective amount of the imidazolyl alkyl guanidine compound as claimed in claim 8, or a pharmaceutically active salt thereof.

12. A method for treating cardiac disease susceptible to a compound displaying both an $H_1$-antagonistic and an $H_2$-agonistic activity in a mammalian organism in need of such treatment, comprising administering to said organism a therapeutically effective amount of imidazolyl alkyl guanidine compound as claimed in claim 8, or a pharmaceutically effective salt thereof.

13. A method for treating hypertension in a mammalian organism in need of such treatment, comprising administering to said organism a therapeutically effective amount of the imidazolyly alkyl guanidine compound as claimed in claim 8, or a pharmaceutically effective salt thereof.

14. A method for treating arterial occlusion in a mammalian organism in need of such treatment, comprising administering to said organism a therapeutically effective amount of the imidazolyl alkyl guanidine compound as claimed in claim 8, or a pharmaceutically effective salt thereof.

15. N-Benzoyl-N'-[3-(imidazol-4-yl)propyl]-N''-[2-[(p-methyl-α-phenylbenzyl)thio]ethyl]-guanidine and the physiologically acceptable salts thereof.

16. N-[3-(Imidazol-4-yl)propyl-N'-[2-[(p-methyl-α-phenylbenzyl)thio]ethyl]-guanidine and the physiologically acceptable salts thereof.

17. N-Benzoyl-N'-[3-(imidazol-4-yl)propyl]-N''-(3,3-diphenylpropyl)-guanidine and the physiologically acceptable salts thereof.

18. N-[3-(Imidazol-4-yl)propyl]-N'-(3,3-diphenylpropyl)-guanidine and the physiologically acceptable salts thereof.

19. N-Benzoyl-N'-[3-(5-methylimidazol-4-yl)propyl]-N''-(3,3-diphenylpropyl)-guanidine and the physiologically acceptable salts thereof.

20. N-[3-(5-Methylimidazol-4-yl)propyl]-N'-(3,3-diphenylpropyl)-guanidine and the physiologically acceptable salts thereof.

21. N-[3-(Imidazol-4-yl)propyl]-N'-(4,4-diphenylbutyl)-guanidine and the physiologically acceptable salts thereof.

22. N-Benzoyl-N'-[3-(imidazol-4-yl)propyl]-N''-[2-[(phenyl(pyrid-2-yl)methyl)thio]-ethyl]-guanidine and the physiologically acceptable salts thereof.

23. N-[3-(Imidazol-4yl)propyl]-N'-[2-[(phenyl(pyrid-2-yl)methyl)thio]ethyl]-guanidine and the physiologically acceptable salts thereof.

24. N-Benzoyl-N'-[3-(imidazol-4-yl-)propyl]-N''-(3-phenyl-3-(pyrid-2-yl)propyl]-guanidine and the physiologically acceptable salts thereof.

25. N-[3-(Imidazol-4-yl)propyl]-N'-[3-phenyl-3-(pyrid-2-yl)propyl]-guanidine and the physiologically acceptable salts thereof.

26. N-Benzoyl-N'-[3-(4-chlorophenyl)-3-(pyrid-2-yl)propyl]-N''-[3-(imidazol-4-yl)propyl]-guanidine and the physiologically acceptable salts thereof.

27. N-[3-(4-Chlorophenyl)-3-(pyrid-2-yl)propyl]-N'-[3-(imidazol-4-yl)propyl]-guanidine and the physiologically acceptable salts thereof.

28. N-Benzoyl-N'-[3-(4-bromophenyl)-3-(pyrid-2yl)propyl]-N''-[3-(imidazol-4-yl)propyl]-guanidine and the physiologically acceptable salts thereof.

29. N-[3-(4-Bromophenyl)-3-(pyrid-2-yl)propyl]-N'-[3-(imidazol-4-yl)propyl-guanidine and the physiologically acceptable salts thereof.

30. N-Benzoyl-N'-[3-(4-fluorophenyl)-3-(pyrid-2-yl)propyl]-N''-[3-imidazol-4-yl)propyl]-guanidine and the physiologically acceptable salts thereof.

31. N-[3-(4-Fluorophenyl)-3-(pyrid-2-yl)propyl]-N'[3-imidazol-4-yl)propyl]-guanidine and the physiologically acceptable salts thereof.

32. N-[3-(Imidazol-4-yl)propyl]-N'-[3-(pyrid-2-yl)-3-(2-thienyl)propyl]-guanidine and the physiologically acceptable salts thereof.

33. N-Benzoyl-N'-[3-(imidazol-4-yl)propyl]-N''-[4-phenyl-4-(pyrid-2-yl)butyl-guanidine and the physiologically acceptable salts thereof.

34. N-[3-(Imidazol-4-yl)propyl]-N'-[4-phenyl-4-(pyrid-2-yl)butyl]-guanidine and the physiologically acceptable salts thereof.

35. N-[4-(4-Fluorophenyl)-4-(pyrid-2-yl)butyl]-N'-[3-imidazol-4-yl)-propyl]-guanidine and the physiologically acceptable salts thereof.

36. N-[3-[N-(5-Methyl-pyrid-2-yl)-methylamino]propyl]-$N^2$-[2-(1H-imidazol-4-yl)ethyl]-guanidine trihydrochloride and the physiologically acceptable salts thereof.

37. $N^1$-Benzoyl-$N^2$-[3-[N-(5-methyl-pyridin-2-yl)-methylamino]propyl]-$N^2$-[3-(1H-imidazol-4-yl)propyl]-guanidine and the physiologically acceptable salts thereof.

38. $N^1$-[3-[N-(5-Methyl-pyridin-2-yl)-methylamino]propyl]-$N^2$-[3-(1H-imidazol-4-yl)propyl]-guanidine trihydrochloride and the physiologically acceptable salts thereof.

39. $N^1$-Benzoyl-$N^2$-[3-(1H-imidazol-4-yl)propyl]-$N^3$-[2-(pyridin-2-ylamino)ethyl]-guanidine and the physiologically acceptable salts thereof.

40. $N^1$-[3-(1H-Imidazol-4-yl)propyl]-$N^2$-[2-(pyridin-2-yl-amino)ethyl]-guanidine trihydrochloride and the physiologically acceptable salts thereof.

41. $N^1$-Benzoyl-$N^2$-[3-(4-imidazolyl)propyl]-$N^3$-[2-(N-benzyl-N-phenylamino)-ethyl]-guanidine and the physiologically acceptable salts thereof.

42. $N^1$-[3-(4-Imidazolyl)propyl]-$N^2$-[2-(N-benzyl-N-phenyl-amino)-ethyl]-guanidine trihydrochloride and the physiologically acceptable salts thereof.

43. $N^1$-[3-(4-Imidazolyl)propyl]-$N^2$-[2-(N-benzyl-N-(4-fluoro-phenyl)amino)ethyl]-guanidine trihydrochloride and the physiologically acceptable salts thereof.

44. $N^1$-[3-(4-Imidazolyl)propyl]-$N^2$-[2-(N-benzyl-N-(4-bromophenyl)amino)ethyl]-guanidine trihydrochloride and the physiologically acceptable salts thereof.

45. $N^1$-[3-(4-Imidazolyl)propyl]-$N^2$-[2-(N-benzyl-N-(4-bromophenyl)amino)ethyl]-guanidine trihydrochloride and the physiologically acceptable salts thereof.

46. $N^1$-Benzoyl-$N^2$-[3-(4-imidazolyl)propyl]-$N^3$-[2-(N-benzyl-N-(pyrid-2-yl)amino)ethyl]-guanidine and the physiologically acceptable salts thereof.

47. $N^1$-Benzoyl-$N^2$-[3-(1H -imidazol-4-yl)propyl]-$N^3$[2-[N-(4chlorobenzyl)-N-(pyridin-2-yl)-amino]-ethyl]-guanidine and the physiologically acceptable salts thereof.

48. $N^1$-[3-(4-imidazolyl)propyl]-$N^2$-[2-(N-benzyl-N-(pyrid-2-yl)-amino)ethyl]-guanidine trihydrochloride and the physiologically acceptable salts thereof.

49. $N^1$-[3-(1H-Imidazol-4-yl)propyl]-$N^2$-[2-[N-(4-chlorobenzyl)-N-(pyridin-2-yl)-amino]ethyl]-guanidine and the physiologically acceptable salts thereof.

50. $N^1$-[3-(1H-Imidazol-4-yl)-propyl]-$N^2$-['2-[N-(4-methoxybenzyl)-N-(pyridin-2-yl)-amino]ethyl]-guanidine and the physiologically acceptable salts thereof.

51. $N^1$-[3-(1H-Imidazol-4-yl)-propyl]-$N^2$-[2-N-(4-fluorobenzyl)-N-(pyridin-2-yl)-amino]ethyl]-guanidine and the physiologically acceptable salts thereof.

52. $N^1$-[2-[N-(5-Bromo-3-methyl-pyridin-2-yl)-benzylamino]ethyl]-$N^2$-[3-(1H-imidazol-4-yl)propyl]-guanidine trihydrochloride and the physiologically acceptable salts thereof.

53. $N^1$-[3-(Imidazol-4-yl)propyl]-$N^2$-[2-(diphenylamino)ethyl]-guanidine trihydrochloride and the physiologically acceptable salts thereof.

54. $N^1$-[3-(Imidazol-4-yl)propyl]-$N^2$-[2-N-(phenyl-N(4-fluorophenyl)amino)ethyl]-guanidine trihydrochloride and the physiologically acceptable salts thereof.

55. $N^1$-[3-(Imidazol-4-yl)propyl]-$N^2$-[2-pyridyl)-N-phenylamino)ethyl]-guanidine trihydrochloride and the physiologically acceptable salts thereof.

56. $N^1$-[3-(imidazol-4-yl)propyl]-$N^2$-[2-(N-(2-pyridyl)-N-(4-fluorophenyl)amino)ethyl]-guanidine trihydrochloride and the physiologically acceptable salts thereof.

* * * * *